US012344635B2

(12) United States Patent
Barbieri et al.

(10) Patent No.: US 12,344,635 B2
(45) Date of Patent: Jul. 1, 2025

(54) COVID-19 VACCINE

(71) Applicants: The Medical College of Wisconsin, Inc., Milwaukee, WI (US); Wisconsin Alumni Research Foundation, Madison, WI (US)

(72) Inventors: Joseph T. Barbieri, New Berlin, WI (US); Amanda Przedpelski, Milwaukee, WI (US); Eric A. Johnson, Madison, WI (US); Sabine Pellett, Madison, WI (US); William H. Tepp, Stoughton, WI (US)

(73) Assignees: The Medical College of Wisconsin, Inc., Milwaukee, WI (US); Wisconsin Alumni Research Foundation, Madison, WI (US)

( * ) Notice: Subject to any disclaimer, the term of this patent is extended or adjusted under 35 U.S.C. 154(b) by 1135 days.

(21) Appl. No.: 17/211,379

(22) Filed: Mar. 24, 2021

(65) Prior Publication Data
US 2021/0300970 A1    Sep. 30, 2021

Related U.S. Application Data

(60) Provisional application No. 63/104,360, filed on Oct. 22, 2020, provisional application No. 62/994,081, filed on Mar. 24, 2020.

(51) Int. Cl.
| | | |
|---|---|---|
| *A61K 39/00* | (2006.01) | |
| *A61K 39/08* | (2006.01) | |
| *A61K 39/215* | (2006.01) | |
| *A61K 47/55* | (2017.01) | |
| *C07K 14/005* | (2006.01) | |
| *C07K 14/33* | (2006.01) | |

(52) U.S. Cl.
CPC ............ *C07K 14/005* (2013.01); *A61K 39/08* (2013.01); *A61K 39/215* (2013.01); *C07K 14/33* (2013.01)

(58) Field of Classification Search
CPC .. C07K 14/33; C07K 2319/55; C07K 14/005; A61K 39/215; A61K 2039/5156
See application file for complete search history.

(56) References Cited

U.S. PATENT DOCUMENTS

| | | |
|---|---|---|
| 2005/0238663 A1 | 10/2005 | Hunt |
| 2008/0221012 A1 | 9/2008 | Steward |
| 2011/0318385 A1 | 12/2011 | Jackson |

FOREIGN PATENT DOCUMENTS

| | | |
|---|---|---|
| CN | 1178472 A | 4/1998 |
| WO | 200100839 A1 | 1/2001 |
| WO | 2019118974 A | 6/2019 |

OTHER PUBLICATIONS

Lam, K.H., et al. (2015). Diverse binding modes, same goal: The receptor recognition mechanism of botulinum neurotoxin. Prog Biophys Mol Biol 117, 225-231.

Lapenotiere, H.F., et al. (1995). Expression of a large, nontoxic fragment of botulinum neurotoxin serotype A and its use as an immunogen. Toxicon : official journal of the International Society on Toxinology 33, 1383-1386.

Lees, A.; et al., Activation of soluble polysaccharides with 1-cyano-4-dimethylaminopyridinium tetrafluoroborate for use in protein-polysaccharide conjugate vaccines and immunological reagents. Vaccine 1996, 14 (3), 190-8.

Li, J., et al. (2015). Intranasal vaccination with an engineered influenza virus expressing the receptor binding subdomain of botulinum neurotoxin provides protective immunity against botulism and influenza. Front Immunol 6, 170.

Lin, G., et al. (2010). Expression of the Clostridium botulinum A2 neurotoxin gene cluster proteins and characterization of the A2 complex. Applied and Environmental Microbiology 76, 40-47.

Lou, J.; et al., A Single Tri-Epitopic Antibody Virtually Recapitulates the Potency of a Combination of Three Monoclonal Antibodies in Neutralization of Botulinum Neurotoxin Serotype A. Toxins (Basel) 2018, 10 (2).

Lou, J.; et al., Affinity maturation of human botulinum neurotoxin antibodies by light chain shuffling via yeast mating. Protein Eng Des Sel 2010, 23 (4), 311-9.

Malizio, C.J., et al. (2000). Purification of Clostridium botulinum type A neurotoxin. Methods in molecular biology (Clifton, NJ) 145, 27-39.

Masuyer, G.; et al., The structure of the tetanus toxin reveals pH-mediated domain dynamics. EMBO Rep 2017, 18 (8), 1306-1317.

Mayer, S.; et al., Analysis of the immune response against tetanus toxoid: enumeration of specific T helper cells by the Elispot assay. Immunobiology 2002, 205 (3), 282-9.

McGuirk, P.; et al., Pathogen-specific regulatory T cells provoke a shift in the Th1/Th2 paradigm in immunity to infectious diseases. Trends Immunol 2002, 23 (9), 450-5.

Montal, M. "Botulinum neurotoxin: a marvel of protein design." Annual review of biochemistry 79 (2010): 591-617.

Montecucco, C., et al. (1993). Tetanus and botulism neurotoxins: a new group of zinc proteases. Trends in biochemical sciences 18, 324-327.

(Continued)

*Primary Examiner* — Barry A Chestnut
(74) *Attorney, Agent, or Firm* — Quarles & Brady LLP

(57) ABSTRACT

Provided herein are antigenic peptides comprising the SARS-COV-2 spike protein receptor binding domain (CRBD) polypeptide or portions thereof, linked to a non-catalytic, non-toxic tetanus toxin variant (i.e., a modified tetanus toxin or "MTT") and vaccine compositions comprising the same. In addition, provided herein are methods for making and using CRBD-MTT fusion proteins as immunogenic agents.

26 Claims, 7 Drawing Sheets
(4 of 7 Drawing Sheet(s) Filed in Color)
Specification includes a Sequence Listing.

(56) References Cited

OTHER PUBLICATIONS

Montecucco, C., et al. (2004). Presynaptic receptor arrays for clostridial neurotoxins. Trends in microbiology 12, 442-446.
Moyron-Quiroz, J. E.; et al., The smallpox vaccine induces an early neutralizing IgM response. Vaccine 2009, 28 (1), 140-7.
Mustafa, W., et al. (2011). Immunization of mice with the non-toxic HC50 domain of botulinum neurotoxin presented by rabies virus particles induces a strong immune response affording protection against high-dose botulinum neurotoxin challenge. Vaccine 29, 4638-4645.
Nabel, G. J., Designing tomorrow's vaccines. N Engl J Med 2013, 368 (6), 551-60.
Needleman, S. B., et al. "A general method applicable to the search for similarities in the amino acid sequence of two proteins." Journal of molecular biology 48.3 (1970): 443-453.
Nencioni, L.; et al., Properties of pertussis toxin mutant PT-9K/129G after formaldehyde treatment. Infect Immun 1991, 59 (2), 625-30.
Oshima, M.; et al., Immune recognition of botulinum neurotoxin type A: regions recognized by T cells and antibodies against the protective H(C) fragment (residues 855-1296) of the toxin. Mol Immunol 1997, 34 (14), 1031-40.
Payne, J. R.; et al., Efficacy of Human Botulism Immune Globulin for the Treatment of Infant Botulism: The First 12 Years Post Licensure. J Pediatr 2017.
Pellett, S., et al. (2007). A neuronal cell-based botulinum neurotoxin assay for highly sensitive and specific detection of neutralizing serum antibodies. FEBS letters 581, 4803-4808.
Pellett, S., et al. (2010). Comparison of the primary rat spinal cord cell (RSC) assay and the mouse bioassay for botulinum neurotoxin type A potency determination. Journal of pharmacological and toxicological methods 61, 304-310.
Pellett, S., et al. (2016). Purification and Characterization of Botulinum Neurotoxin FA from a Genetically Modified Clostridium botulinum Strain. mSphere 1.
Pellett, S., et al., Assessment of ELISA as endpoint in neuronal cell-based assay for BoNT detection using hiPSC derived neurons. J Pharmacol Toxicol Methods 2017, 88 (Pt 1), 1-6.
Pellett, S., et al., Substrate cleavage and duration of action of botulinum neurotoxin type FA ("H, HA"). Toxicon 2018, 147, 38-46.
Perry, C. M., Meningococcal groups C and Y and haemophilus B tetanus toxoid conjugate vaccine (HibMenCY-TT; MenHibrix((R))): a review. Drugs 2013, 73 (7), 703-13.
Pier, C.L., et al. (2008). Recombinant holotoxoid vaccine against botulism. Infect Immun 76, 437-442.
Przedpelski, A., et al. "Enhancing toxin-based vaccines against botulism." Vaccine 36.6 (2018): 827-832.
Przedpelski, A., et al. (2013). Enhancing the protective immune response against botulism. Infect Immun 81, 2638-2644.
Rai, D., et al. (2009). Tracking the total CD8 T cell response to infection reveals substantial discordance in magnitude and kinetics between inbred and outbred hosts. J Immunol 183, 7672-7681.
Rao, K. N.; et al., Structural analysis of the catalytic domain of tetanus neurotoxin. Toxicon 2005, 45 (7), 929-39.
Rappuoli, R., Glycoconjugate vaccines: Principles and mechanisms. Sci Transl Med 2018, 10 (456).
Rappuoli, R., The vaccine containing recombinant pertussis toxin induces early and long-lasting protection. Biologicals 1999, 27 (2), 99-102.
Rappuoli, R.; et al., Progress towards the development of new vaccines against whooping cough. Vaccine 1992, 10 (14), 1027-32.
Ravichandran, E., et al. (2016). In Vivo Toxicity and Immunological Characterization of Detoxified Recombinant Botulinum Neurotoxin Type A. Pharm Res 33, 639-652.
Rummel, A.; et al., Botulinum neurotoxins C, E and F bind gangliosides via a conserved binding site prior to stimulation-dependent uptake with botulinum neurotoxin F utilising the three isoforms of SV2 as second receptor. J Neurochem 2009, 110 (6), 1942-54.
Schantz, E.J. et al. (1978). Standardized assay for Clostridium botulinum toxins. Journal of the Association of Official Analytical Chemists 61, 96-99.
Schiavo, G., et al. (2000). Neurotoxins affecting neuroexocytosis. Physiological reviews 80, 717-766.
Schmidt, J. J.; et al., Partial amino acid sequence of the heavy and light chains of botulinum neurotoxin type A. Biochem Biophys Res Commun 1984, 119 (3), 900-4.
Schwarz, P. J.; et al., Botulism immune globulin for infant botulism arrives—one year and a Gulf War later. West J Med 1992, 156 (2), 197-8.
Shone, C., et al. (2009). Bivalent recombinant vaccine for botulinum neurotoxin types A and B based on a polypeptide comprising their effector and translocation domains that is protective against the predominant A and B subtypes. Infect Immun 77, 2795-2801.
Sikorra, S.; et al., Substrate recognition mechanism of VAMP/synaptobrevin-cleaving clostridial neurotoxins. J Biol Chem 2008, 283 (30), 21145-52.
Skurnik, D.; et al., The exceptionally broad-based potential of active and passive vaccination targeting the conserved microbial surface polysaccharide PNAG. Expert Rev Vaccines 2016, 15 (8), 1041-53.
Smith, L. A., Botulism and vaccines for its prevention. Vaccine 2009, 27 Suppl 4, D33-9.
Specht, C. A.; et al., Protection against Experimental Cryptococcosis following Vaccination with Glucan Particles Containing Cryptococcus Alkaline Extracts. MBio 2015, 6 (6), e01905-15.
Strotmeier, J.; et al., Identification of the synaptic vesicle glycoprotein 2 receptor binding site in botulinum neurotoxin A. FEBS Lett 2014, 588 (7), 1087-93.
Sundeen, G.; et al., Vaccines against Botulism. Toxins (Basel) 2017, 9 (9).
Tepp, W.H., et al. (2012). Purification and characterization of a novel subtype a3 botulinum neurotoxin. Appl Environ Microbiol 78, 3108-3113.
Torii, Y., et al. (2002). Production and immunogenic efficacy of botulinum tetravalent (A, B, E, F) toxoid. Vaccine 20, 2556-2561.
Travassos, L. R.; et al., Linear Epitopes of Paracoccidioides brasiliensis and Other Fungal Agents of Human Systemic Mycoses As Vaccine Candidates. Front Immunol 2017, 8, 224.
Van Nuffel, A. M.; et al., Intravenous and intradermal TriMix-dendritic cell therapy results in a broad T-cell response and durable tumor response in a chemorefractory stage IV-M1c melanoma patient. Cancer Immunol Immunother 2012, 61 (7), 1033-43.
Wang, N. Y.; et al., The next chapter for group B meningococcal vaccines. Crit Rev Microbiol 2017, 1-17.
Wang, Y.; et al., Effectiveness and practical uses of 23-valent pneumococcal polysaccharide vaccine in healthy and special populations. Hum Vaccin Immunother 2017, 1-10.
Webb, R. P.; et al., Recombinant Botulinum Neurotoxin Hc Subunit (BoNT Hc) and Catalytically Inactive Clostridium botulinum Holoproteins (ciBoNT HPs) as Vaccine Candidates for the Prevention of Botulism. Toxins (Basel) 2017, 9 (9).
Webb, R.P., et al. (2009). Production of catalytically inactive BoNT/A1 holoprotein and comparison with BoNT/A1 subunit vaccines against toxin subtypes A1, A2, and A3. Vaccine 27, 4490-4497.
Webb, R.P., et al. (2013). What next for botulism vaccine development? Expert Rev Vaccines 12, 481-492.
Weisemann, J.; et al., Botulinum Neurotoxin Serotype A Recognizes Its Protein Receptor SV2 by a Different Mechanism than Botulinum Neurotoxin B Synaptotagmin. Toxins (Basel) 2016, 8 (5).
Whitemarsh, R.C., et al. (2012). Novel application of human neurons derived from induced pluripotent stem cells for highly sensitive botulinum neurotoxin detection. Toxicol Sci 126, 426-435.
Whitemarsh, R.C., et al. (2013). Characterization of Botulinum Neurotoxin A Subtypes 1 Through 5 by Investigation of Activities in Mice, Neuronal Cell Cultures, and In Vitro. Infect Immun 81, 3894-3902.

(56) References Cited

OTHER PUBLICATIONS

Woldeamanuel, Y. W., Tetanus in Ethiopia: unveiling the blight of an entirely vaccine-preventable disease. Curr Neurol Neurosci Rep 2012, 12 (6), 655-65.
World Health Organization. (2017). Tetanus vaccines: WHO position paper—Feb. 2017. Weekly Epidemiological Record. 92(6), 53-76.
World Health Organization. Tetanus vaccines: WHO position paper, Feb. 2017—Recommendations. Vaccine 2018, 36 (25), 3573-3575.
Xu, Q., et al. (2009). An adenoviral vector-based mucosal vaccine is effective in protection against botulism. Gene Ther 16, 367-375.
Yu, Y.Z., et al. (2014). Pentavalent replicon vaccines against botulinum neurotoxins and tetanus toxin using DNA-based Semliki Forest virus replicon vectors. Hum Vaccin Immunother 10, 1874-1879.
Zhang, G.L. et al., Synthetic Glycans and Glycomimetics: A Promising Alternative to Natural Polysaccharides. Chemistry 2017.
Zuverink, M.; et al., A Heterologous Reporter Defines the Role of the Tetanus Toxin Interchain Disulfide in Light-Chain Translocation. Infect Immun 2015, 83 (7), 2714-24.
Przedpelski, A., et al. "A novel high-potency tetanus vaccine." Mbio 11.4 (2020): e01668-20.
Ngo et al., "The Protein Folding Problem and Tertiary Structure" Chapter 14, (1994) p. 492-494.
Li, et al., "A Single Mutation in the Recombinant Light Chain of Tetanus Toxin Abolishes Its Proteolytic Activity and Removes the Toxicity Seen after Reconstitution with Native Heavy Chain", Biochemistry, 1994, vol. 33, pp. 7014-7020.
Baum, A., et al., "Antibody cocktail to SARS-CoV-2 spike protein prevents rapid mutational escape seen with individual antibodies" Science (2020) vol. 369, Issue 6506 1014-1018.
Bisht, H., et al., "Neutralizing antibody and protective immunity to SARS coronavirus infection of mice induced by a soluble recombinant polypeptide containing an N-terminal segment of the spike glycoprotein" Virology (2005) 334 (2), 160-5.
Graham, R. L., et al., "A decade after SARS: strategies for controlling emerging coronaviruses" Nat Rev Microbiol (2013) 11 (12), 836-48.
Wrapp, D., et al., "Cryo-EM structure of the 2019-nCoV spike in the prefusion conformation" Science (2020) 367 (6483), 1260-1263.
Chen C, et al., "Molecular basis for tetanus toxin coreceptor interactions" Biochemistry (2008) 47(27):7179-86. doi: 10.1021/bi800640y. Epub Jun. 11, 2008. PMID: 18543947.
Agarwal, R.; et al., Structural analysis of botulinum neurotoxin serotype F light chain: implications on substrate binding and inhibitor design. Biochemistry 2005, 44 (35), 11758-65.
Agnolon, V.; et al., The potential of adjuvants to improve immune responses against TdaP vaccines: A preclinical evaluation of MF59 and monophosphoryl lipid A. Int J Pharm 2015, 492 (1-2), 169-76.
Atassi, M.Z., et al. (2011). Regions of botulinum neurotoxin A light chain recognized by human anti-toxin antibodies from cervical dystonia patients immunoresistant to toxin treatment. The antigenic structure of the active toxin recognized by human antibodies. Immunobiology 216, 782-792.
Baldwin, M.R., et al. (2008). Subunit vaccine against the seven serotypes of botulism. Infect Immun 76, 1314-1318.
Bayart, C., et al. "The combined use of analytical tools for exploring tetanus toxin and tetanus toxoid structures." Journal of Chromatography B 1054 (2017): 80-92.
Berntsson, R. P.; et al., Structure of dual receptor binding to botulinum neurotoxin B. Nat Commun 2013, 4, 2058.
Blum, F. C.; et al., Entry of a recombinant, full-length, atoxic tetanus neurotoxin into Neuro-2a cells. Infect Immun 2014, 82 (2), 873-81.
Blum, F. C.; et al., Multiple domains of tetanus toxin direct entry into primary neurons. Traffic 2014, 15 (10), 1057-65.
Broker, M.; et al., Polysaccharide conjugate vaccine protein carriers as a "neglected valency"—Potential and limitations. Vaccine 2017, 35 (25), 3286-3294.

Burns, J. R. Mechanisms of clostridial neurotoxin binding and entry. Diss. University of Missouri—Columbia, 2016.
Byrne, M.P., et al. (2000). Development of vaccines for prevention of botulism. Biochimie 82, 955-966.
Centers for Disease Control and Prevention (CDC. "Notice of CDC's discontinuation of investigational pentavalent (ABCDE) botulinum toxoid vaccine for workers at risk for occupational exposure to botulinum toxins." MMWR. Morbidity and mortality weekly report 60.42 (2011): 1454.
Centers for Disease Control and Prevention. Impact of vaccines universally recommended for children—United States, 1990-1998. MMWR Morb Mortal Wkly Rep 1999, 48 (12), 243-8.
Centers for Disease Control and Prevention. Thimerosal in vaccines: a joint statement of the American Academy of Pediatrics and the Public Health Service. MMWR Morb Mortal Wkly Rep 1999, 48 (26), 563-5.
Chen, C.; et al., Gangliosides as high affinity receptors for tetanus neurotoxin. J Biol Chem 2009, 284 (39), 26569-77.
Chen, S.; et al., Insights into the different catalytic activities of Clostridium neurotoxins. Biochemistry 2012, 51 (18), 3941-7.
Chen, S.; et al., Mechanism of substrate recognition by botulinum neurotoxin serotype A. J Biol Chem 2007, 282 (13), 9621-7.
Chen, S.; et al., Multiple pocket recognition of SNAP25 by botulinum neurotoxin serotype E. J Biol Chem 2007, 282 (35), 25540-7.
Cheng, L.W., et al. (2009). Antibody protection against botulinum neurotoxin intoxication in mice. Infect Immun 77, 4305-4313.
Chu, C., et al. "Further studies on the immunogenicity of Haemophilus influenzae type b and pneumococcal type 6A polysaccharide-protein conjugates." Infection and Immunity 40.1 (1983): 245-256.
Clapp, B., et al. (2010). Adenovirus F protein as a delivery vehicle for botulinum B. Bmc Immunol 11, 36.
Clayton, M. A.; et al., Protective vaccination with a recombinant fragment of Clostridium botulinum neurotoxin serotype A expressed from a synthetic gene in *Escherichia coli*. Infect Immun 1995, 63 (7), 2738-42.
Cohn, A. C.; et al., Effectiveness and Duration of Protection of One Dose of a Meningococcal Conjugate Vaccine. Pediatrics 2017, 139 (2).
Di Bello, I.C., et al. (1994). Antagonism of the intracellular action of botulinum neurotoxin type A with monoclonal antibodies that map to light-chain epitopes. Eur J Biochem 219, 161-169.
Dolimbek, B.Z., et al. (2007). Mapping of the regions on the heavy chain of botulinum neurotoxin A (BoNT/A) recognized by antibodies of cervical dystonia patients with immunoresistance to BoNT/A. Mol Immunol 44, 1029-1041.
Dolimbek, G. S.; et al., Mapping of the antibody and T cell recognition profiles of the HN domain (residues 449-859) of the heavy chain of botulinum neurotoxin A in two high-responder mouse strains. Immunol Invest 2005, 34 (2), 119-42.
Drake, J. W.; et al., Rates of spontaneous mutation. Genetics 1998, 148 (4), 1667-86.
Dressler, D., Botulinum toxin drugs: brief history and outlook. J Neural Transm (Vienna) 2016, 123 (3), 277-9.
Fan, Y.; et al., A three monoclonal antibody combination potently neutralizes multiple botulinum neurotoxin serotype F subtypes. PLoS One 2017, 12 (3), e0174187.
Feikin, D. R.; et al., Randomized trial of the quantitative and functional antibody responses to a 7-valent pneumococcal conjugate vaccine and/or 23-valent polysaccharide vaccine among HIV-infected adults. Vaccine 2001, 20 (3-4), 545-53.
Fu, Z.; et al., Glycosylated SV2 and gangliosides as dual receptors for botulinum neurotoxin serotype F. Biochemistry 2009, 48 (24), 5631-41.
Garcia-Rodriguez, C., et al. (2011). Neutralizing human monoclonal antibodies binding multiple serotypes of botulinum neurotoxin. Protein Eng Des Sel 24, 321-331.
Gill, D. M., Bacterial toxins: a table of lethal amounts. Microbiol Rev 1982, 46 (1), 86-94.
Gu, S., et al. (2012). Botulinum neurotoxin is shielded by NTNHA in an interlocked complex. Science 335, 977-981.
Guazzelli, L.; et al., Synthesis of part structures of Cryptococcus neoformans serotype C capsular polysaccharide. Carbohydr Res 2016, 433, 5-13.

(56) References Cited

OTHER PUBLICATIONS

Halliwell, G., The action of proteolytic enzymes on Clostridium botulinum type A toxin. Biochem J 1954, 58 (1), 4-8.

Halperin, B. A.; et al., Kinetics of the antibody response to tetanus-diphtheria-acellular pertussis vaccine in women of childbearing age and postpartum women. Clin Infect Dis 2011, 53 (9), 885-92.

Hill, K.K., et al. (2007). Genetic diversity among Botulinum Neurotoxin-producing clostridial strains. Journal of bacteriology 189, 818-832.

International Searching Authority. International Search Report and Written Opinion for application PCT/US2018/066033. Mailed on Jul. 10, 2019. 15 pages.

Isturiz, R. E.; et al., Pneumococcal conjugate vaccine use for the prevention of pneumococcal disease in adults <50 years of age. Expert Rev Vaccines 2017, 1-11.

Jacobson, M.J., et al. (2011). Purification, Modeling and Analysis of Neurotoxin BoNT/A5 from Clostridium botulinum Strain A661222. Applied and Environmental Microbiology.

Johnson, B. D.; et al., Graft-vs.-host and graft-vs.-leukemia reactions after delayed infusions of donor T-subsets. Biol Blood Marrow Transplant 1999, 5 (3), 123-32.

Johnson, E. A., et al. "Botulism." Handbook of clinical neurology 91 (2008): 333-368. (In two parts due to file size).

Keller, J. E., Characterization of new formalin-detoxified botulinum neurotoxin toxoids. Clin Vaccine Immunol 2008, 15 (9), 1374-9.

Killeen, K. P.; et al., Reversion of recombinant toxoids: mutations in diphtheria toxin that partially compensate for active-site deletions. Proc Natl Acad Sci U S A 1992, 89 (13), 6207-9.

Klein, N. P.; et al., Immunogenicity and safety of the Haemophilus influenzae type b and Neisseria meningitidis serogroups C and Y-tetanus toxoid conjugate vaccine co-administered with human rotavirus, hepatitis A and 13-valent pneumococcal conjugate vaccines: results from a phase III, randomized, multicenter study in infants. Hum Vaccin Immunother 2018, 1-12.

Kobayashi, R., et al. (2005). A novel neurotoxoid vaccine prevents mucosal botulism. J Immunol 174, 2190-2195.

Koepke, R.; et al., Global occurrence of infant botulism, 1976-2006. Pediatrics 2008, 122 (1), e73-82.

Kumai, T.; et al., Optimization of Peptide Vaccines to Induce Robust Antitumor CD4 T-cell Responses. Cancer Immunol Res 2017, 5 (1), 72-83.

Lacy, D. B.; et al., Sequence homology and structural analysis of the clostridial neurotoxins. Journal of molecular biology 1999, 291 (5), 1091-104.

C1/S1 - Crude(C1) and Soluble(S1) Lysate in 10mM PO$^4$

C2/S2 - Crude(C2) and Soluble(S2) Lysate in 10mM PO$^4$ and 2% Triton-X100

C3/S3 - Crude(C3) and Soluble(S3) Lysate in 10mM PO$^4$ and 2% Triton-X100 and 4M urea

**2M-TT (TeNTRY) (GenBank X06214.1. modified for optimized expression in *Escherichia coli*)**

MPITINNFRYSDPVNNDTIIMMEPPYCKGLDIYYKAFKITDRIWIVPERYEFGTKPEDFNPPSSLIEGASEYYDPNYLRTDS
DKDRFLQTMVKLFNRIKNNVAGEALLDKIINAIPYLGNSYSLLDKFDTNSNSVSFNLLEQDPSGATTKSAMLTNLIIFGPG
PVLNKNEVRGIVLRVDNKNYFPCRDGFGSIMQMAFCPEYVPTFDNVIENITSLTIGKSKYFQDPALLLMHELIHVLHGLY
GMQVSSHEIIPSKQEIYMQHTYPISAEELFTFGGQDANLISIDIKNDLYEKTLNDYKAIANKLSQVTSCNDPNIDIDSYKQIY
QQKYQFDKDSNGQYIVNEDKFQILYNSIMYGFTEIELGKKFNIKTALSFFSMNHDPVKIPNLLDDTIYNDTEGFNIESKDL
KSEYKGQNMRVNTNAFRNVDGSGLVSKLIGLCKKIIPPTNIRENLYNRTASLTDLGGELCIKIKNEDLTFIAEKNSFSEEPF
QDEIVSYNTKNKPLNFNYSLDKIIVDYNLQSKITLPNDRTTPVTKGIPYAPEYKSNAASTIEIHNIDDNTIYQYLYAQKSPTTL
QRITMTNSVDDALINSTKIYSYFPSVISKVNQGAQGILFLQWVRDIIDDFTNESSQKTTIDKISDVSTIVPYIGPALNIVKQG
YEGNFIGALETTGVVLLLEYIPEITLPVIAALSIAESSTQKEKIIKTIDNFLEKRYEKWIEVYKLVKAKWLGTVNTQFQKRSYQ
MYRSLEYQVDAIKKIIDYEYKIYSGPDKEQIADEINNLKNKLEEKANKAMININIFMRESSRSFLVNQMINEAKKQLLEFDT
QSKNILMQYIKANSKFIGITELKKLESKINKVFSTPIPFSYSKNLDCWVDNEEDIDVILKKSTILNLDINNDIISDISGFNSSVIT
YPDAQLVPGINGKAIHLVNNESSEVIVHKAMDIEYNDMFNNFTVSFWLRVPKVSASHLEQYGTNEYSIISSMKKHSLSIG
SGWSVSLKGNNLIWTLKDSAGEVRQITFRDLPDKFNAYLANKWVFITITNDRLSSANLYINGVLMGSAEITGLGAIREDN
NITLKLDRCNNNNQYVSIDKFRIFCKALNPKEIEKLYTSYLSITFLRDFWGNPLRYDTEYYLIPVASSSKDVQLKNITDYMYL
TNAPSYTNGKLNIYYRRLYNGLKFIIKRYTPNNEIDSFVKSGDFIKLYVSYNNNEHIVGYPKDGNAFNNLDRILRVGYNAP
GIPLYKKMEAVKLRDLKTYSVQLKLYDDKNASLGLVGTHNGQIGNDPNRDILIASNWYFNHLKDKILGCDWYFVPTDEG
WTND

FIG. 7

5MTT

MPITINNFRYSDPVNNDTIIMMEPPYCKGLDIYYKAFKITDRIWIVPERYEFGTKPEDFNPPSSLIEGASEYYDPNYLRTDS
DKDRFLQTMVKLFNRIKNNVAGEALLDKIINAIPYLGNSYSLLDKFDTNSNSVSFNLLEQDPSGATTKSAMLTNLIIFGPG
PVLNKNEVRGIVLRVDNKNYFPCRDGFGSIMQMAFCPEYVPTFDNVIENITSLTIGKSKYFQDPALLLMHQLIHVLHGLY
GMQVSSHEIIPSKQEIYMQHTYPISAEELFTFGGQDANLISIDIKNDLYEKTLNDYKAIANKLSQVTSCNDPNIDIDSYKQIY
QQKYQFDKDSNGQYIVNEDKFQILYNSIMYGFTEIELGKKFNIKTALSFFSMNHDPVKIPNLLDDTIYNDTEGFNIESKDL
KSEYKGQNMRVNTNAFRNVDGSGLVSKLIGLCKKIIPPTNIRENLYNRTASLTDLGGELCIKIKNEDLTFIAEKNSFSEEPF
QDEIVSYNTKNKPLNFNYSLDKIIVDYNLQSKITLPNDRTTPVTKGIPYAPEYKSNAASTIEIHNIDDNTIYQYLYAQKSPTTL
QRITMTNSVDDALINSTKIYSYFPSVISKVNQGAQGILFLQWVRDIIDDFTNESSQKTTIDKISDVSTIVPYIGPALNIVKQG
YEGNFIGALETTGVVLLLEYIPEITLPVIAALSIAESSTQKEKIIKTIDNFLEKRYEKWIEVYKLVKAKWLGTVNTQFQKRSYQ
MYRSLEYQVDAIKKIIDYEYKIYSGPDKEQIADEINNLKNKLEEKANKAMININIFMRESSRSFLVNQMINEAKKQLLEFDT
QSKNILMQYIKANSKFIGITELKKLESKINKVFSTPIPFSYSKNLDCWVDNEEDIDVILKKSTILNLDINNDIISDISGFNSSVIT
YPDAQLVPGINGKAIHLVNNESSEVIVHKAMDIEYNDMFNNFTVSFWLRVPKVSASHLEQYGTNEYSIISSMKKHSLSIG
SGWSVSLKGNNLIWTLKDSAGEVRQITFRDLPDKFNAYLANKWVFITITNDRLSSANLYINGVLMGSAEITGLGAIREDN
NITLKLDRCNNNNQYVSIDKFRIFCKALNPKEIEKLYTSYLSITFLRDFWGNPLRYDTEYYLIPVASSSKDVQLKNITDYMYL
TNAPSYTNGKLNIYYRRLYNGLKFIIKRYTPNNEIDSFVKSGDFIKLYVSYNNNEHIVGYPKDGNAFNNLDRILLVGYNAPG
IPLYKKMEAVKLRDLKTYSVQLKLYDDKNASLGLVGTHNGQIGNDPNRDILIASNAYFNHLKDKILGCDWYFVPTDEGW
TND

FIG. 8

6MTT

MPITINNFRYSDPVNNDTIIMMEPPYCKGLDIYYKAFKITDRIWIVPERYEFGTKPEDFNPPSSLIEGASEYYDPNYLRTDS
DKDRFLQTMVKLFNRIKNNVAGEALLDKIINAIPYLGNSYSLLDKFDTNSNSVSFNLLEQDPSGATTKSAMLTNLIIFGPG
PVLNKNEVRGIVLRVDNKNYFPCRDGFGSIMQMAFCPEYVPTFDNVIENITSLTIGKSKYFQDPALLLMHQLIHVLHGLY
GMQVSSHEIIPSKQEIYMQHTYPISAEELFTFGGQDANLISIDIKNDLYEKTLNDYKAIANKLSQVTSCNDPNIDIDSYKQIY
QQKYQFDKDSNGQYIVNEDKFQILYNSIMYGFTEIELGKKFNIKTALSFFSMNHDPVKIPNLLDDTIYNDTEGFNIESKDL
KSEYKGQNMRVNTNAFRNVDGSGLVSKLIGLCKKIIPPTNIRENLYNRTASLTDLGGELCIKIKNEDLTFIAEKNSFSEEPF
QDEIVSYNTKNKPLNFNYSLDKIIVDYNLQSKITLPNDRTTPVTKGIPYAPEYKSNAASTIEIHNIDDNTIYQYLYAQKSPTTL
QRITMTNSVDDALINSTKIYSYFPSVISKVNQGAQGILFLQWVRDIIDDFTNESSQKTTIDKISDVSTIVPYIGPALNIVKQG
YEGNFIGALETTGVVLLLEYIPEITLPVIAALSIAESSTQKEKIIKTIDNFLEKRYEKWIEVYKLVKAKWLGTVNTQFQKRSYQ
MYRSLEYQVDAIKKIIDYEYKIYSGPDAEQIADEINNLKNKLEEKANKAMININIFMRESSRSFLVNQMINEAKKQLLEFDT
QSKNILMQYIKANSKFIGITELKKLESKINKVFSTPIPFSYSKNLDCWVDNEEDIDVILKKSTILNLDINNDIISDISGFNSSVIT
YPDAQLVPGINGKAIHLVNNESSEVIVHKAMDIEYNDMFNNFTVSFWLRVPKVSASHLEQYGTNEYSIISSMKKHSLSIG
SGWSVSLKGNNLIWTLKDSAGEVRQITFRDLPDKFNAYLANKWVFITITNDRLSSANLYINGVLMGSAEITGLGAIREDN
NITLKLDRCNNNNQYVSIDKFRIFCKALNPKEIEKLYTSYLSITFLRDFWGNPLRYDTEYYLIPVASSSKDVQLKNITDYMYL
TNAPSYTNGKLNIYYRRLYNGLKFIIKRYTPNNEIDSFVKSGDFIKLYVSYNNNEHIVGYPKDGNAFNNLDRILLVGYNAPG
IPLYKKMEAVKLRDLKTYSVQLKLYDDKNASLGLVGTHNGQIGNDPNRDILIASNAYFNHLKDKILGCDWYFVPTDEGW
TND

FIG. 9

7MTT

MPITINNFRYSDPVNNDTIIMMEPPACKGLDIYYKAFKITDRIWIVPERYEFGTKPEDFNPPSSLIEGASEYYDPNYLRTDS
DKDRFLQTMVKLFNRIKNNVAGEALLDKIINAIPYLGNSYSLLDKFDTNSNSVSFNLLEQDPSGATTKSAMLTNLIIFGPG
PVLNKNEVRGIVLRVDNKNYFPCRDGFGSIMQMAFCPEYVPTFDNVIENITSLTIGKSKYFQDPALLLMHQLIHVLHGLY
GMQVSSHEIIPSKQEIYMQHTYPISAEELFTFGGQDANLISIDIKNDLYEKTLNDYKAIANKLSQVTSCNDPNIDIDSYKQIY
QQKYQFDKDSNGQYIVNEDKFQILYNSIMYGFTEIELGKKFNIKTALSFFSMNHDPVKIPNLLDDTIYNDTEGFNIESKDL
KSEYKGQNMRVNTNAFRNVDGSGLVSKLIGLCKKIIPPTNIRENLYNRTASLTDLGGELCIKIKNEDLTFIAEKNSFSEEPF
QDEIVSYNTKNKPLNFNYSLDKIIVDYNLQSKITLPNDRTTPVTKGIPYAPEYKSNAASTIEIHNIDDNTIYQYLYAQKSPTTL
QRITMTNSVDDALINSTKIYSYFPSVISKVNQGAQGILFLQWVRDIIDDFTNESSQKTTIDKISDVSTIVPYIGPALNIVKQG
YEGNFIGALETTGVVLLLEYIPEITLPVIAALSIAESSTQKEKIIKTIDNFLEKRYEKWIEVYKLVKAKWLGTVNTQFQKRSYQ
MYRSLEYQVDAIKKIIDYEYKIYSGPDAEQIADEINNLKNKLEEKANKAMININIFMRESSRSFLVNQMINEAKKQLLEFDT
QSKNILMQYIKANSKFIGITELKKLESKINKVFSTPIPFSYSKNLDCWVDNEEDIDVILKKSTILNLDINNDIISDISGFNSSVIT
YPDAQLVPGINGKAIHLVNNESSEVIVHKAMDIEYNDMFNNFTVSFWLRVPKVSASHLEQYGTNEYSIISSMKKHSLSIG
SGWSVSLKGNNLIWTLKDSAGEVRQITFRDLPDKFNAYLANKWVFITITNDRLSSANLYINGVLMGSAEITGLGAIREDN
NITLKLDRCNNNNQYVSIDKFRIFCKALNPKEIEKLYTSYLSITFLRDFWGNPLRYDTEYYLIPVASSSKDVQLKNITDYMYL
TNAPSYTNGKLNIYYRRLYNGLKFIIKRYTPNNEIDSFVKSGDFIKLYVSYNNNEHIVGYPKDGNAFNNLDRILLVGYNAPG
IPLYKKMEAVKLRDLKTYSVQLKLYDDKNASLGLVGTHNGQIGNDPNRDILIASNAYFNHLKDKILGCDWYFVPTDEGW
TND

FIG. 10

8MTT

MPITINNFRYSDPVNNDTIIMMEPPACKGLDIYYKAFKITDRIWIVPERYEFGTKPEDFNPPSSLIEGASEYYDPNYLRTDS
DKDRFLQTMVKLFNRIKNNVAGEALLDKIINAIPYLGNSYSLLDKFDTNSNSVSFNLLEQDPSGATTKSAMLTNLIIFGPG
PVLNKNEVRGIVLRVDNKNYFPCRDGFGSIMQMAFCPEYVPTFDNVIENITSLTIGKSKYFQDPALLKMHQLIHVLHGLY
GMQVSSHEIIPSKQEIYMQHTYPISAEELFTFGGQDANLISIDIKNDLYEKTLNDYKAIANKLSQVTSCNDPNIDIDSYKQIY
QQKYQFDKDSNGQYIVNEDKFQILYNSIMYGFTEIELGKKFNIKTALSFFSMNHDPVKIPNLLDDTIYNDTEGFNIESKDL
KSEYKGQNMRVNTNAFRNVDGSGLVSKLIGLCKKIIPPTNIRENLYNRTASLTDLGGELCIKIKNEDLTFIAEKNSFSEEPF
QDEIVSYNTKNKPLNFNYSLDKIIVDYNLQSKITLPNDRTTPVTKGIPYAPEYKSNAASTIEIHNIDDNTIYQYLYAQKSPTTL
QRITMTNSVDDALINSTKIYSYFPSVISKVNQGAQGILFLQWVRDIIDDFTNESSQKTTIDKISDVSTIVPYIGPALNIVKQG
YEGNFIGALETTGVVLLLEYIPEITLPVIAALSIAESSTQKEKIIKTIDNFLEKRYEKWIEVYKLVKAKWLGTVNTQFQKRSYQ
MYRSLEYQVDAIKKIIDYEYKIYSGPDAEQIADEINNLKNKLEEKANKAMININIFMRESSRSFLVNQMINEAKKQLLEFDT
QSKNILMQYIKANSKFIGITELKKLESKINKVFSTPIPFSYSKNLDCWVDNEEDIDVILKKSTILNLDINNDIISDISGFNSSVIT
YPDAQLVPGINGKAIHLVNNESSEVIVHKAMDIEYNDMFNNFTVSFWLRVPKVSASHLEQYGTNEYSIISSMKKHSLSIG
SGWSVSLKGNNLIWTLKDSAGEVRQITFRDLPDKFNAYLANKWVFITITNDRLSSANLYINGVLMGSAEITGLGAIREDN
NITLKLDRCNNNNQYVSIDKFRIFCKALNPKEIEKLYTSYLSITFLRDFWGNPLRYDTEYYLIPVASSSKDVQLKNITDYMYL
TNAPSYTNGKLNIYYRRLYNGLKFIIKRYTPNNEIDSFVKSGDFIKLYVSYNNNEHIVGYPKDGNAFNNLDRILLVGYNAPG
IPLYKKMEAVKLRDLKTYSVQLKLYDDKNASLGLVGTHNGQIGNDPNRDILIASNAYFNHLKDKILGCDWYFVPTDEGW
TND

FIG. 11

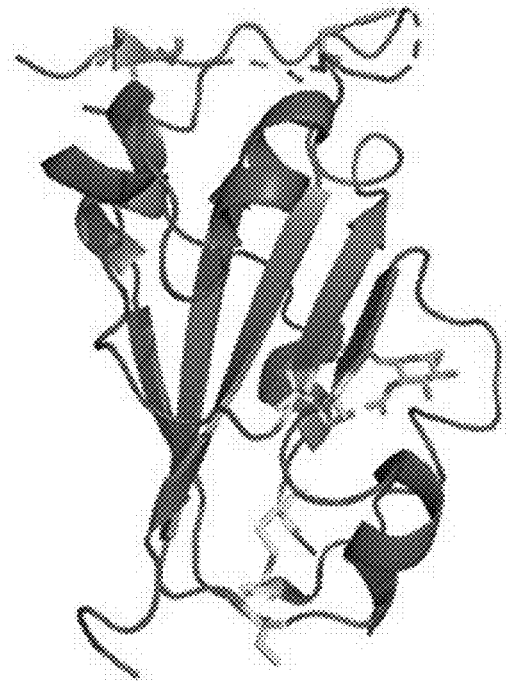

FIG. 12

```
              8MTT              | RBD(433-524)
```

8MTT(RBD433-524)

```
            Y L E R Y S—S   K              R W
HIS6 |3xFlag|   LC   |   HCN   |   HCC   |RBD(433-524)|Strep
```

COVID-19 VACCINE

CROSS-REFERENCE TO RELATED APPLICATIONS

This application claims priority to U.S. Provisional Applications Nos. 62/994,081 filed on Mar. 24, 2020 and 63/104,360 filed on Oct. 22, 2020, the contents of which are incorporated by reference in their entireties.

STATEMENT REGARDING FEDERALLY SPONSORED RESEARCH

This invention was made with government support under grants AI118389 and AI030162, awarded by the National Institutes of Health. The government has certain rights in the invention.

REFERENCE TO A SEQUENCE LISTING SUBMITTED VIA EFS-WEB

A Sequence Listing accompanies this application and is submitted as an ASCII text file of the sequence listing named "650053_00784_ST25.txt" which is 99.1 KB in size and was created on Mar. 23, 2021. The sequence listing is electronically submitted via EFS-Web with the application and is incorporated herein by reference in its entirety.

BACKGROUND

Coronavirus disease 2019 (COVID-19) is a contagious disease caused by severe acute respiratory syndrome coronavirus 2 (SARS-COV-2), a β-Coronavirus, in the family with Severe Acute Respiratory Syndrome (SARS) and Middle East Respiratory Syndrome (MERS) viruses. Studies from the SARS coronavirus identified the role for the spike(S) protein and, more specifically, the receptor binding domain (RBD) in the viral protein response for host cell binding. Recently, the cryo-EM of the spike protein was solved revealing the structure of the RBD. Aligning the amino acid sequence of the spike protein with the structure showed that amino acids 330-521 comprise the RBD (CRBD) of SARS-COV-2.

As the pandemic threat of COVID-19 grows, a need exists for improved COVID-19 vaccination platforms.

SUMMARY OF THE INVENTION

In a first aspect, provided herein is a fusion protein comprising (i) a modified tetanus toxin (MTT) polypeptide comprising a sequence having at least 95% identity to SEQ ID NO:1, having a mutation at each of positions R372 and Y375, and having a mutation at two or more positions selected from E234, K768, R1226, and W1289, wherein each position is numbered relative to SEQ ID NO:1, the MTT polypeptide having reduced toxicity and receptor binding compared to the toxicity and receptor binding of SEQ ID NO:1; and (ii) a SARS-COV-2 spike protein receptor binding domain (CRBD) polypeptide comprising a sequence having at least 95% identity to SEQ ID NO:3.

In some embodiments, the MTT polypeptide and the CRBD polypeptide are connected by a linker polypeptide. In some embodiments, the linker polypeptide is a poly-glycine sequence.

In some embodiments, the MTT polypeptide and the CRBD polypeptide are chemically cross-linked.

In some embodiments, in the MTT polypeptide amino acid R at position R372 is replaced with amino acid A, and wherein amino acid Y at position Y375 is replaced with amino acid F. In some embodiments, the MTT polypeptide mutations comprise R372A, Y375F, E234Q, R1226L, and W1289A. In some embodiments, the MTT polypeptide comprises SEQ ID NO:5. In some embodiments, the MTT polypeptide mutations comprise R372A, Y375F, E234Q, K768A, R1226L, and W1289A. In some embodiments, the MTT polypeptide comprises SEQ ID NO:6. In some embodiments, the MTT polypeptide further comprises a mutation at one or both of positions L230 and Y26, wherein each position is numbered relative to SEQ ID NO:1. In some embodiments, the mutations at one or both of positions L230 and Y26 comprise L230K and Y26A. In some embodiments, the MTT polypeptide comprises SEQ ID NO:7 or SEQ ID NO:8. In some embodiments, the fusion protein comprises a sequence at least 95% identical to SEQ ID NO:10.

In a second aspect, provided herein is a polynucleotide encoding a CRBD-MTT fusion protein as described herein. In some embodiments, the polynucleotide comprises a sequence at least 95% identical to SEQ ID NO:9.

In a third aspect, provided herein is a vector comprising the polynucleotide of claim 14.

In a forth aspect, provided herein is a method for producing a CRBD-MTT fusion protein comprising expressing in a cell a polynucleotide encoding a CRBD-MTT fusion protein as described herein and isolating the CRBD-MTT fusion protein from the cell, whereby the CRBD-MTT fusion protein is produced.

In a fifth aspect, provided herein is a composition comprising a CRBD-MTT fusion protein as described herein and a pharmaceutically acceptable carrier.

In a sixth aspect, provided herein is a method of reducing the risk of a subject developing COVID-19 by inducing an immune response through administering to the subject a therapeutically effective amount of a CRBD-MTT fusion protein as described herein.

In a seventh aspect, provided herein is a use of a CRBD-MTT fusion protein as described herein as a vaccine.

In an eighth aspect, provided herein is a method for producing a CRBD-MTT chemically cross-linked fusion protein comprising obtaining a polypeptide composition comprising (i) a modified tetanus toxin (MTT) polypeptide comprising a sequence having at least 95% identity to SEQ ID NO:1, having a mutation at each of positions R372 and Y375, and having a mutation at two or more positions selected from E234, K768, R1226, and W1289, wherein each position is numbered relative to SEQ ID NO:1, and (ii) a SARS-COV-2 spike protein receptor binding domain (CRBD) polypeptide comprising a sequence having at least 95% identity to SEQ ID NO:3 and contacting the polypeptide composition with a crosslinking agent for a time and under conditions sufficient to chemically crosslink the CRBD polypeptide and the MTT polypeptide; whereby a CRBD-MTT chemically crosslinked fusion protein is produced. In some embodiments, the crosslinking agent is selected from the group consisting of formaldehyde, disuccinimidyl suberate (DSS), succinimidyl-4-(N-maleimidomethyl)cyclohexane-1-carboxylate (SMCC), ethylene glycol bis(sulfosuccinimidylsuccinate) (Sulfo-EGS), bis(sulfosuccinimidyl) suberate (BS3), and dithiobis(succinimidylpropionate) (DSP).

BRIEF DESCRIPTION OF DRAWINGS

The patent or patent application file contains at least one drawing in color. Copies of this patent or patent application

Figure 5:
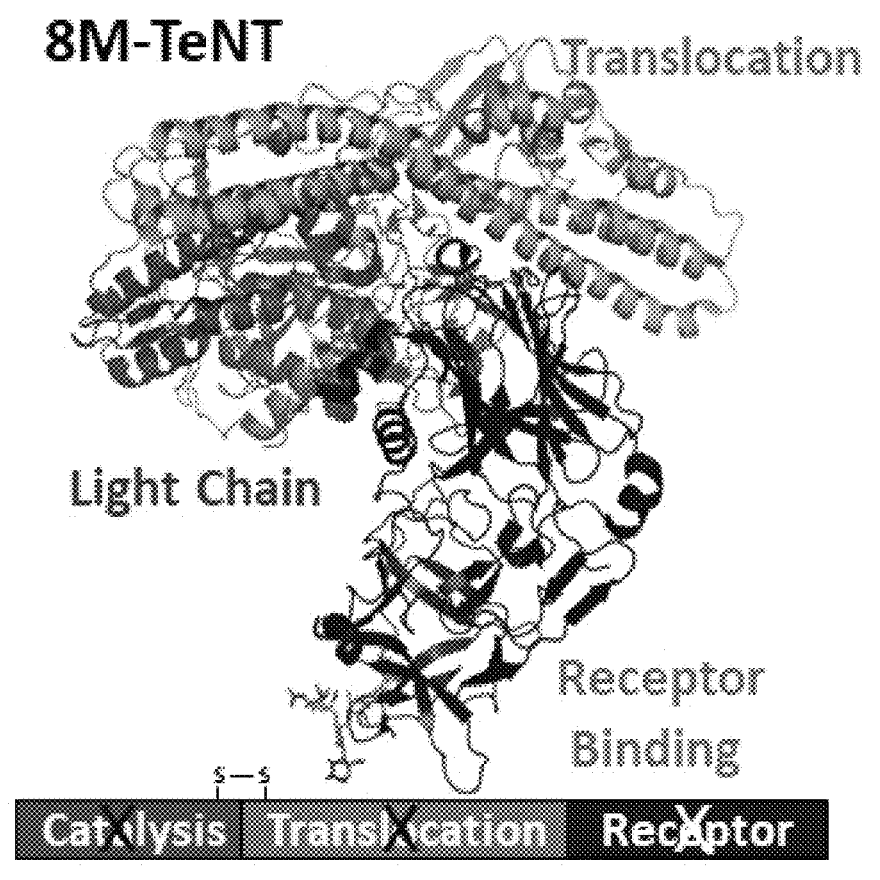

FIG. 5 shows is a crystal structure of TeNTRY PDB:5n0b. Four TT functions were inactivated: Light Chain E234Q, R373A, Y376F ($Zn^{++}$ binding), L230K (VAMP-2 cleavage) and Y26A (VAMP-2 binding), K768A (LC translocation), and R1226L and W1289A (receptor binding).

FIG. 6 is the amino acid sequence of 2MTT (SEQ ID NO:4).

FIG. 7 is the amino acid sequence of 5MTT (SEQ ID NO:5).

FIG. 8 is the amino acid sequence of 6MTT (SEQ ID NO:6).

FIG. 9 is the amino acid sequence of 7MTT (SEQ ID NO:7).

FIG. 10 is the amino acid sequence of 8MTT (SEQ ID NO:8).

FIG. 11 shows the structure of the SARS-COV-2 RBD ("CRBD"), corresponding to amino acids 330-525 of the SARS-COV-2 spike protein (see SEQ ID NO:2). Amino acids indicated in green are the ACE2 binding motif shared with the related SARS virus spike protein.

FIG. 12 presents schematic illustrations of fusion proteins comprising 8MTT and RBD(433-524), which is a portion of the SARS-COV-2 spike protein's receptor binding domain (corresponding to amino acids 330-525 of SEQ ID NO:2).

INCORPORATION BY REFERENCE

Figure 1:
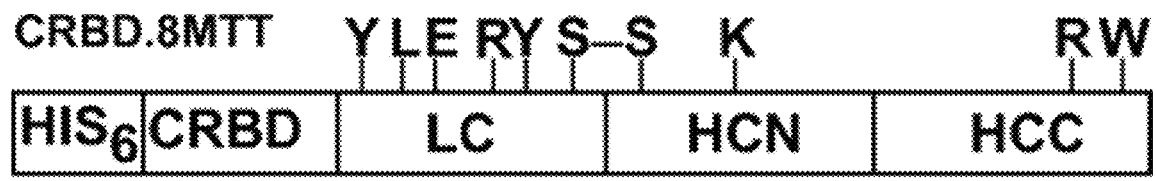
FIG. 1 shows the schematic of the CRBD-8MTT polypeptide.

All publications, patents, and patent applications mentioned in this specification are herein incorporated by reference to the same extent as if each individual publication, patent, and patent application was specifically and individually indicated to be incorporated by reference.

DETAILED DESCRIPTION OF THE INVENTION

The present invention has been described in terms of one or more preferred embodiments, and it should be appreciated that many equivalents, alternatives, variations, and modifications, aside from those expressly stated, are possible and within the scope of the invention.

SARS-COV-2 antigenic polypeptides of the present disclosure comprise the SARS-COV-2 spike protein receptor binding domain (RBD) polypeptide or a portion thereof and a genetically modified tetanus toxin comprising genetic modifications at multiple targets relative to a wild-type toxin, where such modifications eliminate residual toxicity and enhance safety, which will be expanded upon below. Inventor's previous work determined that immune cells take up a non-catalytic, non-receptor binding form of tetanus toxin and mount a similar neutralizing immune response as observed with catalytic tetanus toxin. See WO2019118974, which is incorporated herein by reference in its entirety. Described herein is use of the inactivated tetanus toxin conjugate vaccine platform to produce tetanus toxin-CRBD fusion proteins. The tetanus toxin-CRBD fusion proteins can be used for eliciting an immune response to SARS-Cov-2 spike.

The SARS-COV-2 spike protein sequence is provided herein as SEQ ID NO:2. The SARS-COV-2 receptor binding domain (CRBD) is residues 330-521 of the spike protein and is provided herein as SEQ ID NO:3.

Provided herein are SARS-COV-2 antigenic fusion proteins including the CRBD polypeptide, or a polypeptide with a sequence at least 90%, 95%, 98%, or 99% sequence identity thereto, and a modified tetanus toxin (MTT) with reduced toxicity.

In some cases, a SARS-COV-2 antigenic fusion protein comprises RBD(376-525) or RBD(433-524), which refer to portions of the receptor binding domain (amino acids 330-525) of the SARS-COV-2 spike protein. In some cases, the SARS-COV-2 antigenic fusion protein can comprise RBD (433-524) and a genetically modified tetanus toxin comprising genetic modifications at multiple targets relative to a wild-type toxin. For example, in some cases, the SARS-COV-2 antigenic fusion protein is 8MTT(RBD376-525). In other cases, the SARS-COV-2 antigenic fusion protein can comprise RBD(433-524) and a genetically modified tetanus toxin comprising genetic modifications at multiple targets relative to a wild-type toxin. For example, in other cases, the SARS-COV-2 antigenic fusion protein is 8MTT(RBD433-524) (see FIG. 12). RBD(433-524) contains the binding sites for several monoclonal antibodies (REGN10987 and REGN10933) that complementarily neutralize SARS-COV-2 infections in cultured cells. As described herein, 8MTT (RBD433-524) reacts with antisera to the RBD of the SARS-COV-2 spike protein, and is a soluble protein when produced in E. coli, which suggests it is particularly well suited for use as a vaccine.

In some embodiments, in the CRBD-MTT fusion protein, the CRBD polypeptide is linked to the MTT using a spacer moiety employed as spacer arm bridge between the MTT and CRBD polypeptide. The spacer moiety can be any of a wide variety of molecular structures including, without limitation, dextran, polyglutamic acid, and oligopeptides.

In some embodiments, the spacer is a linker polypeptide. Suitable linker polypeptide sequences are known in the art. In some embodiments, the linker polypeptide is a polyglycine sequence. In some embodiments, the linker polypeptide is a poly-alanine sequence. The linker polypeptide sequence can be from about 2-20 amino acids, preferably glycines, alanines, or combinations thereof. Other amino acids are contemplated and can be used for the linker sequences.

In some embodiments, the CRBD-MTT fusion proteins, the CRBD polypeptide and the MTT polypeptide are linked using chemical crosslinking. Suitable chemical crossing reactions and methods are known and described in the art. The chemical crosslinking reaction may target amine, sulfhydryl, carboxyl, carbonyl, hydroxyl functional groups, or combinations thereof, within the CRBD and MTT polypeptides. In some embodiments, the CRBD and the MTT polypeptides are crosslinked by reacting with a crosslinking agent. As used herein, "crosslinking agent" refers to a compound or group of compounds that when reacted under suitable conditions chemically crosslink functional groups of a polypeptide. Suitable crosslinking agents include, without limitation, formaldehyde, disuccinimidyl suberate (DSS), succinimidyl-4-(N-maleimidomethyl)cyclohexane-1-carboxylate (SMCC), ethylene glycol bis(sulfosuccinimidylsuccinate) (Sulfo-EGS), bis(sulfosuccinimidyl) suberate (BS3), and dithiobis(succinimidylpropionate) (DSP).

As used herein, "toxin" refers to a noxious or poisonous substance (e.g., a cytotoxin) that is formed or elaborated either as an integral part of a cell or tissue (endotoxin), as an intracellular or extracellular product (exotoxin), or as a combination thereof, during the metabolism and growth of certain microorganisms. As used herein, the term "modified toxin" refers to a non-catalytic, non-toxic variant form of a toxin, wherein the toxin is rendered non-catalytic and non-toxic by genetically engineered (e.g., non-naturally occurring, man-made) modifications to the amino acid sequence of the polypeptide toxin. In exemplary embodiments, modified toxins are genetically engineered or otherwise modified variants of a toxin produced by a bacterium of the genus *Clostridium* (e.g., *C. difficile*, *C. novyi*, *C. sordellii*, *C. perfringens*, *C. tetani*, and *C. botulinum*). The toxins may be recombinant, synthetic, part of a fusion protein (which includes, e.g., an antigen, or a polypeptide (e.g., $His_6$) which facilitates purification of the fusion protein), covalently conjugated to an antigen, and/or chemically cross-linked to an antigen. In some cases, non-catalytic, non-toxic forms of toxins are referred to as toxoids. Toxoids lack toxicity but retain their antigenicity and their immunizing capacity.

A tetanus toxin modified as described herein exhibits one or more altered properties as compared to the wild-type tetanus toxin polypeptide shown in SEQ ID NO:1, for example, significantly decreased catalytic activity and receptor binding activity. In some embodiments, the modified tetanus toxins described herein are at least 1,000,000 times less toxic than wild-type tetanus toxin.

As used herein, the term "reduced toxicity" means that, relative to a first composition comprising a particular protein active ingredient (e.g., wild-type TT), a second composition comprising a modified version of a particular protein active ingredient can be administered to a mammal at a dose level which is the same or greater than what is a fatal for the first composition but without death resulting to the mammal. Reduced toxicity encompasses partially or completely eliminated toxicity as detectable by methods known to those who practice in the art. In addition, reduced toxicity encompasses reduced systemic toxicity (i.e., upon intravenous administration) or reduced toxicity upon intramuscular administration.

In some embodiments, the MTT has mutations at amino acid residues 372 and 375, and further having a mutation at one or more of residues 234, 1226, and 1289, where the residue positions are numbered relative to the full-length wild-type tetanus neurotoxin (*Clostridium tetani* CN3911; GenBank accession no. X06214) set forth as SEQ ID NO:1. In certain embodiments, the amino acid mutations at residues 372 and 375 are R372A and Y375F, and the modified toxin further comprises at least one mutation selected from E234Q, R1226L, and W1289A. In some cases, the modified toxin comprises five mutations (R372A, Y375F, E234Q, R1226L, and W1289A) numbered relative to SEQ ID NO:1 and is referred to herein as "5M-TeNT" or "5MTT." See Table 1. In some embodiments, 5M-TeNT comprises the amino acid sequence set forth as SEQ ID NO:5.

TABLE 1

Exemplary mutations for inactivating multiple independent TT functions

|  |  | Function | Zn++ binding | Substrate Binding & catalysis | Light Chain translocation | Ganglioside receptor binding |
|---|---|---|---|---|---|---|
|  |  | Function relevant mutations | E234Q, R372A, Y375F (TT(R372A, Y375F, 2MTT) is 125,000-fold less toxic than native TT[42] | Y26A, L230K |  K768A Inhibits LC translocation (preliminary data) | R1226L, W1289A This mutation is ~800-fold less toxic than TT WT |
| MTT constructs | 2MTT | R372A, Y375F |  |  |  |  |
|  | 5MTT | E234Q, R372A, Y375F |  |  |  | R1226L, W1289A |
|  | 6MTT | E234Q, R372A, Y375F |  |  | K768A (or D767A or E769A) | R1226L, W1289A |
|  | 7MTT | E234Q, R372A, Y375F |  | L230K | K768A (or D767A or E769A) | R1226L, W1289A |
|  | 8MTT | E234Q, R372A, Y375F | Y26A, L230K |  | K768A (or D767A or E769A) | R1226L, W1289A |

Wild-type *Clostridium tetani* CN3911 tetanus toxin is shown in SEQ ID NO:1.

In some embodiments, the tetanus toxin has a modified translocation domain. For example, the lysine (K) residue at position 768 is located within a loop that connects two long alpha helices. Mutation of this single amino acid to an alanine (A) inactivates or blocks light chain translocation. In some cases, the K768A mutation is added to 5MTT modified toxin to produce 6MTT, whereby the resulting modified tetanus toxins comprises independent mutations at six positions (see Tables 2 and 3). In some cases, the modified toxin comprises six mutations (R372A, Y375F, E234Q, K768A, R1226L, and W1289A) numbered relative to SEQ ID NO:1 and is referred to herein as "6M-TeNT" or "6MTT." In some cases, 6M-TeNT comprises the amino acid sequence set forth as SEQ ID NO:6. Without being bound by any particular mechanism or theory, vaccine potency of 6MTT is expected to be higher than 5MTT but should have a lower rate of reversion than 5MTT. The addition of a mutation at one or more of D767, K768, or E769A to 5MTT will yield more complete inactivation of the genetically engineered vaccine by inactivating a function of the translocation domain in addition to disrupted functionality of the catalytic and receptor binding domains.

In some embodiments, the tetanus toxin has been modified to inhibit VAMP-2 cleavage. For example, mutation of the leucine residue at position 230 (for example, mutation of the leucine to a lysine (K)) inactivates the toxin's catalytic activity for VAMP-2 cleavage. In some cases, the L230K mutation is added to 6MTT modified toxin to produce 7MTT, whereby the resulting modified tetanus toxins comprises independent mutations at seven positions (Table 3). In some cases, the modified toxin comprises eight independent mutations (R372A, Y375F, E234Q, R1226L, W1289A, K768A, and L230K) numbered relative to SEQ ID NO:1 and is referred to herein as "7M-TeNT" or "7MTT." In some cases, 7M-TeNT comprises the amino acid sequence set forth as SEQ ID NO:7.

In some embodiments, the tetanus toxin has been modified to inhibit VAMP-2 binding. For example, mutation of the tyrosine (Y) residue at position 26 (for example, mutation of the tyrosine to an alanine (A)) inactivates VAMP-2 binding capacity of the toxin. In some cases, the Y26A mutation is added to 7MTT modified toxin to produce 8MTT, whereby the resulting modified tetanus toxins comprises independent mutations at eight positions (Table 3). In some cases, the modified toxin comprises eight independent mutations (R372A, Y375F, E234Q, R1226L, W1289A, K768A, L230K, and Y26A) numbered relative to SEQ ID NO: 1 and is referred to herein as "8M-TeNT" or "8MTT." In some embodiments, 8M-TeNT comprises the amino acid sequence set forth as SEQ ID NO:8.

Advantageously, modified tetanus toxins of this disclosure do not require detoxification with formalin for use as a vaccine or adjuvant. In some cases, small quantities of formalin (~0.04%) or another fixative or stabilizing reagent (e.g., formalin, glutaraldehyde, β-propiolactone and the like) are added to the modified tetanus toxin as a stabilizing agent, but such quantities are smaller (e.g., smaller by an order of magnitude) than those generally used (~0.4%) to detoxify wild-type tetanus toxin (or tetanus toxin not modified as described herein) to form "tetanus toxoid."

In some cases, the modified tetanus toxin comprises other amino acid substitutions at residue positions 372, 375, 234, 768, 1226, 1289, 230, and/or 26. For example, amino acids that may substitute for the listed amino acids include substitutions that reverse the charge or hydrophobicity reversal of the original residue, conservative amino acid substitutions, and substitutions that delete the original residue.

As is well known to those skilled in the art, altering the primary structure of a polypeptide by a conservative amino acid substitution may not significantly alter the activity of that polypeptide because the side-chain of the amino acid which is inserted into the sequence may be able to form similar bonds and contacts as the side chain of the amino acid which has been substituted out. This is so even when the substitution is in a region critical in determining the polypeptide's conformation.

Conservative amino acid substitutions are art recognized substitutions of one amino acid for another amino acid having similar characteristics. Conservative amino acid substitutions may be achieved by modifying a nucleotide sequence to introduce a nucleotide change that will encode the conservative substitution. For example, each amino acid may be described as having one or more of the following characteristics: electropositive, electronegative, aliphatic, aromatic, polar, hydrophobic and hydrophilic. Conservative substitutions include substitution among amino acids within each group. Acidic amino acids include aspartate, glutamate. Basic amino acids include histidine, lysine, arginine; aliphatic amino acids include isoleucine, leucine and valine. Aromatic amino acids include phenylalanine, glycine, tyrosine and tryptophan. Polar amino acids include aspartate, glutamate, histidine, lysine, asparagine, glutamine, arginine, serine, threonine and tyrosine. Hydrophobic amino acids include alanine, cysteine, phenylalanine, glycine, isoleucine, leucine, methionine, proline, valine and tryptophan. Amino acids may also be described in terms of relative size, where alanine, cysteine, aspartate, glycine, asparagine, proline, threonine, serine, valine, are considered to be small.

In some cases, non-conservative substitutions are possibly provided if these substitutions do not disrupt the tertiary structure of an epitope within the polypeptide, for example, which do not interrupt the immunogenicity (for example, the antigenicity) of the polypeptide and do not restore toxicity.

The terms "polypeptide," "peptide," and "protein," as used herein, refer to a polymer comprising amino acid residues predominantly bound together by covalent amide bonds. By the term "protein," we mean to encompass all the above definitions. The terms apply to amino acid polymers in which one or more amino acid residue may be an artificial chemical mimetic of a naturally occurring amino acid, as well as to naturally occurring amino acid polymers and non-naturally occurring amino acid polymers. As used herein, the terms may encompass amino acid chains of any length, including full length proteins, wherein the amino acids are linked by covalent peptide bonds. The protein or peptide may be isolated from a native organism, produced by recombinant techniques, or produced by synthetic production techniques known to one skilled in the art.

Sequence identity between amino acid sequences can be determined by comparing an alignment of the sequences. When an equivalent position in the compared sequences is occupied by the same amino acid, then the molecules are identical at that position. Scoring an alignment as a percentage of identity is a function of the number of identical amino acids at positions shared by the compared sequences. When comparing sequences, optimal alignments may require gaps to be introduced into one or more of the sequences, to take into consideration possible insertions and deletions in the sequences. Sequence comparison methods may employ gap penalties so that, for the same number of identical molecules in sequences being compared, a sequence alignment with as few gaps as possible, reflecting higher relatedness between the two compared sequences, will achieve a higher score than one with many gaps. Calculation of maximum percent identity involves the production of an optimal alignment, taking into consideration gap penalties. As mentioned above, the percentage sequence identity may be determined using the Needleman-Wunsch Global Sequence Alignment tool, publicly available at blast.ncbi.nlm.nih.gov/Blast.cgi, using default parameter settings. The Needleman-Wunsch algorithm was published in *J. Mol. Biol.* (1970) vol. 48:443-53.

Polypeptides and nucleic acids of the invention may be prepared synthetically using conventional synthesizers. Alternatively, they may be produced using recombinant DNA technology and may be incorporated into suitable expression vector, which is then used to transform a suitable host cell, such as a prokaryotic cell such as *E. coli*. The transformed host cells are cultured and the polypeptide isolated therefrom.

Provided herein are nucleic acid sequences which code for the CRBD-MTT fusion proteins and other nucleic acid sequence which hybridize to a nucleic molecule consisting of the above-described nucleotide sequences under high stringency conditions. In a particular-embodiment provided herein are DNA sequences encoding CRBD-MTT fusion proteins with the modified tetanus toxin having mutations at amino acid residues 372 and 375, and further comprises a mutation at one or more of residues 234, 1226, and 1289 or the modified catalytic domain described herein.

The term "stringent conditions" as used herein refers to parameters with which the art is familiar. For example, nucleic acid hybridization parameters may be found in references which compile such methods, e.g., *Molecular Cloning: A Laboratory Manual*, J. Sambrook, et al., eds., Second Edition, Cold Spring Harbor Laboratory Press, Cold Spring Harbor, New York, 1989, or *Current Protocols in Molecular Biology*, F. M. Ausubel, et al., eds., John Wiley & Sons, Inc., New York. More specifically, high stringency conditions as used herein, refers to hybridization at 65° C. in hybridization buffer (3.5×SSC, 0.02% Ficoll, 0.02% Polyvinyl pyrolidone, 0.02% Bovine Serum Albumin, 25 mM $NaH_2PO_4$ (pH 7), 0.5% SDS, 2 mM EDTA). SSC is 0.15M Sodium Chloride/0.015M Sodium Citrate, pH 7; SDS is Sodium Dodecyl Sulphate; and EDTA is Ethylene diaminetetraacetic acid. After hybridization, the membrane upon which the DNA is transferred is washed at 2×SSC at room temperature and then at 0.1-0.5×SSC/0.1×SDS at temperatures up to 68° C., e.g., 55° C., 60° C., 65° C. or 68° C. Alternatively, high stringency hybridization may be performed using a commercially available hybridization buffer, such as ExpressHyb™ buffer (Clontech) using hybridization and washing conditions described by the manufacturer.

It will also be understood that the invention embraces the use of the sequences in expression vectors, as well as to transfect host cells and cell lines, be these prokaryotic (e.g. *E. coli*), or eukaryotic (e.g., dendritic cells, CHO cells, COS cells, yeast expression systems, recombinant baculovirus expression in insect cells). The expression vectors require that the pertinent sequence, i.e., those described supra, be operably linked to a promoter. In one embodiment, the invention provides a host cell capable of producing the fusion protein.

The term "vector," or "recombinant vector" as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors". Vectors, including expression vectors, comprise the nucleotide sequence encoding the antibodies or antigen-binding fragments described herein and a heterogeneous sequence necessary for proper propagation of the vector and expression of the encoded polypeptide. The heterogeneous sequence (i.e., sequence from a difference species than the polypeptide) can comprise a heterologous promoter or heterologous transcriptional regulatory region that allows for expression of the polypeptide. As used herein, the terms "heterologous promoter," "promoter," "promoter region," or "promoter sequence" refer generally to transcriptional regulatory regions of a gene, which may be found at the 5' or 3' side of the polynucleotides described herein, or within the coding region of the polynucleotides, or within introns in the polynucleotides. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site, as well as protein binding domains (consensus sequences) responsible for the binding of RNA polymerase.

In another aspect, provided herein is an immunogenic composition including the CRBD-MTT fusion proteins as described herein that, upon introduction into a host, will confer immunity to that host, in the event the host is subsequently challenged by a SARS-COV-2 virus. In preferred embodiments, the immunogenic composition is a vaccine comprising the CRBD-MTT fusion proteins as described herein and further comprising an excipient and/or diluent appropriate where the composition is to be administered to a subject in need of vaccination against SARS-COV-2.

The term "vaccine," as used herein, refers to a composition that includes an antigen. Vaccine may also include a biological preparation that improves immunity to a particular disease. A vaccine may typically contain an agent, referred to as an antigen, that resembles a disease-causing microorganism, and the agent may often be made from weakened or killed forms of the microbe, its toxins or one of its surface proteins. The antigen may stimulate the body's immune system to recognize the agent as foreign, destroy it, and "remember" it, so that the immune system can more easily recognize and destroy any of these microorganisms that it later encounters. Similarly, the modified toxin preparations, combined with vaccines against other pathogens, could "boost" the immune responses to the pathogen of interest, by acting themselves as vaccine adjuvants. Adjuvants can be classified according to their physiochemical properties or mechanisms of action. The two major classes of adjuvants include compounds that directly act on the immune system such as bacterial toxins that stimulate immune responses, and molecules able to facilitate the presentation of antigens in a controlled manner and behaving as a carrier.

Selection of appropriate vaccine components is within the routine capability of the skilled person. For example, the vaccine composition of the invention may conveniently be formulated using a pharmaceutically acceptable excipient or diluent, such as, for example, an aqueous solvent, non-aqueous solvent, non-toxic-excipient, such as a salt, preservative, buffer and the like. Examples of non-aqueous solvents are propylene glycol, polyethylene glycol, vegetable oil and injectable organic esters such as ethyloleate. Aqueous solvents include water, alcoholic/aqueous solutions, saline solutions, parenteral vehicles such as sodium chloride, Ringer's dextrose, etc. Preservatives include antimicrobial, anti-oxidants, chelating agents and inert gases. The pH and exact concentration of the various components the vaccine composition are adjusted according to routine skills.

In some cases, the preparation described herein may include purified modified toxins, including preparation comprising partial toxin complexes. In some embodiments, the preparations may further include stabilizers that are known to stabilize the CRBD and tetanus toxin proteins. Suitable stabilizers are known in the art, and include, but are not limited to, for example, human or bovine serum albumin, gelatin, recombinant albumin as described in US Publication US2005/0238663 (the contents of which are incorporated by reference in its entirety) among others.

The terms "subject" and "patient" are used interchangeably and refer to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

A preparation of the present invention can be administered in a therapeutically effective amount. The terms "effective amount" or "therapeutically effective amount" refer to an amount of an antigen or vaccine that would induce an immune response in a subject receiving the antigen or vaccine which is adequate to prevent signs or symptoms of disease, including adverse health effects or complications thereof, caused by infection with a pathogen, such as a virus or a bacterium. Humoral immunity or cell mediated immunity or both humoral and cell mediated immunity may be induced. The immunogenic response of an animal to a vaccine or composition may be evaluated, e.g., indirectly through measurement of antibody titers, lymphocyte proliferation assays, or directly through monitoring signs and symptoms after challenge with wild-type strain. The protective immunity conferred by a vaccine or composition may be evaluated by measuring, e.g., reduction in clinical signs such as mortality, morbidity, temperature number, overall physical condition, and overall health and performance of the subject. The amount of a vaccine that is therapeutically effective may vary depending on the particular preparation used, or the condition of the subject, and may be determined by a physician.

A preparation of the present invention can be administered in a therapeutically effective amount depending on the type of treatment necessary. Methods of determining suitable dosage or dosage ranges for individual treatment are known to those in the art. For methods provided herein, a preparation of the present invention can be administered by any means that achieves the intended purpose or is deemed appropriate by those skilled in the art. In an exemplary embodiment, a modified toxin preparation is administered either as a single dose or, when appropriate, as continuous administration using, for instance, a mini pump system. In some cases, a CRBD-MTT fusion proteins as described herein is provided as a liquid dosages form or as a lyophilized dosages form that is, for example, reconstituted prior to administration.

The fusion peptide or compositions comprising the same can be used to elicit an immune response against the fusion peptide, particularly the SARS-COV-2 peptide. A suitable immune response to the fusion protein or composition is the development in a subject of a humoral and/or a cellular immune response to the SARS-COV-2 antigen present in the composition of interest. For purposes of the present invention, a "humoral immune response" refers to an immune response mediated by antibody molecules, including secretory (IgA) or IgG molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular pathogens, or the lysis of cells infected with such pathogens. The fusion peptide or compositions described herein can be used to elicit an immune response that reduces COVID-19 disease progression or can reduce COVID-19. In some embodiments, the fusion peptide or compositions described herein reduce or eliminate moderate or severe COVID-19 disease, by reducing or inhibiting one or more symptoms of COV-19. Further, the immune response in some embodiments may reduce the viral titer load of an infected individual.

The term "protected," as used herein, refers to immunization of a patient against a disease or condition. The immunization may be caused by administering a vaccine comprising an antigen. Specifically, in the present invention, the immunized patient is protected from COVID-19.

In one embodiment, a suitable dosage is from about 1 μg to 25 μg.

Suitable routes of administration for the preparations of the CRBD-MTT fusion proteins described herein include, but are not limited to, direct injection. In certain embodiments, each dose is administered intramuscularly.

Dosage, toxicity, and therapeutic efficacy of the agents of the present technology can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$.

Unless defined otherwise, all technical and scientific terms used herein have the same meaning as commonly understood by one of ordinary skill in the art to which the invention pertains. All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein, the terms "approximately" or "about" in reference to a number are generally taken to include numbers that fall within a range of 5% in either direction (greater than or less than) the number unless otherwise stated or otherwise evident from the context (except where such number would exceed 100% of a possible value). Where ranges are stated, the endpoints are included within the range unless otherwise stated or otherwise evident from the context.

The present invention has been described in terms of one or more preferred embodiments, and it should be appreciated that many equivalents, alternatives, variations, and modifications, aside from those expressly stated, are possible and within the scope of the invention.

EXAMPLES

Example 1

This section describes an embodiment of the SARS-COV-2 inactivated tetanus toxin vaccines provided in this disclosure.

Figure 2:
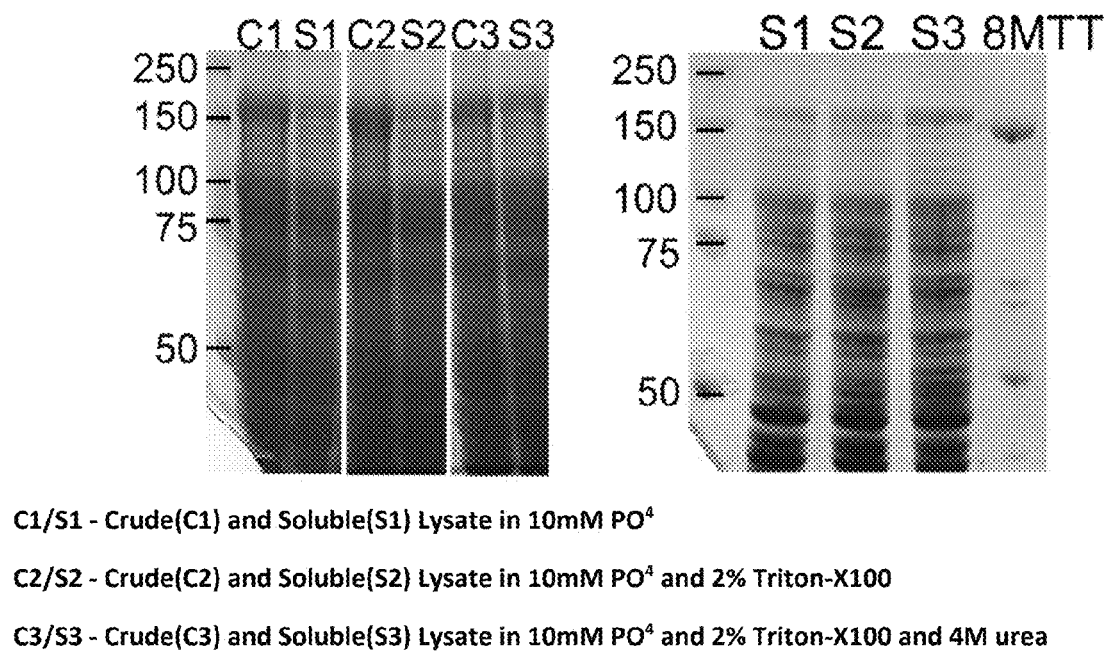
FIG. 2 shows an SDS-PAGE gel of various buffer conditions used to harvest CRBD-8MTT.
Figure 3:
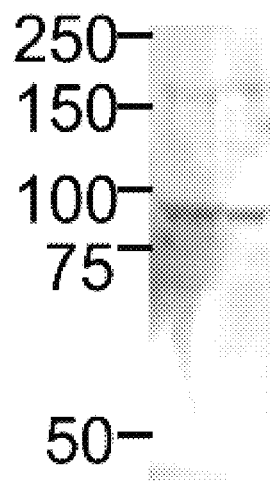
FIG. 3 shows a Western blot using anti-8MTT IgG sera.
Figure 4:
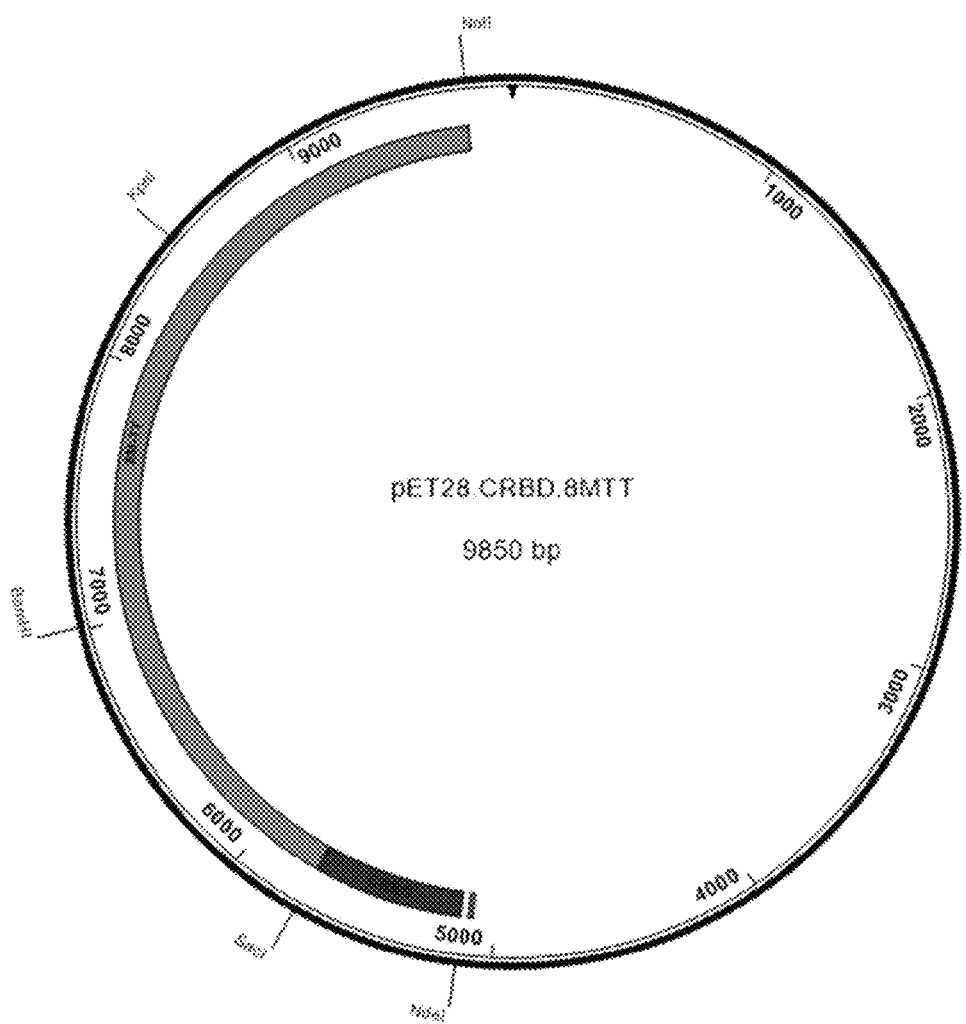
FIG. 4 shows the vector map for the pET28.CRBD.8MTT expression vector.

DNA encoding CRBD commercially synthesized for optimal protein expression in *E. coli*. DNA encoding CRBD was subcloned 5' to the gene encoding genetically inactivated tetanus toxin (8MTT) for expression in *E. coli*, using a pET28 vector for expression (FIGS. 1 and 4). The entire open reading frame of CRBD-8MTT was sequenced to confirm the chimera and that there were no secondary mutations in the clone. Using a standard protein purification protocol, CRBD-8MTT has been produced as a soluble protein. CRBD-8MTT solubility is approximately 40% based on total CRBD-8MTT protein made. By SDS-PAGE, a band that reacts with anti-8MTT IgG was observed to migrate at a higher molecular weight than 8MTT consistent with the production of CRBD-8MTT (FIGS. 2 and 3).

A fusion protein was engineered to contain the receptor binding domain of SARS-COV-2 encoding residues 330-521 (CRBD) of the spike protein of the SARS-COV-2[1] fused to 8MTT. The resulting product is termed CRBD-8MTT. The CRBD is the interaction site of the spike protein with ACE2. ACE2 is the host protein receptor for SARS coronavirus and SARS-COV-2. The RBD is also the binding site for several neutralizing antibodies of the related SARS coronavirus[1,2].

The CRBD-8MTT construct includes the 192 amino acid Receptor Binding domain of the SARS-COV-2 spike protein. Within the SARS-COV-2 spike protein, the RBD is residues 330-521. The CRBD-8MTT construct also includes the 1315 amino acids of the inactivated tetanus toxin. The inactivated tetanus toxin includes 8 point mutations at positions 26, 230, 234, 372, 375, 768, 1226, and 1289 that inactivate the catalytic, LC translocation, and receptor binding domains of the tetanus toxin.

Using recombinant DNA technology, DNA encoding the CRBD was subcloned 5' of the gene encoding 8MTT, producing CRBD-8MTT. The CRBD-8MTT construct includes a first restriction site (amino acids HM, indicated in underline lower case letters), the SARS-COV-2 receptor binding domain (CRBD, indicated in bold text), a GGGGG-penta glycine bridge (indicated in bold underlined text), a second restriction site (amino acids EL, indicated in underlined UPPER CASE TEXT), and the 8MTT inactivated tetanus toxin (indicated in italics), including the 8 point mutations (indicated in underlined italics). DNA and the encoded protein comprising CRBD-8MTT follow.

DNA sequence of SARS-COV-2 (RBD)-8MTT (SEQ ID NO:9):

```
catatgCCGAACATTACCAACCTGTGCCCGTTTGGCGAAGTGTTTAACG

CGACCCGTTTTGCGAGCGTGTATGCGTGGAACCGTAAACGTATTAGCAA

CTGCGTGGCGGATTATAGCGTGCTGTATAACAGCGCGAGCTTTAGCACC

TTTAAATGCTATGGCGTGAGCCCGACCAAACTGAACGATCTGTGCTTTA

CCAACGTGTATGCGGATAGCTTTGTGATTCGTGGCGATGAAGTGCGTCA

GATTGCGCCGGGCCAGACCGGCAAAATTGCGGATTATAACTATAAACTG

CCGGATGATTTTACCGGCTGCGTGATTGCGTGGAACAGCAACAACCTGG

ATAGCAAAGTGGGCGGCAACTATAACTATCTGTATCGTCTGTTTCGTAA

AAGCAACCTGAAACCGTTTGAACGTGATATTAGCACCGAAATTTATCAG

GCGGGCAGCACCCCGTGCAACGGCGTGGAAGGCTTTAACTGCTATTTTC

CGCTGCAGAGCTATGGCTTTCAGCCGACCAACGGCGTGGGCTATCAGCC

GTATCGTGTGGTGGTGCTGAGCTTTGAACTGCTGCATGCGCCGGGCGGt

GGCGGCGGtGAGCTCatgccgATTACCATTAACAACTTTCGTTATAGCG

ATCCGGTGAACAACGATACCATTATTATGATGGAACCGCCGgcgTGCAA

AGGCCTGGATATTTATTATAAAGCGTTTAAAaTTACCGATCGTATTTGG

ATTGTGCCGGAACGTTATGAATTTGGCACCAAACCGGAAGATTTCAACC

CGCCGAGCAGCCTGATTGAAGGCGCGAGCGAATATTATGATCCGAACTA

TCTGCGTACCGATAGCGATAAAGATCGTTTCCTGCAGACCATGGTGAAA

CTGTTTAACCGTATTAAGAACAACGTGGCGGGCGAAGCGCTGCTGGATA

AAATTATTAACGCGATTCCGTATCTGGGCAACAGCTATAGCCTGCTGGA

TAAATTTGATACCAACAGCAACAGCGTGAGCTTTAACCTGCTGGAACAA

GATCCGAGCGGCGCGACCACCAAAAGCGCGATGCTGACCAACCTGATTA

TTTTCGGCCCGGGCCCGGTGCTGAACAAAAACGAAGTGCGTGGCATTGT

GCTGCGTGTGGATAACAAGAACTATTTCCCGTGCCGTGATGGCTTTGGC

AGCATTATGCAGATGGCGTTTTGCCCGGAATATGTGCCGACCTTTGATA

ACGTGATTGAAAACATTACCAGCCTGACCATTGGCAAAAGCAAATATTT

CCAAGATCCGGCGCTGaaaCTGATGCATcaaCTGATTCATGTGCTGCAT

GGCCTGTATGGCATGCAGGTGAGCAGCCATGAAATTATTCCGAGCAAAC

AGGAAATTTATATGCAGCATACCTATCCGATTAGCGCGGAAGAACTGTT

TACCTTTGGCGGCCAGGATGCGAACCTGATTAGCATTGATATTAAGAAC

GATCTGTATGAAAAGACCCTGAACGATTATAAAGCGATTGCGAACAAAC

TGAGCCAGGTGACCAGCTGCAACGATCCGAACATTGATATTGATAGCTA

TAAACAGATTTATCAGCAGAAATATCAGTTTGATAAAGATAGCAACGGC

CAGTATATTGTGAACGAAGATAAATTTCAGATTCTGTATAACAGCATTA

TGTATGGCTTTACCGAAATTGAACTGGGCAAGAAATTTAACATTAAAAC

CgctCTGAGCtttTTTAGCATGAACCATGATCCGGTGAAAATTCCGAAC

CTGCTGGATGATACCATTTATAACGATACCGAAGGCTTTAACATTGAAA

GCAAAGACCTGAAAAGCGAATATAAAGGCCAGAACATGCGTGTGAACAC

CAACGCGTTTCGTAACGTGGATGGATCCGGCCTGGTGAGCAAACTGATT

GGCCTGTGCAAGAAGATTATTCCGCCGACCAACATTCGTGAGAACCTGT

ATAACCGTACCGCGAGCCTGACCGATCTGGGCGGCGAACTGTGCATTAA

GATTAAGAACGAAGATCTGACCTTTATTGCGGAGAAGAACAGCTTTAGC

GAAGAACCGTTTCAGGATGAAATTGTGAGCTATAACACCAAGAACAAAC

CGCTGAACTTTAACTATAGCCTGGATAAAATTATTGTGGATTATAACCT

GCAGAGCAAGATTACCCTGCCGAACGATCGTACCACCCCGGTGACCAAA

GGCATTCCGTATGCGCCGGAATATAAGAGCAACGCGGCGAGCACCATTG
```

-continued

AAATTCATAACATTGATGATAACACCATTTATCAGTATCTGTATGCGCA

GAAGAGCCCGACCACCCTGCAGCGTATTACCATGACCAACAGCGTGGAT

GATGCGCTGATTAACAGCACCAAAATTTATAGCTATTTTCCGAGCGTGA

TTAGCAAAGTGAACCAGGGCGCGCAGGGCATTCTGTTTCTGCAGTGGGT

GCGTGATATTATTGATGATTTTACCAACGAAAGCAGCCAGAAAACCACC

ATTGATAAAATTAGCGATGTGAGCACCATTGTGCCGTATATTGGCCCGG

CGCTGAACATTGTGAAACAGGGCTATGAAGGCAACTTTATTGGCGCGCT

GGAAACCACCGGCGTGGTGCTGCTGCTGGAATATATTCCGGAAATTACC

CTGCCGGTGATTGCGGCGCTGAGCATTGCGGAAAGCAGCACCCAGAAAG

AGAAGATTATTAAAACCATTGATAACTTTCTGGAGAAACGTTATGAGAA

ATGGATTGAAGTGTATAAACTGGTGAAAGCGAAATGGCTGGGCACCGTG

AACACCCAGTTTCAGAAACGTAGCTATCAGATGTATCGTAGCCTGGAAT

ATCAGGTGGATGCGATTAAGAAAATTATTGATTATGAATATAAGATTTA

TAGCGGCCCGGATgccGAACAGATTGCGGATGAAATTAACAACCTGAAA

AACAAACTGGAAGAGAAAGCGAACAAAGCGATGATTAACATTAACATCT

TTATGCGTGAAAGCAGCCGTAGCTTTCTGGTGAACCAGATGATTAACGA

AGCGAAGAAACAGCTGCTGGAATTTGATACCCAGAGCAAGAACATTCTG

ATGCAGTATATTAAAGCGAACAGCAAATTTATTGGCATTACCGAACTGA

AGAAACTGGAAAGCAAAATTAACAAAGTGTTTAGCACCCCGATTCCGTT

TAGCTATAGCAAGAACCTGGATTGCTGGGTGGATAACGAAGAAGATATT

GATGTGATTCTGAAGAAGAGCACCATTCTGAACCTGGATATTAACAACG

ATATTATTAGCGATATTAGCGGCTTCAACAGCAGCGTGATTACCTATCC

GGATGCGCAGCTGGTACCGGGCATTAACGGCAAAGCGATTCATCTGGTG

AACAACGAAAGCAGCGAAGTGATTGTGCATAAAGCGATGGATATTGAAT

ATAACGATATGTTCAACAACTTTACCGTGAGCTTTTGGCTGCGTGTGCC

GAAAGTGAGCGCGAGCCATCTGGAACAGTATGGCACCAACGAATATAGC

ATTATTAGCAGCATGAAGAAACATAGCCTGAGCATTGGCAGCGGCTGGA

GCGTGAGCCTGAAAGGCAACAACCTGATTTGGACCCTGAAAGATAGCGC

GGGCGAAGTGCGTCAGATTACCTTTCGTGATCTGCCGGATAAGTTTAAC

GCGTATCTGGCGAACAAATGGGTGTTTATTACCATTACCAACGATCGTC

TGAGCAGCGCGAACCTGTATATTAACGGCGTGCTGATGGGCAGCGCGGA

AATTACCGGCCTGGGCGCGATTCGTGAAGATAACAACATTACCCTGAAA

CTGGATCGTTGCAACAATAACAACCAGTATGTGAGCATTGATAAATTTC

GTATTTTTTGCAAAGCGCTGAACCCGAAAGAAATTGAAAAACTGTATAC

CAGCTATCTGAGCATTACCTTTCTGCGTGATTTTTGGGGCAACCCGCTG

CGTTATGATACCGAATATTATCTGATTCCGGTGGCGAGCAGTAGCAAAG

ATGTGCAGCTGAAGAACATTACCGATTATATGTATCTGACCAACGCGCC

GAGCTATACCAACGGCAAACTGAACATTTACTATCGTCGTCTGTATAAC

GGCCTGAAATTCATTATTAAACGTTATACCCCGAATAACGAAATTGATA

GCTTTGTGAAAAGCGGCGATTTTATTAAACTGTATGTGAGCTATAACAA

-continued

TAACGAACATATTGTGGGCTATCCGAAAGATGGCAACGCGTTTAATAAC

CTGGATCGTATTCTGctgGTGGGCTATAACGCGCCGGGCATTCCGCTGT

ATAAGAAGATGGAAGCGGTGAAACTGCGTGATCTGAAAACCTATAGCGT

GCAGCTGAAACTGTATGATGATAAGAACGCGAGCCTGGGCCTGGTTGGA

ACCCATAACGGTCAGATTGGCAACGATCCAAACCGTGATATTCTGATTG

CGAGCAACgcgTATTTTAACCATCTGAAAGACAAGATCCTGGGCTGTGA

TTGGTACTTCGTTCCGACAGATGAAGGCTGGACCAACGATTAAGCGGCC

GC

Protein sequence of SARS-COV-2 (RBD)-8MTT (SEQ ID NO:10):

hmPNITNLCPFGEVENATRFASVYAWNRKRISNCVADYSVLYNSASFST
FKCYGVSPTKLNDLCFTNVYADSFVIRGDEVRQIAPGQTGKIADYNYKL
PDDFTGCVIAWNSNNLDSKVGGNYNYLYRLFRKSNLKPFERDISTEIYQ
AGSTPCNGVEGENCYFPLQSYGFQPTNGVGYQPYRVVVLSFELLHAPGG
GGGELMPITINNFRYSDPVNNDTIIMMEPPACKGLDIYYKAFKITDRIW
IVPERYEFGTKPEDFNPPSSLIEGASEYYDPNYLRTDSDKDRFLQTMVK
LFNRIKNNVAGEALLDKIINAIPYLGNSYSLLDKFDTNSNSVSFNLLEQ
DPSGATTKSAMLTNLIIFGPGPVLNKNEVRGIVLRVDNKNYFPCRDGFG
SIMQMAFCPEYVPTFDNVIENITSLTIGKSKYFQDPALKLMHQLIHVLH
GLYGMQVSSHEIIPSKQEIYMQHTYPISAEELFTFGGQDANLISIDIKN
DLYEKTLNDYKAIANKLSQVTSCNDPNIDIDSYKQIYQQKYQFDKDSNG
QYIVNEDKFQILYNSIMYGFTEIELGKKFNIKTALSFFSMNHDPVKIPN
LLDDTIYNDTEGFNIESKDLKSEYKGQNMRVNTNAFRNVDGSGLVSKLI
GLCKKIIPPTNIRENLYNRTASLTDLGGELCIKIKNEDLTFIAEKNSFS
EEPFQDEIVSYNTKNKPLNFNYSLDKIIVDYNLQSKITLPNDRTTPVTK
GIPYAPEYKSNAASTIEIHNIDDNTIYQYLYAQKSPTTLQRITMTNSVD
DALINSTKIYSYFPSVISKVNQGAQGILFLQWVRDIIDDFTNESSQKTT
IDKISDVSTIVPYIGPALNIVKQGYEGNFIGALETTGVVLLLEYIPEIT
LPVIAALSIAESSTQKEKIIKTIDNFLEKRYEKWIEVYKLVKAKWLGTV
NTQFQKRSYQMYRSLEYQVDAIKKIIDYEYKIYSGPDAEQIADEINNLK
NKLEEKANKAMININIFMRESSRSFLVNQMINEAKKQLLEFDTQSKNIL
MQYIKANSKFIGITELKKLESKINKVFSTPIPFSYSKNLDCWVDNEEDI
DVILKKSTILNLDINNDIISDISGENSSVITYPDAQLVPGINGKAIHLV
NNESSEVIVHKAMDIEYNDMFNNFTVSFWLRVPKVSASHLEQYGTNEYS
IISSMKKHSLSIGSGWSVSLKGNNLIWTLKDSAGEVRQITFRDLPDKFN
AYLANKWVFITITNDRLSSANLYINGVLMGSAEITGLGAIREDNNITLK
LDRCNNNNQYVSIDKFRIFCKALNPKEIEKLYTSYLSITFLRDFWGNPL
RYDTEYYLIPVASSSKDVQLKNITDYMYLTNAPSYTNGKLNIYYRRLYN

-continued

```
GLKFIIKRYTPNNEIDSFVKSGDFIKLYVSYNNNEHIVGYPKDGNAFNN

LDRILLVGYNAPGIPLYKKMEAVKLRDLKTYSVQLKLYDDKNASLGLVG

THNGQIGNDPNRDILIASNAYFNHLKDKILGCDWYFVPTDEGWTND
```

REFERENCES

1. Wrapp, D.; Wang, N.; Corbett, K. S.; Goldsmith, J. A.; Hsieh, C. L.; Abiona, O.; Graham, B. S.; Mclellan, J. S., Cryo-EM structure of the 2019-nCOV spike in the prefusion conformation. *Science* 2020, 367 (6483), 1260-1263.
2. Bisht, H.; Roberts, A.; Vogel, L.; Subbarao, K.; Moss, B., Neutralizing antibody and protective immunity to SARS coronavirus infection of mice induced by a soluble recombinant polypeptide containing an N-terminal segment of the spike glycoprotein. *Virology* 2005, 334 (2), 160-5.
3. Graham, R. L.; Donaldson, E. F.; Baric, R. S., A decade after SARS: strategies for controlling emerging coronaviruses. *Nat Rev Microbiol* 2013, 11 (12), 836-48.

Example 2

This section describes additional embodiments of SARS-COV-2 inactivated tetanus toxin antigenic polypeptides of this disclosure. It was determined that fusion of various portions of the SARS-COV-2 spike protein RBD to the N-terminus of 8MTT produced chimeras that were not soluble or poorly soluble. To address this problem, additional fusion proteins were engineered in which portions of the RBD were fused to the C-terminus of 8MTT, thus constructing; 8MTT(RBD330-525), 8MTT(RBD376-525) and 8MTT(RBD433-524). The three chimeras were expressed in *E. coli*, but only 8MTT(RBD376-525) and 8MTT(RBD433-524) were soluble. 8MTT(RBD433-524) was determined to be more manageable to work with than 8MTTRBD(376-525), so further experiments were performed with 8MTT(RBD433-524).

FIG. 12 illustrates exemplary "8MTT(RBD433-524)" fusion protein embodiments. RBD(433-524) refers to a portion of the receptor binding domain (amino acids 330-525) of the SARS-COV-2 spike protein. RBD(433-524) contains the binding sites for several monoclonal antibodies (REGN10987 and REGN10933) that complementally neutralize SARS-COV-2 infections in cultured cells (Ref 1). Accordingly, experiments were designed to test the ability of RBD(433-524) to stimulate the production of antibodies that will neutralize SARS-COV-2 by redundant mechanisms. It was determined that 8MTT(RBD433-524) reacts with anti-sera to the RBD of the SARS-COV-2 spike protein. Importantly, 8MTT(RBD433-524) is a soluble protein when produced in *E. coli*, which suggests it is well suited for use as a vaccine. Experiments are underway to purify 8MTT(RBD433-524) and to test the purified protein via vaccination into mice. Antisera to 8MTT(RBD433-524) will be tested to determine whether the antigen raises antibodies to the RBD433-524 domain and whether those antibodies block RBD-ACE2 interactions.

We claim:

1. A fusion protein comprising
   (i) a modified tetanus toxin (MTT) polypeptide comprising a sequence having at least 95% identity to SEQ ID NO:1, having a mutation at each of positions R372 and Y375, and having a mutation at two or more positions selected from E234, K768, R1226, and W1289, wherein each position is numbered relative to SEQ ID NO:1, the MTT polypeptide having reduced toxicity and receptor binding compared to the toxicity and receptor binding of SEQ ID NO: 1; and
   (ii) a SARS-COV-2 spike protein receptor binding domain (CRBD) polypeptide or a portion thereof.

2. The fusion protein of claim 1, wherein the CRBD polypeptide or a portion thereof comprises at least a portion of SEQ ID NO:3.

3. The fusion protein of claim 1, wherein the CRBD polypeptide or a portion thereof comprises a sequence having at least 95% identity to SEQ ID NO:3.

4. The fusion protein of claim 1, wherein the CRBD polypeptide or a portion thereof comprises an amino acid sequence corresponding to residues 376-525 or 433-524 of SEQ ID NO: 2.

5. The fusion protein of claim 1, wherein the MTT polypeptide and the CRBD polypeptide are connected by a linker polypeptide.

6. The fusion protein of claim 5, wherein the linker polypeptide is a poly-glycine sequence.

7. The fusion protein of claim 1, wherein the MTT polypeptide and the CRBD polypeptide are chemically cross-linked.

8. The fusion protein of claim 1, wherein in the MTT polypeptide amino acid R at position R372 is replaced with amino acid A, and wherein amino acid Y at position Y375 is replaced with amino acid F.

9. The fusion protein of claim 1, wherein the MTT polypeptide mutations comprise R372A, Y375F, E234Q, R1226L, and W1289A.

10. The fusion protein of claim 9, wherein the MTT polypeptide comprises SEQ ID NO:5.

11. The fusion protein of claim 1, wherein the MTT polypeptide mutations comprise R372A, Y375F, E234Q, K768A, R1226L, and W1289A.

12. The fusion protein of claim 11, wherein the MTT polypeptide comprises SEQ ID NO:6.

13. The fusion protein of claim 1, wherein the MTT polypeptide further comprises a mutation at one or both of positions L230 and Y26, wherein each position is numbered relative to SEQ ID NO: 1.

14. The fusion protein of claim 13, wherein the mutations at one or both of positions L230 and Y26 comprise L230K and Y26A.

15. The fusion protein of claim 14, wherein the MTT polypeptide comprises SEQ ID NO:7 or SEQ ID NO:8.

16. The fusion protein of claim 1, wherein the fusion protein comprises a sequence at least 95% identical to SEQ ID NO:10.

17. A polynucleotide encoding the fusion protein of claim 1.

18. The polynucleotide of claim 17, wherein the polynucleotide comprises a sequence at least 95% identical to SEQ ID NO:9.

19. A vector comprising the polynucleotide of claim 18.

20. A composition comprising the fusion protein of claim 1 and a pharmaceutically acceptable carrier.

21. A method of reducing the risk of a subject developing COVID-19 by inducing an immune response through administering to the subject a therapeutically effective amount of the fusion protein of claim 1.

22. A method for producing a CRBD-MTT chemically cross-linked fusion protein comprising:
    obtaining a polypeptide composition comprising (i) a modified tetanus toxin (MTT) polypeptide comprising a sequence having at least 95% identity to SEQ ID NO:1, having a mutation at each of positions R372 and Y375, and having a mutation at two or more positions selected from E234, K768, R1226, and W1289, wherein each position is numbered relative to SEQ ID NO:1, and (ii) a SARS-COV-2 spike protein receptor binding domain (CRBD) polypeptide or a portion thereof; and
    contacting the polypeptide composition with a crosslinking agent for a time and under conditions sufficient to chemically crosslink the CRBD polypeptide and the MTT polypeptide; whereby a CRBD-MTT chemically cross-linked fusion protein is produced.

23. The method of claim 22, wherein the crosslinking agent is selected from the group consisting of formaldehyde, disuccinimidyl suberate (DSS), succinimidyl-4-(N-maleimidomethyl)cyclohexane-1-carboxylate (SMCC), ethylene glycol bis(sulfosuccinimidylsuccinate) (Sulfo-EGS), bis(sulfosuccinimidyl)suberate (BS3), and dithiobis(succinimidylpropionate) (DSP).

24. The method of claim 22, wherein the CRBD polypeptide comprises a sequence having at least 95% identity to SEQ ID NO:3.

25. The method of claim 22, wherein the CRBD polypeptide or a portion thereof comprises an amino acid sequence corresponding to residues 433-524 of SEQ ID NO:2.

26. The method of claim 22, wherein the CRBD polypeptide or a portion thereof comprises an amino acid sequence corresponding to residues 376-525 of SEQ ID NO:2.

* * * * *

SEQUENCE LISTING

```
<160> NUMBER OF SEQ ID NOS: 10

<210> SEQ ID NO 1
<211> LENGTH: 1315
<212> TYPE: PRT
<213> ORGANISM: Clostridium tetani CN3911
<220> FEATURE:
<221> NAME/KEY: MISC_FEATURE
<222> LOCATION: (1)..(1315)
<223> OTHER INFORMATION: Wild-type tetanus toxin

<400> SEQUENCE: 1

Met Pro Ile Thr Ile Asn Asn Phe Arg Tyr Ser Asp Pro Val Asn Asn
1               5                   10                  15

Asp Thr Ile Ile Met Met Glu Pro Pro Tyr Cys Lys Gly Leu Asp Ile
            20                  25                  30

Tyr Tyr Lys Ala Phe Lys Ile Thr Asp Arg Ile Trp Ile Val Pro Glu
        35                  40                  45

Arg Tyr Glu Phe Gly Thr Lys Pro Glu Asp Phe Asn Pro Pro Ser Ser
    50                  55                  60

Leu Ile Glu Gly Ala Ser Glu Tyr Tyr Asp Pro Asn Tyr Leu Arg Thr
65                  70                  75                  80

Asp Ser Asp Lys Asp Arg Phe Leu Gln Thr Met Val Lys Leu Phe Asn
                85                  90                  95

Arg Ile Lys Asn Asn Val Ala Gly Glu Ala Leu Leu Asp Lys Ile Ile
            100                 105                 110

Asn Ala Ile Pro Tyr Leu Gly Asn Ser Tyr Ser Leu Leu Asp Lys Phe
        115                 120                 125

Asp Thr Asn Ser Asn Ser Val Ser Phe Asn Leu Leu Glu Gln Asp Pro
    130                 135                 140
```

```
Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
            165                 170                 175

Arg Val Asp Asn Lys Asn Tyr Phe Pro Cys Arg Asp Gly Phe Gly Ser
        180                 185                 190

Ile Met Gln Met Ala Phe Cys Pro Glu Tyr Val Pro Thr Phe Asp Asn
    195                 200                 205

Val Ile Glu Asn Ile Thr Ser Leu Thr Ile Gly Lys Ser Lys Tyr Phe
    210                 215                 220

Gln Asp Pro Ala Leu Leu Leu Met His Glu Leu Ile His Val Leu His
225                 230                 235                 240

Gly Leu Tyr Gly Met Gln Val Ser Ser His Glu Ile Ile Pro Ser Lys
            245                 250                 255

Gln Glu Ile Tyr Met Gln His Thr Tyr Pro Ile Ser Ala Glu Glu Leu
        260                 265                 270

Phe Thr Phe Gly Gly Gln Asp Ala Asn Leu Ile Ser Ile Asp Ile Lys
    275                 280                 285

Asn Asp Leu Tyr Glu Lys Thr Leu Asn Asp Tyr Lys Ala Ile Ala Asn
290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
            325                 330                 335

Asn Gly Gln Tyr Ile Val Asn Glu Asp Lys Phe Gln Ile Leu Tyr Asn
        340                 345                 350

Ser Ile Met Tyr Gly Phe Thr Glu Ile Glu Leu Gly Lys Lys Phe Asn
    355                 360                 365

Ile Lys Thr Arg Leu Ser Tyr Phe Ser Met Asn His Asp Pro Val Lys
    370                 375                 380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
            405                 410                 415

Arg Val Asn Thr Asn Ala Phe Arg Asn Val Asp Gly Ser Gly Leu Val
        420                 425                 430

Ser Lys Leu Ile Gly Leu Cys Lys Lys Ile Ile Pro Pro Thr Asn Ile
    435                 440                 445

Arg Glu Asn Leu Tyr Asn Arg Thr Ala Ser Leu Thr Asp Leu Gly Gly
    450                 455                 460

Glu Leu Cys Ile Lys Ile Lys Asn Glu Asp Leu Thr Phe Ile Ala Glu
465                 470                 475                 480

Lys Asn Ser Phe Ser Glu Glu Pro Phe Gln Asp Glu Ile Val Ser Tyr
            485                 490                 495

Asn Thr Lys Asn Lys Pro Leu Asn Phe Asn Tyr Ser Leu Asp Lys Ile
        500                 505                 510

Ile Val Asp Tyr Asn Leu Gln Ser Lys Ile Thr Leu Pro Asn Asp Arg
    515                 520                 525

Thr Thr Pro Val Thr Lys Gly Ile Pro Tyr Ala Pro Glu Tyr Lys Ser
    530                 535                 540

Asn Ala Ala Ser Thr Ile Glu Ile His Asn Ile Asp Asp Asn Thr Ile
545                 550                 555                 560

Tyr Gln Tyr Leu Tyr Ala Gln Lys Ser Pro Thr Thr Leu Gln Arg Ile
```

```
            565                 570                 575
Thr Met Thr Asn Ser Val Asp Asp Ala Leu Ile Asn Ser Thr Lys Ile
            580                 585                 590
Tyr Ser Tyr Phe Pro Ser Val Ile Ser Lys Val Asn Gln Gly Ala Gln
            595                 600                 605
Gly Ile Leu Phe Leu Gln Trp Val Arg Asp Ile Ile Asp Asp Phe Thr
            610                 615                 620
Asn Glu Ser Ser Gln Lys Thr Thr Ile Asp Lys Ile Ser Asp Val Ser
625                 630                 635                 640
Thr Ile Val Pro Tyr Ile Gly Pro Ala Leu Asn Ile Val Lys Gln Gly
                    645                 650                 655
Tyr Glu Gly Asn Phe Ile Gly Ala Leu Glu Thr Thr Gly Val Val Leu
                    660                 665                 670
Leu Leu Glu Tyr Ile Pro Glu Ile Thr Leu Pro Val Ile Ala Ala Leu
                    675                 680                 685
Ser Ile Ala Glu Ser Ser Thr Gln Lys Glu Lys Ile Ile Lys Thr Ile
                    690                 695                 700
Asp Asn Phe Leu Glu Lys Arg Tyr Glu Lys Trp Ile Glu Val Tyr Lys
705                 710                 715                 720
Leu Val Lys Ala Lys Trp Leu Gly Thr Val Asn Thr Gln Phe Gln Lys
                    725                 730                 735
Arg Ser Tyr Gln Met Tyr Arg Ser Leu Glu Tyr Gln Val Asp Ala Ile
                    740                 745                 750
Lys Lys Ile Ile Asp Tyr Glu Tyr Lys Ile Tyr Ser Gly Pro Asp Lys
                    755                 760                 765
Glu Gln Ile Ala Asp Glu Ile Asn Asn Leu Lys Asn Lys Leu Glu Glu
                    770                 775                 780
Lys Ala Asn Lys Ala Met Ile Asn Ile Asn Ile Phe Met Arg Glu Ser
785                 790                 795                 800
Ser Arg Ser Phe Leu Val Asn Gln Met Ile Asn Glu Ala Lys Lys Gln
                    805                 810                 815
Leu Leu Glu Phe Asp Thr Gln Ser Lys Asn Ile Leu Met Gln Tyr Ile
                    820                 825                 830
Lys Ala Asn Ser Lys Phe Ile Gly Ile Thr Glu Leu Lys Lys Leu Glu
                    835                 840                 845
Ser Lys Ile Asn Lys Val Phe Ser Thr Pro Ile Pro Phe Ser Tyr Ser
                    850                 855                 860
Lys Asn Leu Asp Cys Trp Val Asp Asn Glu Glu Asp Ile Asp Val Ile
865                 870                 875                 880
Leu Lys Lys Ser Thr Ile Leu Asn Leu Asp Ile Asn Asn Asp Ile Ile
                    885                 890                 895
Ser Asp Ile Ser Gly Phe Asn Ser Ser Val Ile Thr Tyr Pro Asp Ala
                    900                 905                 910
Gln Leu Val Pro Gly Ile Asn Gly Lys Ala Ile His Leu Val Asn Asn
                    915                 920                 925
Glu Ser Ser Glu Val Ile Val His Lys Ala Met Asp Ile Glu Tyr Asn
                    930                 935                 940
Asp Met Phe Asn Asn Phe Thr Val Ser Phe Trp Leu Arg Val Pro Lys
945                 950                 955                 960
Val Ser Ala Ser His Leu Glu Gln Tyr Gly Thr Asn Glu Tyr Ser Ile
                    965                 970                 975
Ile Ser Ser Met Lys Lys His Ser Leu Ser Ile Gly Ser Gly Trp Ser
                    980                 985                 990
```

Val Ser Leu Lys Gly Asn Asn Leu Ile Trp Thr Leu Lys Asp Ser Ala
            995                 1000                1005

Gly Glu Val Arg Gln Ile Thr Phe Arg Asp Leu Pro Asp Lys Phe
    1010                1015                1020

Asn Ala Tyr Leu Ala Asn Lys Trp Val Phe Ile Thr Ile Thr Asn
    1025                1030                1035

Asp Arg Leu Ser Ser Ala Asn Leu Tyr Ile Asn Gly Val Leu Met
    1040                1045                1050

Gly Ser Ala Glu Ile Thr Gly Leu Gly Ala Ile Arg Glu Asp Asn
    1055                1060                1065

Asn Ile Thr Leu Lys Leu Asp Arg Cys Asn Asn Asn Gln Tyr
    1070                1075                1080

Val Ser Ile Asp Lys Phe Arg Ile Phe Cys Lys Ala Leu Asn Pro
    1085                1090                1095

Lys Glu Ile Glu Lys Leu Tyr Thr Ser Tyr Leu Ser Ile Thr Phe
    1100                1105                1110

Leu Arg Asp Phe Trp Gly Asn Pro Leu Arg Tyr Asp Thr Glu Tyr
    1115                1120                1125

Tyr Leu Ile Pro Val Ala Ser Ser Ser Lys Asp Val Gln Leu Lys
    1130                1135                1140

Asn Ile Thr Asp Tyr Met Tyr Leu Thr Asn Ala Pro Ser Tyr Thr
    1145                1150                1155

Asn Gly Lys Leu Asn Ile Tyr Tyr Arg Arg Leu Tyr Asn Gly Leu
    1160                1165                1170

Lys Phe Ile Ile Lys Arg Tyr Thr Pro Asn Asn Glu Ile Asp Ser
    1175                1180                1185

Phe Val Lys Ser Gly Asp Phe Ile Lys Leu Tyr Val Ser Tyr Asn
    1190                1195                1200

Asn Asn Glu His Ile Val Gly Tyr Pro Lys Asp Gly Asn Ala Phe
    1205                1210                1215

Asn Asn Leu Asp Arg Ile Leu Arg Val Gly Tyr Asn Ala Pro Gly
    1220                1225                1230

Ile Pro Leu Tyr Lys Lys Met Glu Ala Val Lys Leu Arg Asp Leu
    1235                1240                1245

Lys Thr Tyr Ser Val Gln Leu Lys Leu Tyr Asp Asp Lys Asn Ala
    1250                1255                1260

Ser Leu Gly Leu Val Gly Thr His Asn Gly Gln Ile Gly Asn Asp
    1265                1270                1275

Pro Asn Arg Asp Ile Leu Ile Ala Ser Asn Trp Tyr Phe Asn His
    1280                1285                1290

Leu Lys Asp Lys Ile Leu Gly Cys Asp Trp Tyr Phe Val Pro Thr
    1295                1300                1305

Asp Glu Gly Trp Thr Asn Asp
    1310                1315

<210> SEQ ID NO 2
<211> LENGTH: 1273
<212> TYPE: PRT
<213> ORGANISM: SARS-COV-2
<220> FEATURE:
<221> NAME/KEY: misc_feature
<222> LOCATION: (1)..(1273)
<223> OTHER INFORMATION: Spike protein

<400> SEQUENCE: 2

```
Met Phe Val Phe Leu Val Leu Leu Pro Leu Val Ser Ser Gln Cys Val
  1               5                  10                  15

Asn Leu Thr Thr Arg Thr Gln Leu Pro Pro Ala Tyr Thr Asn Ser Phe
             20                  25                  30

Thr Arg Gly Val Tyr Tyr Pro Asp Lys Val Phe Arg Ser Ser Val Leu
             35                  40                  45

His Ser Thr Gln Asp Leu Phe Leu Pro Phe Phe Ser Asn Val Thr Trp
 50                  55                  60

Phe His Ala Ile His Val Ser Gly Thr Asn Gly Thr Lys Arg Phe Asp
 65                  70                  75                  80

Asn Pro Val Leu Pro Phe Asn Asp Gly Val Tyr Phe Ala Ser Thr Glu
             85                  90                  95

Lys Ser Asn Ile Ile Arg Gly Trp Ile Phe Gly Thr Thr Leu Asp Ser
             100                 105                 110

Lys Thr Gln Ser Leu Leu Ile Val Asn Asn Ala Thr Asn Val Val Ile
             115                 120                 125

Lys Val Cys Glu Phe Gln Phe Cys Asn Asp Pro Phe Leu Gly Val Tyr
             130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
             165                 170                 175

Met Asp Leu Glu Gly Lys Gln Gly Asn Phe Lys Asn Leu Arg Glu Phe
             180                 185                 190

Val Phe Lys Asn Ile Asp Gly Tyr Phe Lys Ile Tyr Ser Lys His Thr
             195                 200                 205

Pro Ile Asn Leu Val Arg Asp Leu Pro Gln Gly Phe Ser Ala Leu Glu
             210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
             245                 250                 255

Gly Trp Thr Ala Gly Ala Ala Ala Tyr Tyr Val Gly Tyr Leu Gln Pro
             260                 265                 270

Arg Thr Phe Leu Leu Lys Tyr Asn Glu Asn Gly Thr Ile Thr Asp Ala
             275                 280                 285

Val Asp Cys Ala Leu Asp Pro Leu Ser Glu Thr Lys Cys Thr Leu Lys
             290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
             325                 330                 335

Pro Phe Gly Glu Val Phe Asn Ala Thr Arg Phe Ala Ser Val Tyr Ala
             340                 345                 350

Trp Asn Arg Lys Arg Ile Ser Asn Cys Val Ala Asp Tyr Ser Val Leu
             355                 360                 365

Tyr Asn Ser Ala Ser Phe Ser Thr Phe Lys Cys Tyr Gly Val Ser Pro
             370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
             405                 410                 415

Lys Ile Ala Asp Tyr Asn Tyr Lys Leu Pro Asp Asp Phe Thr Gly Cys
```

-continued

```
                420             425             430
    Val Ile Ala Trp Asn Ser Asn Asn Leu Asp Ser Lys Val Gly Gly Asn
                435             440             445
    Tyr Asn Tyr Leu Tyr Arg Leu Phe Arg Lys Ser Asn Leu Lys Pro Phe
                450             455             460
    Glu Arg Asp Ile Ser Thr Glu Ile Tyr Gln Ala Gly Ser Thr Pro Cys
    465             470             475             480
    Asn Gly Val Glu Gly Phe Asn Cys Tyr Phe Pro Leu Gln Ser Tyr Gly
                        485             490             495
    Phe Gln Pro Thr Asn Gly Val Gly Tyr Gln Pro Tyr Arg Val Val Val
                    500             505             510
    Leu Ser Phe Glu Leu Leu His Ala Pro Ala Thr Val Cys Gly Pro Lys
                515             520             525
    Lys Ser Thr Asn Leu Val Lys Asn Lys Cys Val Asn Phe Asn Phe Asn
                530             535             540
    Gly Leu Thr Gly Thr Gly Val Leu Thr Glu Ser Asn Lys Lys Phe Leu
    545             550             555             560
    Pro Phe Gln Gln Phe Gly Arg Asp Ile Ala Asp Thr Thr Asp Ala Val
                        565             570             575
    Arg Asp Pro Gln Thr Leu Glu Ile Leu Asp Ile Thr Pro Cys Ser Phe
                    580             585             590
    Gly Gly Val Ser Val Ile Thr Pro Gly Thr Asn Thr Ser Asn Gln Val
                595             600             605
    Ala Val Leu Tyr Gln Asp Val Asn Cys Thr Glu Val Pro Val Ala Ile
                610             615             620
    His Ala Asp Gln Leu Thr Pro Thr Trp Arg Val Tyr Ser Thr Gly Ser
    625             630             635             640
    Asn Val Phe Gln Thr Arg Ala Gly Cys Leu Ile Gly Ala Glu His Val
                        645             650             655
    Asn Asn Ser Tyr Glu Cys Asp Ile Pro Ile Gly Ala Gly Ile Cys Ala
                    660             665             670
    Ser Tyr Gln Thr Gln Thr Asn Ser Pro Arg Arg Ala Arg Ser Val Ala
                675             680             685
    Ser Gln Ser Ile Ile Ala Tyr Thr Met Ser Leu Gly Ala Glu Asn Ser
                690             695             700
    Val Ala Tyr Ser Asn Asn Ser Ile Ala Ile Pro Thr Asn Phe Thr Ile
    705             710             715             720
    Ser Val Thr Thr Glu Ile Leu Pro Val Ser Met Thr Lys Thr Ser Val
                        725             730             735
    Asp Cys Thr Met Tyr Ile Cys Gly Asp Ser Thr Glu Cys Ser Asn Leu
                    740             745             750
    Leu Leu Gln Tyr Gly Ser Phe Cys Thr Gln Leu Asn Arg Ala Leu Thr
                755             760             765
    Gly Ile Ala Val Glu Gln Asp Lys Asn Thr Gln Glu Val Phe Ala Gln
                770             775             780
    Val Lys Gln Ile Tyr Lys Thr Pro Pro Ile Lys Asp Phe Gly Gly Phe
    785             790             795             800
    Asn Phe Ser Gln Ile Leu Pro Asp Pro Ser Lys Pro Ser Lys Arg Ser
                        805             810             815
    Phe Ile Glu Asp Leu Leu Phe Asn Lys Val Thr Leu Ala Asp Ala Gly
                    820             825             830
    Phe Ile Lys Gln Tyr Gly Asp Cys Leu Gly Asp Ile Ala Ala Arg Asp
                835             840             845
```

```
Leu Ile Cys Ala Gln Lys Phe Asn Gly Leu Thr Val Leu Pro Pro Leu
850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
                900                 905                 910

Gln Asn Val Leu Tyr Glu Asn Gln Lys Leu Ile Ala Asn Gln Phe Asn
                915                 920                 925

Ser Ala Ile Gly Lys Ile Gln Asp Ser Leu Ser Ser Thr Ala Ser Ala
930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
                980                 985                 990

Ile Asp Arg Leu Ile Thr Gly Arg  Leu Gln Ser Leu Gln  Thr Tyr Val
            995                 1000                1005

Thr Gln Gln Leu Ile Arg Ala  Ala Glu Ile Arg Ala  Ser Ala Asn
     1010                1015                1020

Leu Ala Ala Thr Lys Met Ser  Glu Cys Val Leu Gly  Gln Ser Lys
     1025                1030                1035

Arg Val Asp Phe Cys Gly Lys  Gly Tyr His Leu Met  Ser Phe Pro
     1040                1045                1050

Gln Ser Ala Pro His Gly Val  Val Phe Leu His Val  Thr Tyr Val
     1055                1060                1065

Pro Ala Gln Glu Lys Asn Phe  Thr Thr Ala Pro Ala  Ile Cys His
     1070                1075                1080

Asp Gly Lys Ala His Phe Pro  Arg Glu Gly Val Phe  Val Ser Asn
     1085                1090                1095

Gly Thr His Trp Phe Val Thr  Gln Arg Asn Phe Tyr  Glu Pro Gln
     1100                1105                1110

Ile Ile Thr Thr Asp Asn Thr  Phe Val Ser Gly Asn  Cys Asp Val
     1115                1120                1125

Val Ile Gly Ile Val Asn Asn  Thr Val Tyr Asp Pro  Leu Gln Pro
     1130                1135                1140

Glu Leu Asp Ser Phe Lys Glu  Glu Leu Asp Lys Tyr  Phe Lys Asn
     1145                1150                1155

His Thr Ser Pro Asp Val Asp  Leu Gly Asp Ile Ser  Gly Ile Asn
     1160                1165                1170

Ala Ser Val Val Asn Ile Gln  Lys Glu Ile Asp Arg  Leu Asn Glu
     1175                1180                1185

Val Ala Lys Asn Leu Asn Glu  Ser Leu Ile Asp Leu  Gln Glu Leu
     1190                1195                1200

Gly Lys Tyr Glu Gln Tyr Ile  Lys Trp Pro Trp Tyr  Ile Trp Leu
     1205                1210                1215

Gly Phe Ile Ala Gly Leu Ile  Ala Ile Val Met Val  Thr Ile Met
     1220                1225                1230

Leu Cys Cys Met Thr Ser Cys  Cys Ser Cys Leu Lys  Gly Cys Cys
     1235                1240                1245
```

```
Ser Cys Gly Ser Cys Cys Lys Phe Asp Glu Asp Asp Ser Glu Pro
    1250                1255                1260

Val Leu Lys Gly Val Lys Leu His Tyr Thr
    1265                1270
```

<210> SEQ ID NO 3
<211> LENGTH: 196
<212> TYPE: PRT
<213> ORGANISM: SARS-COV-2
<220> FEATURE:
<221> NAME/KEY: MISC_FEATURE
<222> LOCATION: (1)..(196)
<223> OTHER INFORMATION: Receptor binding domain (CRBD; residues 330-521 of the spike protein)

<400> SEQUENCE: 3

```
Pro Asn Ile Thr Asn Leu Cys Pro Phe Gly Glu Val Phe Asn Ala Thr
1               5                   10                  15

Arg Phe Ala Ser Val Tyr Ala Trp Asn Arg Lys Arg Ile Ser Asn Cys
                20                  25                  30

Val Ala Asp Tyr Ser Val Leu Tyr Asn Ser Ala Ser Phe Ser Thr Phe
            35                  40                  45

Lys Cys Tyr Gly Val Ser Pro Thr Lys Leu Asn Asp Leu Cys Phe Thr
    50                  55                  60

Asn Val Tyr Ala Asp Ser Phe Val Ile Arg Gly Asp Glu Val Arg Gln
65                  70                  75                  80

Ile Ala Pro Gly Gln Thr Gly Lys Ile Ala Asp Tyr Asn Tyr Lys Leu
                85                  90                  95

Pro Asp Asp Phe Thr Gly Cys Val Ile Ala Trp Asn Ser Asn Asn Leu
            100                 105                 110

Asp Ser Lys Val Gly Gly Asn Tyr Asn Tyr Leu Tyr Arg Leu Phe Arg
        115                 120                 125

Lys Ser Asn Leu Lys Pro Phe Glu Arg Asp Ile Ser Thr Glu Ile Tyr
    130                 135                 140

Gln Ala Gly Ser Thr Pro Cys Asn Gly Val Glu Gly Phe Asn Cys Tyr
145                 150                 155                 160

Phe Pro Leu Gln Ser Tyr Gly Phe Gln Pro Thr Asn Gly Val Gly Tyr
                165                 170                 175

Gln Pro Tyr Arg Val Val Val Leu Ser Phe Glu Leu Leu His Ala Pro
            180                 185                 190

Ala Thr Val Cys
        195
```

<210> SEQ ID NO 4
<211> LENGTH: 1315
<212> TYPE: PRT
<213> ORGANISM: Artificial Sequence
<220> FEATURE:
<223> OTHER INFORMATION: Synthetic - Modified tetanus toxin (MTT) polypeptide "2MTT"

<400> SEQUENCE: 4

```
Met Pro Ile Thr Ile Asn Asn Phe Arg Tyr Ser Asp Pro Val Asn Asn
1               5                   10                  15

Asp Thr Ile Ile Met Met Glu Pro Pro Tyr Cys Lys Gly Leu Asp Ile
                20                  25                  30

Tyr Tyr Lys Ala Phe Lys Ile Thr Asp Arg Ile Trp Ile Val Pro Glu
            35                  40                  45

Arg Tyr Glu Phe Gly Thr Lys Pro Glu Asp Phe Asn Pro Pro Ser Ser
```

```
            50                  55                  60
Leu Ile Glu Gly Ala Ser Glu Tyr Tyr Asp Pro Asn Tyr Leu Arg Thr
 65                  70                  75                  80

Asp Ser Asp Lys Asp Arg Phe Leu Gln Thr Met Val Lys Leu Phe Asn
                 85                  90                  95

Arg Ile Lys Asn Asn Val Ala Gly Glu Ala Leu Leu Asp Lys Ile Ile
                100                 105                 110

Asn Ala Ile Pro Tyr Leu Gly Asn Ser Tyr Ser Leu Leu Asp Lys Phe
                115                 120                 125

Asp Thr Asn Ser Asn Ser Val Ser Phe Asn Leu Leu Glu Gln Asp Pro
                130                 135                 140

Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
                165                 170                 175

Arg Val Asp Asn Lys Asn Tyr Phe Pro Cys Arg Asp Gly Phe Gly Ser
                180                 185                 190

Ile Met Gln Met Ala Phe Cys Pro Glu Tyr Val Pro Thr Phe Asp Asn
                195                 200                 205

Val Ile Glu Asn Ile Thr Ser Leu Thr Ile Gly Lys Ser Lys Tyr Phe
210                 215                 220

Gln Asp Pro Ala Leu Leu Leu Met His Glu Leu Ile His Val Leu His
225                 230                 235                 240

Gly Leu Tyr Gly Met Gln Val Ser Ser His Glu Ile Ile Pro Ser Lys
                245                 250                 255

Gln Glu Ile Tyr Met Gln His Thr Tyr Pro Ile Ser Ala Glu Glu Leu
                260                 265                 270

Phe Thr Phe Gly Gly Gln Asp Ala Asn Leu Ile Ser Ile Asp Ile Lys
                275                 280                 285

Asn Asp Leu Tyr Glu Lys Thr Leu Asn Asp Tyr Lys Ala Ile Ala Asn
                290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
                325                 330                 335

Asn Gly Gln Tyr Ile Val Asn Glu Asp Lys Phe Gln Ile Leu Tyr Asn
                340                 345                 350

Ser Ile Met Tyr Gly Phe Thr Glu Ile Glu Leu Gly Lys Lys Phe Asn
                355                 360                 365

Ile Lys Thr Ala Leu Ser Phe Phe Ser Met Asn His Asp Pro Val Lys
370                 375                 380

Ile Pro Asn Leu Leu Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
                405                 410                 415

Arg Val Asn Thr Asn Ala Phe Arg Asn Val Asp Gly Ser Gly Leu Val
                420                 425                 430

Ser Lys Leu Ile Gly Leu Cys Lys Lys Ile Ile Pro Pro Thr Asn Ile
                435                 440                 445

Arg Glu Asn Leu Tyr Asn Arg Thr Ala Ser Leu Thr Asp Leu Gly Gly
                450                 455                 460

Glu Leu Cys Ile Lys Ile Lys Asn Glu Asp Leu Thr Phe Ile Ala Glu
465                 470                 475                 480
```

-continued

```
Lys Asn Ser Phe Ser Glu Glu Pro Phe Gln Asp Glu Ile Val Ser Tyr
            485                 490                 495
Asn Thr Lys Asn Lys Pro Leu Asn Phe Asn Tyr Ser Leu Asp Lys Ile
        500                 505                 510
Ile Val Asp Tyr Asn Leu Gln Ser Lys Ile Thr Leu Pro Asn Asp Arg
    515                 520                 525
Thr Thr Pro Val Thr Lys Gly Ile Pro Tyr Ala Pro Glu Tyr Lys Ser
530                 535                 540
Asn Ala Ala Ser Thr Ile Glu Ile His Asn Ile Asp Asp Asn Thr Ile
545                 550                 555                 560
Tyr Gln Tyr Leu Tyr Ala Gln Lys Ser Pro Thr Thr Leu Gln Arg Ile
            565                 570                 575
Thr Met Thr Asn Ser Val Asp Asp Ala Leu Ile Asn Ser Thr Lys Ile
        580                 585                 590
Tyr Ser Tyr Phe Pro Ser Val Ile Ser Lys Val Asn Gln Gly Ala Gln
    595                 600                 605
Gly Ile Leu Phe Leu Gln Trp Val Arg Asp Ile Ile Asp Asp Phe Thr
610                 615                 620
Asn Glu Ser Ser Gln Lys Thr Thr Ile Asp Lys Ile Ser Asp Val Ser
625                 630                 635                 640
Thr Ile Val Pro Tyr Ile Gly Pro Ala Leu Asn Ile Val Lys Gln Gly
            645                 650                 655
Tyr Glu Gly Asn Phe Ile Gly Ala Leu Glu Thr Thr Gly Val Val Leu
        660                 665                 670
Leu Leu Glu Tyr Ile Pro Glu Ile Thr Leu Pro Val Ile Ala Ala Leu
    675                 680                 685
Ser Ile Ala Glu Ser Ser Thr Gln Lys Glu Lys Ile Ile Lys Thr Ile
690                 695                 700
Asp Asn Phe Leu Glu Lys Arg Tyr Glu Lys Trp Ile Glu Val Tyr Lys
705                 710                 715                 720
Leu Val Lys Ala Lys Trp Leu Gly Thr Val Asn Thr Gln Phe Gln Lys
            725                 730                 735
Arg Ser Tyr Gln Met Tyr Arg Ser Leu Glu Tyr Gln Val Asp Ala Ile
        740                 745                 750
Lys Lys Ile Ile Asp Tyr Glu Tyr Lys Ile Tyr Ser Gly Pro Asp Lys
    755                 760                 765
Glu Gln Ile Ala Asp Glu Ile Asn Asn Leu Lys Asn Lys Leu Glu Glu
770                 775                 780
Lys Ala Asn Lys Ala Met Ile Asn Ile Asn Ile Phe Met Arg Glu Ser
785                 790                 795                 800
Ser Arg Ser Phe Leu Val Asn Gln Met Ile Asn Glu Ala Lys Lys Gln
            805                 810                 815
Leu Leu Glu Phe Asp Thr Gln Ser Lys Asn Ile Leu Met Gln Tyr Ile
        820                 825                 830
Lys Ala Asn Ser Lys Phe Ile Gly Ile Thr Glu Leu Lys Lys Leu Glu
    835                 840                 845
Ser Lys Ile Asn Lys Val Phe Ser Thr Pro Ile Pro Phe Ser Tyr Ser
850                 855                 860
Lys Asn Leu Asp Cys Trp Val Asp Asn Glu Glu Asp Ile Asp Val Ile
865                 870                 875                 880
Leu Lys Lys Ser Thr Ile Leu Asn Leu Asp Ile Asn Asn Asp Ile Ile
            885                 890                 895
```

-continued

```
Ser Asp Ile Ser Gly Phe Asn Ser Ser Val Ile Thr Tyr Pro Asp Ala
            900                 905                 910

Gln Leu Val Pro Gly Ile Asn Gly Lys Ala Ile His Leu Val Asn Asn
        915                 920                 925

Glu Ser Ser Glu Val Ile Val His Lys Ala Met Asp Ile Glu Tyr Asn
    930                 935                 940

Asp Met Phe Asn Asn Phe Thr Val Ser Phe Trp Leu Arg Val Pro Lys
945                 950                 955                 960

Val Ser Ala Ser His Leu Glu Gln Tyr Gly Thr Asn Glu Tyr Ser Ile
                965                 970                 975

Ile Ser Ser Met Lys Lys His Ser Leu Ser Ile Gly Ser Gly Trp Ser
            980                 985                 990

Val Ser Leu Lys Gly Asn Asn Leu Ile Trp Thr Leu Lys Asp Ser Ala
        995                 1000                1005

Gly Glu Val Arg Gln Ile Thr Phe Arg Asp Leu Pro Asp Lys Phe
    1010                1015                1020

Asn Ala Tyr Leu Ala Asn Lys Trp Val Phe Ile Thr Ile Thr Asn
    1025                1030                1035

Asp Arg Leu Ser Ser Ala Asn Leu Tyr Ile Asn Gly Val Leu Met
    1040                1045                1050

Gly Ser Ala Glu Ile Thr Gly Leu Gly Ala Ile Arg Glu Asp Asn
    1055                1060                1065

Asn Ile Thr Leu Lys Leu Asp Arg Cys Asn Asn Asn Asn Gln Tyr
    1070                1075                1080

Val Ser Ile Asp Lys Phe Arg Ile Phe Cys Lys Ala Leu Asn Pro
    1085                1090                1095

Lys Glu Ile Glu Lys Leu Tyr Thr Ser Tyr Leu Ser Ile Thr Phe
    1100                1105                1110

Leu Arg Asp Phe Trp Gly Asn Pro Leu Arg Tyr Asp Thr Glu Tyr
    1115                1120                1125

Tyr Leu Ile Pro Val Ala Ser Ser Ser Lys Asp Val Gln Leu Lys
    1130                1135                1140

Asn Ile Thr Asp Tyr Met Tyr Leu Thr Asn Ala Pro Ser Tyr Thr
    1145                1150                1155

Asn Gly Lys Leu Asn Ile Tyr Tyr Arg Arg Leu Tyr Asn Gly Leu
    1160                1165                1170

Lys Phe Ile Ile Lys Arg Tyr Thr Pro Asn Asn Glu Ile Asp Ser
    1175                1180                1185

Phe Val Lys Ser Gly Asp Phe Ile Lys Leu Tyr Val Ser Tyr Asn
    1190                1195                1200

Asn Asn Glu His Ile Val Gly Tyr Pro Lys Asp Gly Asn Ala Phe
    1205                1210                1215

Asn Asn Leu Asp Arg Ile Leu Arg Val Gly Tyr Asn Ala Pro Gly
    1220                1225                1230

Ile Pro Leu Tyr Lys Lys Met Glu Ala Val Lys Leu Arg Asp Leu
    1235                1240                1245

Lys Thr Tyr Ser Val Gln Leu Lys Leu Tyr Asp Asp Lys Asn Ala
    1250                1255                1260

Ser Leu Gly Leu Val Gly Thr His Asn Gly Gln Ile Gly Asn Asp
    1265                1270                1275

Pro Asn Arg Asp Ile Leu Ile Ala Ser Asn Trp Tyr Phe Asn His
    1280                1285                1290

Leu Lys Asp Lys Ile Leu Gly Cys Asp Trp Tyr Phe Val Pro Thr
```

```
            1295                1300                1305

Asp Glu  Gly Trp Thr Asn Asp
    1310               1315

<210> SEQ ID NO 5
<211> LENGTH: 1315
<212> TYPE: PRT
<213> ORGANISM: Artificial Sequence
<220> FEATURE:
<223> OTHER INFORMATION: Synthetic - Modified tetanus toxin (MTT)
      polypeptide "5MTT"

<400> SEQUENCE: 5

Met Pro Ile Thr Ile Asn Asn Phe Arg Tyr Ser Asp Pro Val Asn Asn
1               5                   10                  15

Asp Thr Ile Ile Met Met Glu Pro Pro Tyr Cys Lys Gly Leu Asp Ile
            20                  25                  30

Tyr Tyr Lys Ala Phe Lys Ile Thr Asp Arg Ile Trp Ile Val Pro Glu
        35                  40                  45

Arg Tyr Glu Phe Gly Thr Lys Pro Glu Asp Phe Asn Pro Pro Ser Ser
    50                  55                  60

Leu Ile Glu Gly Ala Ser Glu Tyr Tyr Asp Pro Asn Tyr Leu Arg Thr
65                  70                  75                  80

Asp Ser Asp Lys Asp Arg Phe Leu Gln Thr Met Val Lys Leu Phe Asn
                85                  90                  95

Arg Ile Lys Asn Asn Val Ala Gly Glu Ala Leu Leu Asp Lys Ile Ile
            100                 105                 110

Asn Ala Ile Pro Tyr Leu Gly Asn Ser Tyr Ser Leu Leu Asp Lys Phe
        115                 120                 125

Asp Thr Asn Ser Asn Ser Val Ser Phe Asn Leu Leu Glu Gln Asp Pro
    130                 135                 140

Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
                165                 170                 175

Arg Val Asp Asn Lys Asn Tyr Phe Pro Cys Arg Asp Gly Phe Gly Ser
            180                 185                 190

Ile Met Gln Met Ala Phe Cys Pro Glu Tyr Val Pro Thr Phe Asp Asn
        195                 200                 205

Val Ile Glu Asn Ile Thr Ser Leu Thr Ile Gly Lys Ser Lys Tyr Phe
    210                 215                 220

Gln Asp Pro Ala Leu Leu Leu Met His Gln Leu Ile His Val Leu His
225                 230                 235                 240

Gly Leu Tyr Gly Met Gln Val Ser Ser His Glu Ile Ile Pro Ser Lys
                245                 250                 255

Gln Glu Ile Tyr Met Gln His Thr Tyr Pro Ile Ser Ala Glu Glu Leu
            260                 265                 270

Phe Thr Phe Gly Gly Gln Asp Ala Asn Leu Ile Ser Ile Asp Ile Lys
        275                 280                 285

Asn Asp Leu Tyr Glu Lys Thr Leu Asn Asp Tyr Lys Ala Ile Ala Asn
    290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
                325                 330                 335
```

```
Asn Gly Gln Tyr Ile Val Asn Glu Asp Lys Phe Gln Ile Leu Tyr Asn
            340                 345                 350

Ser Ile Met Tyr Gly Phe Thr Glu Ile Glu Leu Gly Lys Lys Phe Asn
            355                 360                 365

Ile Lys Thr Ala Leu Ser Phe Phe Ser Met Asn His Asp Pro Val Lys
            370                 375             380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
                405                 410                 415

Arg Val Asn Thr Asn Ala Phe Arg Asn Val Asp Gly Ser Gly Leu Val
            420                 425                 430

Ser Lys Leu Ile Gly Leu Cys Lys Lys Ile Ile Pro Pro Thr Asn Ile
            435                 440                 445

Arg Glu Asn Leu Tyr Asn Arg Thr Ala Ser Leu Thr Asp Leu Gly Gly
            450                 455                 460

Glu Leu Cys Ile Lys Ile Lys Asn Glu Asp Leu Thr Phe Ile Ala Glu
465                 470                 475                 480

Lys Asn Ser Phe Ser Glu Glu Pro Phe Gln Asp Glu Ile Val Ser Tyr
                485                 490                 495

Asn Thr Lys Asn Lys Pro Leu Asn Phe Asn Tyr Ser Leu Asp Lys Ile
            500                 505                 510

Ile Val Asp Tyr Asn Leu Gln Ser Lys Ile Thr Leu Pro Asn Asp Arg
            515                 520                 525

Thr Thr Pro Val Thr Lys Gly Ile Pro Tyr Ala Pro Glu Tyr Lys Ser
            530                 535                 540

Asn Ala Ala Ser Thr Ile Glu Ile His Asn Ile Asp Asp Asn Thr Ile
545                 550                 555                 560

Tyr Gln Tyr Leu Tyr Ala Gln Lys Ser Pro Thr Thr Leu Gln Arg Ile
                565                 570                 575

Thr Met Thr Asn Ser Val Asp Asp Ala Leu Ile Asn Ser Thr Lys Ile
            580                 585                 590

Tyr Ser Tyr Phe Pro Ser Val Ile Ser Lys Val Asn Gln Gly Ala Gln
            595                 600                 605

Gly Ile Leu Phe Leu Gln Trp Val Arg Asp Ile Ile Asp Asp Phe Thr
            610                 615                 620

Asn Glu Ser Ser Gln Lys Thr Thr Ile Asp Lys Ile Ser Asp Val Ser
625                 630                 635                 640

Thr Ile Val Pro Tyr Ile Gly Pro Ala Leu Asn Ile Val Lys Gln Gly
                645                 650                 655

Tyr Glu Gly Asn Phe Ile Gly Ala Leu Glu Thr Thr Gly Val Val Leu
            660                 665                 670

Leu Leu Glu Tyr Ile Pro Glu Ile Thr Leu Pro Val Ile Ala Ala Leu
            675                 680                 685

Ser Ile Ala Glu Ser Ser Thr Gln Lys Glu Lys Ile Ile Lys Thr Ile
            690                 695                 700

Asp Asn Phe Leu Glu Lys Arg Tyr Glu Lys Trp Ile Glu Val Tyr Lys
705                 710                 715                 720

Leu Val Lys Ala Lys Trp Leu Gly Thr Val Asn Thr Gln Phe Gln Lys
                725                 730                 735

Arg Ser Tyr Gln Met Tyr Arg Ser Leu Glu Tyr Gln Val Asp Ala Ile
            740                 745                 750

Lys Lys Ile Ile Asp Tyr Glu Tyr Lys Ile Tyr Ser Gly Pro Asp Lys
```

-continued

```
            755                 760                 765
Glu Gln Ile Ala Asp Glu Ile Asn Asn Leu Lys Asn Lys Leu Glu Glu
            770                 775                 780
Lys Ala Asn Lys Ala Met Ile Asn Ile Asn Ile Phe Met Arg Glu Ser
785                 790                 795                 800
Ser Arg Ser Phe Leu Val Asn Gln Met Ile Asn Glu Ala Lys Lys Gln
                    805                 810                 815
Leu Leu Glu Phe Asp Thr Gln Ser Lys Asn Ile Leu Met Gln Tyr Ile
                    820                 825                 830
Lys Ala Asn Ser Lys Phe Ile Gly Ile Thr Glu Leu Lys Lys Leu Glu
                    835                 840                 845
Ser Lys Ile Asn Lys Val Phe Ser Thr Pro Ile Pro Phe Ser Tyr Ser
            850                 855                 860
Lys Asn Leu Asp Cys Trp Val Asp Asn Glu Glu Asp Ile Asp Val Ile
865                 870                 875                 880
Leu Lys Lys Ser Thr Ile Leu Asn Leu Asp Ile Asn Asn Asp Ile Ile
                    885                 890                 895
Ser Asp Ile Ser Gly Phe Asn Ser Ser Val Ile Thr Tyr Pro Asp Ala
                    900                 905                 910
Gln Leu Val Pro Gly Ile Asn Gly Lys Ala Ile His Leu Val Asn Asn
            915                 920                 925
Glu Ser Ser Glu Val Ile Val His Lys Ala Met Asp Ile Glu Tyr Asn
            930                 935                 940
Asp Met Phe Asn Asn Phe Thr Val Ser Phe Trp Leu Arg Val Pro Lys
945                 950                 955                 960
Val Ser Ala Ser His Leu Glu Gln Tyr Gly Thr Asn Glu Tyr Ser Ile
                    965                 970                 975
Ile Ser Ser Met Lys Lys His Ser Leu Ser Ile Gly Ser Gly Trp Ser
                    980                 985                 990
Val Ser Leu Lys Gly Asn Asn Leu Ile Trp Thr Leu Lys Asp Ser Ala
            995                 1000                1005
Gly Glu Val Arg Gln Ile Thr Phe Arg Asp Leu Pro Asp Lys Phe
            1010                1015                1020
Asn Ala Tyr Leu Ala Asn Lys Trp Val Phe Ile Thr Ile Thr Asn
            1025                1030                1035
Asp Arg Leu Ser Ser Ala Asn Leu Tyr Ile Asn Gly Val Leu Met
            1040                1045                1050
Gly Ser Ala Glu Ile Thr Gly Leu Gly Ala Ile Arg Glu Asp Asn
            1055                1060                1065
Asn Ile Thr Leu Lys Leu Asp Arg Cys Asn Asn Asn Asn Gln Tyr
            1070                1075                1080
Val Ser Ile Asp Lys Phe Arg Ile Phe Cys Lys Ala Leu Asn Pro
            1085                1090                1095
Lys Glu Ile Glu Lys Leu Tyr Thr Ser Tyr Leu Ser Ile Thr Phe
            1100                1105                1110
Leu Arg Asp Phe Trp Gly Asn Pro Leu Arg Tyr Asp Thr Glu Tyr
            1115                1120                1125
Tyr Leu Ile Pro Val Ala Ser Ser Ser Lys Asp Val Gln Leu Lys
            1130                1135                1140
Asn Ile Thr Asp Tyr Met Tyr Leu Thr Asn Ala Pro Ser Tyr Thr
            1145                1150                1155
Asn Gly Lys Leu Asn Ile Tyr Tyr Arg Arg Leu Tyr Asn Gly Leu
            1160                1165                1170
```

```
Lys Phe Ile Ile Lys Arg Tyr Thr Pro Asn Asn Glu Ile Asp Ser
    1175                1180                1185

Phe Val Lys Ser Gly Asp Phe Ile Lys Leu Tyr Val Ser Tyr Asn
    1190                1195                1200

Asn Asn Glu His Ile Val Gly Tyr Pro Lys Asp Gly Asn Ala Phe
    1205                1210                1215

Asn Asn Leu Asp Arg Ile Leu Leu Val Gly Tyr Asn Ala Pro Gly
    1220                1225                1230

Ile Pro Leu Tyr Lys Lys Met Glu Ala Val Lys Leu Arg Asp Leu
    1235                1240                1245

Lys Thr Tyr Ser Val Gln Leu Lys Leu Tyr Asp Asp Lys Asn Ala
    1250                1255                1260

Ser Leu Gly Leu Val Gly Thr His Asn Gly Gln Ile Gly Asn Asp
    1265                1270                1275

Pro Asn Arg Asp Ile Leu Ile Ala Ser Asn Ala Tyr Phe Asn His
    1280                1285                1290

Leu Lys Asp Lys Ile Leu Gly Cys Asp Trp Tyr Phe Val Pro Thr
    1295                1300                1305

Asp Glu Gly Trp Thr Asn Asp
    1310                1315

<210> SEQ ID NO 6
<211> LENGTH: 1315
<212> TYPE: PRT
<213> ORGANISM: Artificial Sequence
<220> FEATURE:
<223> OTHER INFORMATION: Synthetic - Modified tetanus toxin (MTT)
      polypeptide "6MTT"

<400> SEQUENCE: 6

Met Pro Ile Thr Ile Asn Asn Phe Arg Tyr Ser Asp Pro Val Asn
1               5                   10                  15

Asp Thr Ile Ile Met Met Glu Pro Pro Tyr Cys Lys Gly Leu Asp Ile
                20                  25                  30

Tyr Tyr Lys Ala Phe Lys Ile Thr Asp Arg Ile Trp Ile Val Pro Glu
    35                  40                  45

Arg Tyr Glu Phe Gly Thr Lys Pro Glu Asp Phe Asn Pro Pro Ser Ser
    50                  55                  60

Leu Ile Glu Gly Ala Ser Glu Tyr Tyr Asp Pro Asn Tyr Leu Arg Thr
65                  70                  75                  80

Asp Ser Asp Lys Asp Arg Phe Leu Gln Thr Met Val Lys Leu Phe Asn
                85                  90                  95

Arg Ile Lys Asn Asn Val Ala Gly Glu Ala Leu Leu Asp Lys Ile Ile
                100                 105                 110

Asn Ala Ile Pro Tyr Leu Gly Asn Ser Tyr Ser Leu Leu Asp Lys Phe
        115                 120                 125

Asp Thr Asn Ser Asn Ser Val Ser Phe Asn Leu Leu Glu Gln Asp Pro
    130                 135                 140

Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
                165                 170                 175

Arg Val Asp Asn Lys Asn Tyr Phe Pro Cys Arg Asp Gly Phe Gly Ser
                180                 185                 190

Ile Met Gln Met Ala Phe Cys Pro Glu Tyr Val Pro Thr Phe Asp Asn
```

```
            195                 200                 205
Val Ile Glu Asn Ile Thr Ser Leu Thr Ile Gly Lys Ser Lys Tyr Phe
210                 215                 220

Gln Asp Pro Ala Leu Leu Leu Met His Gln Leu Ile His Val Leu His
225                 230                 235                 240

Gly Leu Tyr Gly Met Gln Val Ser Ser His Glu Ile Ile Pro Ser Lys
                245                 250                 255

Gln Glu Ile Tyr Met Gln His Thr Tyr Pro Ile Ser Ala Glu Glu Leu
                260                 265                 270

Phe Thr Phe Gly Gly Gln Asp Ala Asn Leu Ile Ser Ile Asp Ile Lys
                275                 280                 285

Asn Asp Leu Tyr Glu Lys Thr Leu Asn Asp Tyr Lys Ala Ile Ala Asn
290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
                325                 330                 335

Asn Gly Gln Tyr Ile Val Asn Glu Asp Lys Phe Gln Ile Leu Tyr Asn
                340                 345                 350

Ser Ile Met Tyr Gly Phe Thr Glu Ile Glu Leu Gly Lys Lys Phe Asn
            355                 360                 365

Ile Lys Thr Ala Leu Ser Phe Phe Ser Met Asn His Asp Pro Val Lys
370                 375                 380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
                405                 410                 415

Arg Val Asn Thr Asn Ala Phe Arg Asn Val Asp Gly Ser Gly Leu Val
                420                 425                 430

Ser Lys Leu Ile Gly Leu Cys Lys Lys Ile Ile Pro Pro Thr Asn Ile
            435                 440                 445

Arg Glu Asn Leu Tyr Asn Arg Thr Ala Ser Leu Thr Asp Leu Gly Gly
450                 455                 460

Glu Leu Cys Ile Lys Ile Lys Asn Glu Asp Leu Thr Phe Ile Ala Glu
465                 470                 475                 480

Lys Asn Ser Phe Ser Glu Glu Pro Phe Gln Asp Glu Ile Val Ser Tyr
                485                 490                 495

Asn Thr Lys Asn Lys Pro Leu Asn Phe Asn Tyr Ser Leu Asp Lys Ile
                500                 505                 510

Ile Val Asp Tyr Asn Leu Gln Ser Lys Ile Thr Leu Pro Asn Asp Arg
            515                 520                 525

Thr Thr Pro Val Thr Lys Gly Ile Pro Tyr Ala Pro Glu Tyr Lys Ser
            530                 535                 540

Asn Ala Ala Ser Thr Ile Glu Ile His Asn Ile Asp Asp Asn Thr Ile
545                 550                 555                 560

Tyr Gln Tyr Leu Tyr Ala Gln Lys Ser Pro Thr Thr Leu Gln Arg Ile
                565                 570                 575

Thr Met Thr Asn Ser Val Asp Asp Ala Leu Ile Asn Ser Thr Lys Ile
                580                 585                 590

Tyr Ser Tyr Phe Pro Ser Val Ile Ser Lys Val Asn Gln Gly Ala Gln
            595                 600                 605

Gly Ile Leu Phe Leu Gln Trp Val Arg Asp Ile Ile Asp Asp Phe Thr
            610                 615                 620
```

```
Asn Glu Ser Ser Gln Lys Thr Thr Ile Asp Lys Ile Ser Asp Val Ser
625                 630                 635                 640

Thr Ile Val Pro Tyr Ile Gly Pro Ala Leu Asn Ile Val Lys Gln Gly
            645                 650                 655

Tyr Glu Gly Asn Phe Ile Gly Ala Leu Glu Thr Thr Gly Val Val Leu
                660                 665                 670

Leu Leu Glu Tyr Ile Pro Glu Ile Thr Leu Pro Val Ile Ala Ala Leu
            675                 680                 685

Ser Ile Ala Glu Ser Ser Thr Gln Lys Glu Lys Ile Ile Lys Thr Ile
690                 695                 700

Asp Asn Phe Leu Glu Lys Arg Tyr Glu Lys Trp Ile Glu Val Tyr Lys
705                 710                 715                 720

Leu Val Lys Ala Lys Trp Leu Gly Thr Val Asn Thr Gln Phe Gln Lys
                725                 730                 735

Arg Ser Tyr Gln Met Tyr Arg Ser Leu Glu Tyr Gln Val Asp Ala Ile
            740                 745                 750

Lys Lys Ile Ile Asp Tyr Glu Tyr Lys Ile Tyr Ser Gly Pro Asp Ala
            755                 760                 765

Glu Gln Ile Ala Asp Glu Ile Asn Asn Leu Lys Asn Lys Leu Glu Glu
770                 775                 780

Lys Ala Asn Lys Ala Met Ile Asn Ile Asn Ile Phe Met Arg Glu Ser
785                 790                 795                 800

Ser Arg Ser Phe Leu Val Asn Gln Met Ile Asn Glu Ala Lys Lys Gln
                805                 810                 815

Leu Leu Glu Phe Asp Thr Gln Ser Lys Asn Ile Leu Met Gln Tyr Ile
            820                 825                 830

Lys Ala Asn Ser Lys Phe Ile Gly Ile Thr Glu Leu Lys Lys Leu Glu
            835                 840                 845

Ser Lys Ile Asn Lys Val Phe Ser Thr Pro Ile Pro Phe Ser Tyr Ser
850                 855                 860

Lys Asn Leu Asp Cys Trp Val Asp Asn Glu Glu Asp Ile Asp Val Ile
865                 870                 875                 880

Leu Lys Lys Ser Thr Ile Leu Asn Leu Asp Ile Asn Asn Asp Ile Ile
                885                 890                 895

Ser Asp Ile Ser Gly Phe Asn Ser Ser Val Ile Thr Tyr Pro Asp Ala
            900                 905                 910

Gln Leu Val Pro Gly Ile Asn Gly Lys Ala Ile His Leu Val Asn Asn
            915                 920                 925

Glu Ser Ser Glu Val Ile Val His Lys Ala Met Asp Ile Glu Tyr Asn
930                 935                 940

Asp Met Phe Asn Asn Phe Thr Val Ser Phe Trp Leu Arg Val Pro Lys
945                 950                 955                 960

Val Ser Ala Ser His Leu Glu Gln Tyr Gly Thr Asn Glu Tyr Ser Ile
                965                 970                 975

Ile Ser Ser Met Lys Lys His Ser Leu Ser Ile Gly Ser Gly Trp Ser
            980                 985                 990

Val Ser Leu Lys Gly Asn Asn Leu Ile Trp Thr Leu Lys Asp Ser Ala
            995                 1000                1005

Gly Glu Val Arg Gln Ile Thr Phe Arg Asp Leu Pro Asp Lys Phe
        1010                1015                1020

Asn Ala Tyr Leu Ala Asn Lys Trp Val Phe Ile Thr Ile Thr Asn
        1025                1030                1035
```

```
Asp Arg Leu Ser Ser Ala Asn Leu Tyr Ile Asn Gly Val Leu Met
    1040                1045                1050

Gly Ser Ala Glu Ile Thr Gly Leu Gly Ala Ile Arg Glu Asp Asn
    1055                1060                1065

Asn Ile Thr Leu Lys Leu Asp Arg Cys Asn Asn Asn Gln Tyr
    1070                1075                1080

Val Ser Ile Asp Lys Phe Arg Ile Phe Cys Lys Ala Leu Asn Pro
    1085                1090                1095

Lys Glu Ile Glu Lys Leu Tyr Thr Ser Tyr Leu Ser Ile Thr Phe
    1100                1105                1110

Leu Arg Asp Phe Trp Gly Asn Pro Leu Arg Tyr Asp Thr Glu Tyr
    1115                1120                1125

Tyr Leu Ile Pro Val Ala Ser Ser Ser Lys Asp Val Gln Leu Lys
    1130                1135                1140

Asn Ile Thr Asp Tyr Met Tyr Leu Thr Asn Ala Pro Ser Tyr Thr
    1145                1150                1155

Asn Gly Lys Leu Asn Ile Tyr Tyr Arg Arg Leu Tyr Asn Gly Leu
    1160                1165                1170

Lys Phe Ile Ile Lys Arg Tyr Thr Pro Asn Asn Glu Ile Asp Ser
    1175                1180                1185

Phe Val Lys Ser Gly Asp Phe Ile Lys Leu Tyr Val Ser Tyr Asn
    1190                1195                1200

Asn Asn Glu His Ile Val Gly Tyr Pro Lys Asp Gly Asn Ala Phe
    1205                1210                1215

Asn Asn Leu Asp Arg Ile Leu Leu Val Gly Tyr Asn Ala Pro Gly
    1220                1225                1230

Ile Pro Leu Tyr Lys Lys Met Glu Ala Val Lys Leu Arg Asp Leu
    1235                1240                1245

Lys Thr Tyr Ser Val Gln Leu Lys Leu Tyr Asp Asp Lys Asn Ala
    1250                1255                1260

Ser Leu Gly Leu Val Gly Thr His Asn Gly Gln Ile Gly Asn Asp
    1265                1270                1275

Pro Asn Arg Asp Ile Leu Ile Ala Ser Asn Ala Tyr Phe Asn His
    1280                1285                1290

Leu Lys Asp Lys Ile Leu Gly Cys Asp Trp Tyr Phe Val Pro Thr
    1295                1300                1305

Asp Glu Gly Trp Thr Asn Asp
    1310                1315

<210> SEQ ID NO 7
<211> LENGTH: 1315
<212> TYPE: PRT
<213> ORGANISM: Artificial Sequence
<220> FEATURE:
<223> OTHER INFORMATION: Synthetic - Modified tetanus toxin (MTT)
      polypeptide "7MTT"

<400> SEQUENCE: 7

Met Pro Ile Thr Ile Asn Asn Phe Arg Tyr Ser Asp Pro Val Asn Asn
1               5                   10                  15

Asp Thr Ile Ile Met Met Glu Pro Pro Ala Cys Lys Gly Leu Asp Ile
                20                  25                  30

Tyr Tyr Lys Ala Phe Lys Ile Thr Asp Arg Ile Trp Ile Val Pro Glu
        35                  40                  45

Arg Tyr Glu Phe Gly Thr Lys Pro Glu Asp Phe Asn Pro Pro Ser Ser
    50                  55                  60
```

```
Leu Ile Glu Gly Ala Ser Glu Tyr Tyr Asp Pro Asn Tyr Leu Arg Thr
 65                  70                  75                  80

Asp Ser Asp Lys Asp Arg Phe Leu Gln Thr Met Val Lys Leu Phe Asn
                 85                  90                  95

Arg Ile Lys Asn Asn Val Ala Gly Glu Ala Leu Leu Asp Lys Ile Ile
            100                 105                 110

Asn Ala Ile Pro Tyr Leu Gly Asn Ser Tyr Ser Leu Leu Asp Lys Phe
            115                 120                 125

Asp Thr Asn Ser Asn Ser Val Ser Phe Asn Leu Leu Glu Gln Asp Pro
            130                 135                 140

Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
                165                 170                 175

Arg Val Asp Asn Lys Asn Tyr Phe Pro Cys Arg Asp Gly Phe Gly Ser
            180                 185                 190

Ile Met Gln Met Ala Phe Cys Pro Glu Tyr Val Pro Thr Phe Asp Asn
            195                 200                 205

Val Ile Glu Asn Ile Thr Ser Leu Thr Ile Gly Lys Ser Lys Tyr Phe
210                 215                 220

Gln Asp Pro Ala Leu Leu Leu Met His Gln Leu Ile His Val Leu His
225                 230                 235                 240

Gly Leu Tyr Gly Met Gln Val Ser Ser His Glu Ile Ile Pro Ser Lys
                245                 250                 255

Gln Glu Ile Tyr Met Gln His Thr Tyr Pro Ile Ser Ala Glu Glu Leu
            260                 265                 270

Phe Thr Phe Gly Gly Gln Asp Ala Asn Leu Ile Ser Ile Asp Ile Lys
            275                 280                 285

Asn Asp Leu Tyr Glu Lys Thr Leu Asn Asp Tyr Lys Ala Ile Ala Asn
            290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
                325                 330                 335

Asn Gly Gln Tyr Ile Val Asn Glu Asp Lys Phe Gln Ile Leu Tyr Asn
            340                 345                 350

Ser Ile Met Tyr Gly Phe Thr Glu Ile Glu Leu Gly Lys Lys Phe Asn
            355                 360                 365

Ile Lys Thr Ala Leu Ser Phe Phe Ser Met Asn His Asp Pro Val Lys
            370                 375                 380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
                405                 410                 415

Arg Val Asn Thr Asn Ala Phe Arg Asn Val Asp Gly Ser Gly Leu Val
            420                 425                 430

Ser Lys Leu Ile Gly Leu Cys Lys Lys Ile Ile Pro Pro Thr Asn Ile
            435                 440                 445

Arg Glu Asn Leu Tyr Asn Arg Thr Ala Ser Leu Thr Asp Leu Gly Gly
            450                 455                 460

Glu Leu Cys Ile Lys Ile Lys Asn Glu Asp Leu Thr Phe Ile Ala Glu
465                 470                 475                 480
```

-continued

```
Lys Asn Ser Phe Ser Glu Glu Pro Phe Gln Asp Glu Ile Val Ser Tyr
                485                 490                 495
Asn Thr Lys Asn Lys Pro Leu Asn Phe Asn Tyr Ser Leu Asp Lys Ile
            500                 505                 510
Ile Val Asp Tyr Asn Leu Gln Ser Lys Ile Thr Leu Pro Asn Asp Arg
        515                 520                 525
Thr Thr Pro Val Thr Lys Gly Ile Pro Tyr Ala Pro Glu Tyr Lys Ser
    530                 535                 540
Asn Ala Ala Ser Thr Ile Glu Ile His Asn Ile Asp Asp Asn Thr Ile
545                 550                 555                 560
Tyr Gln Tyr Leu Tyr Ala Gln Lys Ser Pro Thr Thr Leu Gln Arg Ile
                565                 570                 575
Thr Met Thr Asn Ser Val Asp Asp Ala Leu Ile Asn Ser Thr Lys Ile
            580                 585                 590
Tyr Ser Tyr Phe Pro Ser Val Ile Ser Lys Val Asn Gln Gly Ala Gln
        595                 600                 605
Gly Ile Leu Phe Leu Gln Trp Val Arg Asp Ile Ile Asp Asp Phe Thr
    610                 615                 620
Asn Glu Ser Ser Gln Lys Thr Thr Ile Asp Lys Ile Ser Asp Val Ser
625                 630                 635                 640
Thr Ile Val Pro Tyr Ile Gly Pro Ala Leu Asn Ile Val Lys Gln Gly
                645                 650                 655
Tyr Glu Gly Asn Phe Ile Gly Ala Leu Glu Thr Thr Gly Val Val Leu
            660                 665                 670
Leu Leu Glu Tyr Ile Pro Glu Ile Thr Leu Pro Val Ile Ala Ala Leu
        675                 680                 685
Ser Ile Ala Glu Ser Ser Thr Gln Lys Glu Lys Ile Ile Lys Thr Ile
    690                 695                 700
Asp Asn Phe Leu Glu Lys Arg Tyr Glu Lys Trp Ile Glu Val Tyr Lys
705                 710                 715                 720
Leu Val Lys Ala Lys Trp Leu Gly Thr Val Asn Thr Gln Phe Gln Lys
                725                 730                 735
Arg Ser Tyr Gln Met Tyr Arg Ser Leu Glu Tyr Gln Val Asp Ala Ile
            740                 745                 750
Lys Lys Ile Ile Asp Tyr Glu Tyr Lys Ile Tyr Ser Gly Pro Asp Ala
        755                 760                 765
Glu Gln Ile Ala Asp Glu Ile Asn Asn Leu Lys Asn Lys Leu Glu Glu
    770                 775                 780
Lys Ala Asn Lys Ala Met Ile Asn Ile Asn Ile Phe Met Arg Glu Ser
785                 790                 795                 800
Ser Arg Ser Phe Leu Val Asn Gln Met Ile Asn Glu Ala Lys Lys Gln
                805                 810                 815
Leu Leu Glu Phe Asp Thr Gln Ser Lys Asn Ile Leu Met Gln Tyr Ile
            820                 825                 830
Lys Ala Asn Ser Lys Phe Ile Gly Ile Thr Glu Leu Lys Lys Leu Glu
        835                 840                 845
Ser Lys Ile Asn Lys Val Phe Ser Thr Pro Ile Pro Phe Ser Tyr Ser
    850                 855                 860
Lys Asn Leu Asp Cys Trp Val Asp Asn Glu Glu Asp Ile Asp Val Ile
865                 870                 875                 880
Leu Lys Lys Ser Thr Ile Leu Asn Leu Asp Ile Asn Asn Asp Ile Ile
                885                 890                 895
Ser Asp Ile Ser Gly Phe Asn Ser Ser Val Ile Thr Tyr Pro Asp Ala
```

-continued

```
                900                 905                 910
Gln Leu Val Pro Gly Ile Asn Gly Lys Ala Ile His Leu Val Asn Asn
            915                 920                 925
Glu Ser Ser Glu Val Ile Val His Lys Ala Met Asp Ile Glu Tyr Asn
        930                 935                 940
Asp Met Phe Asn Asn Phe Thr Val Ser Phe Trp Leu Arg Val Pro Lys
945                 950                 955                 960
Val Ser Ala Ser His Leu Glu Gln Tyr Gly Thr Asn Glu Tyr Ser Ile
            965                 970                 975
Ile Ser Ser Met Lys Lys His Ser Leu Ser Ile Gly Ser Gly Trp Ser
                980                 985                 990
Val Ser Leu Lys Gly Asn Asn Leu Ile Trp Thr Leu Lys Asp Ser Ala
            995                 1000                1005
Gly Glu Val Arg Gln Ile Thr Phe Arg Asp Leu Pro Asp Lys Phe
        1010                1015                1020
Asn Ala Tyr Leu Ala Asn Lys Trp Val Phe Ile Thr Ile Thr Asn
        1025                1030                1035
Asp Arg Leu Ser Ser Ala Asn Leu Tyr Ile Asn Gly Val Leu Met
        1040                1045                1050
Gly Ser Ala Glu Ile Thr Gly Leu Gly Ala Ile Arg Glu Asp Asn
        1055                1060                1065
Asn Ile Thr Leu Lys Leu Asp Arg Cys Asn Asn Asn Gln Tyr
        1070                1075                1080
Val Ser Ile Asp Lys Phe Arg Ile Phe Cys Lys Ala Leu Asn Pro
        1085                1090                1095
Lys Glu Ile Glu Lys Leu Tyr Thr Ser Tyr Leu Ser Ile Thr Phe
        1100                1105                1110
Leu Arg Asp Phe Trp Gly Asn Pro Leu Arg Tyr Asp Thr Glu Tyr
        1115                1120                1125
Tyr Leu Ile Pro Val Ala Ser Ser Ser Lys Asp Val Gln Leu Lys
        1130                1135                1140
Asn Ile Thr Asp Tyr Met Tyr Leu Thr Asn Ala Pro Ser Tyr Thr
        1145                1150                1155
Asn Gly Lys Leu Asn Ile Tyr Tyr Arg Arg Leu Tyr Asn Gly Leu
        1160                1165                1170
Lys Phe Ile Ile Lys Arg Tyr Thr Pro Asn Asn Glu Ile Asp Ser
        1175                1180                1185
Phe Val Lys Ser Gly Asp Phe Ile Lys Leu Tyr Val Ser Tyr Asn
        1190                1195                1200
Asn Asn Glu His Ile Val Gly Tyr Pro Lys Asp Gly Asn Ala Phe
        1205                1210                1215
Asn Asn Leu Asp Arg Ile Leu Leu Val Gly Tyr Asn Ala Pro Gly
        1220                1225                1230
Ile Pro Leu Tyr Lys Lys Met Glu Ala Val Lys Leu Arg Asp Leu
        1235                1240                1245
Lys Thr Tyr Ser Val Gln Leu Lys Leu Tyr Asp Asp Lys Asn Ala
        1250                1255                1260
Ser Leu Gly Leu Val Gly Thr His Asn Gly Gln Ile Gly Asn Asp
        1265                1270                1275
Pro Asn Arg Asp Ile Leu Ile Ala Ser Asn Ala Tyr Phe Asn His
        1280                1285                1290
Leu Lys Asp Lys Ile Leu Gly Cys Asp Trp Tyr Phe Val Pro Thr
        1295                1300                1305
```

```
Asp Glu Gly Trp Thr Asn Asp
    1310            1315

<210> SEQ ID NO 8
<211> LENGTH: 1315
<212> TYPE: PRT
<213> ORGANISM: Artificial Sequence
<220> FEATURE:
<223> OTHER INFORMATION: Synthetic - Modified tetanus toxin (MTT)
      polypeptide "8MTT"

<400> SEQUENCE: 8

Met Pro Ile Thr Ile Asn Asn Phe Arg Tyr Ser Asp Pro Val Asn Asn
1               5                   10                  15

Asp Thr Ile Ile Met Met Glu Pro Pro Ala Cys Lys Gly Leu Asp Ile
            20                  25                  30

Tyr Tyr Lys Ala Phe Lys Ile Thr Asp Arg Ile Trp Ile Val Pro Glu
        35                  40                  45

Arg Tyr Glu Phe Gly Thr Lys Pro Glu Asp Phe Asn Pro Pro Ser Ser
    50                  55                  60

Leu Ile Glu Gly Ala Ser Glu Tyr Tyr Asp Pro Asn Tyr Leu Arg Thr
65                  70                  75                  80

Asp Ser Asp Lys Asp Arg Phe Leu Gln Thr Met Val Lys Leu Phe Asn
                85                  90                  95

Arg Ile Lys Asn Asn Val Ala Gly Glu Ala Leu Leu Asp Lys Ile Ile
            100                 105                 110

Asn Ala Ile Pro Tyr Leu Gly Asn Ser Tyr Ser Leu Leu Asp Lys Phe
        115                 120                 125

Asp Thr Asn Ser Asn Ser Val Ser Phe Asn Leu Leu Glu Gln Asp Pro
    130                 135                 140

Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
                165                 170                 175

Arg Val Asp Asn Lys Asn Tyr Phe Pro Cys Arg Asp Gly Phe Gly Ser
            180                 185                 190

Ile Met Gln Met Ala Phe Cys Pro Glu Tyr Val Pro Thr Phe Asp Asn
        195                 200                 205

Val Ile Glu Asn Ile Thr Ser Leu Thr Ile Gly Lys Ser Lys Tyr Phe
    210                 215                 220

Gln Asp Pro Ala Leu Leu Lys Met His Gln Leu Ile His Val Leu His
225                 230                 235                 240

Gly Leu Tyr Gly Met Gln Val Ser Ser His Glu Ile Ile Pro Ser Lys
                245                 250                 255

Gln Glu Ile Tyr Met Gln His Thr Tyr Pro Ile Ser Ala Glu Glu Leu
            260                 265                 270

Phe Thr Phe Gly Gly Gln Asp Ala Asn Leu Ile Ser Ile Asp Ile Lys
        275                 280                 285

Asn Asp Leu Tyr Glu Lys Thr Leu Asn Asp Tyr Lys Ala Ile Ala Asn
    290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
                325                 330                 335

Asn Gly Gln Tyr Ile Val Asn Glu Asp Lys Phe Gln Ile Leu Tyr Asn
```

```
              340              345              350
Ser Ile Met Tyr Gly Phe Thr Glu Ile Glu Leu Gly Lys Lys Phe Asn
            355              360              365

Ile Lys Thr Ala Leu Ser Phe Phe Ser Met Asn His Asp Pro Val Lys
            370              375              380

Ile Pro Asn Leu Leu Asp Asp Thr Ile Tyr Asn Asp Thr Glu Gly Phe
385              390              395              400

Asn Ile Glu Ser Lys Asp Leu Lys Ser Glu Tyr Lys Gly Gln Asn Met
                405              410              415

Arg Val Asn Thr Asn Ala Phe Arg Asn Val Asp Gly Ser Gly Leu Val
            420              425              430

Ser Lys Leu Ile Gly Leu Cys Lys Lys Ile Ile Pro Pro Thr Asn Ile
            435              440              445

Arg Glu Asn Leu Tyr Asn Arg Thr Ala Ser Leu Thr Asp Leu Gly Gly
            450              455              460

Glu Leu Cys Ile Lys Ile Lys Asn Glu Asp Leu Thr Phe Ile Ala Glu
465              470              475              480

Lys Asn Ser Phe Ser Glu Pro Phe Gln Asp Glu Ile Val Ser Tyr
                485              490              495

Asn Thr Lys Asn Lys Pro Leu Asn Phe Asn Tyr Ser Leu Asp Lys Ile
            500              505              510

Ile Val Asp Tyr Asn Leu Gln Ser Lys Ile Thr Leu Pro Asn Asp Arg
            515              520              525

Thr Thr Pro Val Thr Lys Gly Ile Pro Tyr Ala Pro Glu Tyr Lys Ser
            530              535              540

Asn Ala Ala Ser Thr Ile Glu Ile His Asn Ile Asp Asp Asn Thr Ile
545              550              555              560

Tyr Gln Tyr Leu Tyr Ala Gln Lys Ser Pro Thr Thr Leu Gln Arg Ile
                565              570              575

Thr Met Thr Asn Ser Val Asp Asp Ala Leu Ile Asn Ser Thr Lys Ile
            580              585              590

Tyr Ser Tyr Phe Pro Ser Val Ile Ser Lys Val Asn Gln Gly Ala Gln
            595              600              605

Gly Ile Leu Phe Leu Gln Trp Val Arg Asp Ile Ile Asp Asp Phe Thr
            610              615              620

Asn Glu Ser Ser Gln Lys Thr Thr Ile Asp Lys Ile Ser Asp Val Ser
625              630              635              640

Thr Ile Val Pro Tyr Ile Gly Pro Ala Leu Asn Ile Val Lys Gln Gly
                645              650              655

Tyr Glu Gly Asn Phe Ile Gly Ala Leu Glu Thr Thr Gly Val Val Leu
            660              665              670

Leu Leu Glu Tyr Ile Pro Glu Ile Thr Leu Pro Val Ile Ala Ala Leu
            675              680              685

Ser Ile Ala Glu Ser Ser Thr Gln Lys Glu Lys Ile Ile Lys Thr Ile
            690              695              700

Asp Asn Phe Leu Glu Lys Arg Tyr Glu Lys Trp Ile Glu Val Tyr Lys
705              710              715              720

Leu Val Lys Ala Lys Trp Leu Gly Thr Val Asn Thr Gln Phe Gln Lys
                725              730              735

Arg Ser Tyr Gln Met Tyr Arg Ser Leu Glu Tyr Gln Val Asp Ala Ile
            740              745              750

Lys Lys Ile Ile Asp Tyr Glu Tyr Lys Ile Tyr Ser Gly Pro Asp Ala
            755              760              765
```

```
Glu Gln Ile Ala Asp Glu Ile Asn Asn Leu Lys Asn Lys Leu Glu Glu
770                 775                 780

Lys Ala Asn Lys Ala Met Ile Asn Ile Asn Ile Phe Met Arg Glu Ser
785                 790                 795                 800

Ser Arg Ser Phe Leu Val Asn Gln Met Ile Asn Glu Ala Lys Lys Gln
                805                 810                 815

Leu Leu Glu Phe Asp Thr Gln Ser Lys Asn Ile Leu Met Gln Tyr Ile
                820                 825                 830

Lys Ala Asn Ser Lys Phe Ile Gly Ile Thr Glu Leu Lys Lys Leu Glu
                835                 840                 845

Ser Lys Ile Asn Lys Val Phe Ser Thr Pro Ile Pro Phe Ser Tyr Ser
850                 855                 860

Lys Asn Leu Asp Cys Trp Val Asp Asn Glu Glu Asp Ile Asp Val Ile
865                 870                 875                 880

Leu Lys Lys Ser Thr Ile Leu Asn Leu Asp Ile Asn Asn Asp Ile Ile
                885                 890                 895

Ser Asp Ile Ser Gly Phe Asn Ser Ser Val Ile Thr Tyr Pro Asp Ala
                900                 905                 910

Gln Leu Val Pro Gly Ile Asn Gly Lys Ala Ile His Leu Val Asn Asn
                915                 920                 925

Glu Ser Ser Glu Val Ile Val His Lys Ala Met Asp Ile Glu Tyr Asn
930                 935                 940

Asp Met Phe Asn Asn Phe Thr Val Ser Phe Trp Leu Arg Val Pro Lys
945                 950                 955                 960

Val Ser Ala Ser His Leu Glu Gln Tyr Gly Thr Asn Glu Tyr Ser Ile
                965                 970                 975

Ile Ser Ser Met Lys Lys His Ser Leu Ser Ile Gly Ser Gly Trp Ser
                980                 985                 990

Val Ser Leu Lys Gly Asn Asn Leu Ile Trp Thr Leu Lys Asp Ser Ala
                995                 1000                1005

Gly Glu Val Arg Gln Ile Thr Phe Arg Asp Leu Pro Asp Lys Phe
        1010                1015                1020

Asn Ala Tyr Leu Ala Asn Lys Trp Val Phe Ile Thr Ile Thr Asn
        1025                1030                1035

Asp Arg Leu Ser Ser Ala Asn Leu Tyr Ile Asn Gly Val Leu Met
        1040                1045                1050

Gly Ser Ala Glu Ile Thr Gly Leu Gly Ala Ile Arg Glu Asp Asn
        1055                1060                1065

Asn Ile Thr Leu Lys Leu Asp Arg Cys Asn Asn Asn Asn Gln Tyr
        1070                1075                1080

Val Ser Ile Asp Lys Phe Arg Ile Phe Cys Lys Ala Leu Asn Pro
        1085                1090                1095

Lys Glu Ile Glu Lys Leu Tyr Thr Ser Tyr Leu Ser Ile Thr Phe
        1100                1105                1110

Leu Arg Asp Phe Trp Gly Asn Pro Leu Arg Tyr Asp Thr Glu Tyr
        1115                1120                1125

Tyr Leu Ile Pro Val Ala Ser Ser Ser Lys Asp Val Gln Leu Lys
        1130                1135                1140

Asn Ile Thr Asp Tyr Met Tyr Leu Thr Asn Ala Pro Ser Tyr Thr
        1145                1150                1155

Asn Gly Lys Leu Asn Ile Tyr Tyr Arg Arg Leu Tyr Asn Gly Leu
        1160                1165                1170
```

| | | | | | | | | | | | |
|---|---|---|---|---|---|---|---|---|---|---|---|
| Lys | Phe | Ile | Ile | Lys | Arg | Tyr | Thr | Pro | Asn | Asn | Glu | Ile | Asp | Ser |
| | 1175 | | | | 1180 | | | | | 1185 | |

Phe Val Lys Ser Gly Asp Phe Ile Lys Leu Tyr Val Ser Tyr Asn
    1190                1195                1200

Asn Asn Glu His Ile Val Gly Tyr Pro Lys Asp Gly Asn Ala Phe
    1205                1210                1215

Asn Asn Leu Asp Arg Ile Leu Leu Val Gly Tyr Asn Ala Pro Gly
    1220                1225                1230

Ile Pro Leu Tyr Lys Lys Met Glu Ala Val Lys Leu Arg Asp Leu
    1235                1240                1245

Lys Thr Tyr Ser Val Gln Leu Lys Leu Tyr Asp Asp Lys Asn Ala
    1250                1255                1260

Ser Leu Gly Leu Val Gly Thr His Asn Gly Gln Ile Gly Asn Asp
    1265                1270                1275

Pro Asn Arg Asp Ile Leu Ile Ala Ser Asn Ala Tyr Phe Asn His
    1280                1285                1290

Leu Lys Asp Lys Ile Leu Gly Cys Asp Trp Tyr Phe Val Pro Thr
    1295                1300                1305

Asp Glu Gly Trp Thr Asn Asp
    1310                1315

<210> SEQ ID NO 9
<211> LENGTH: 4559
<212> TYPE: DNA
<213> ORGANISM: Artificial Sequence
<220> FEATURE:
<223> OTHER INFORMATION: Synthetic - DNA encoding SARS-COV-2(RBD)-8MTT

<400> SEQUENCE: 9

```
catatgccga acattaccaa cctgtgcccg tttggcgaag tgtttaacgc gacccgtttt      60
gcgagcgtgt atgcgtggaa ccgtaaacgt attagcaact gcgtggcgga ttatagcgtg     120
ctgtataaca gcgcgagctt tagcaccttt aaatgctatg gcgtgagccc gaccaaactg     180
aacgatctgt gctttaccaa cgtgtatgcg gatagctttg tgattcgtgg cgatgaagtg     240
cgtcagattg cgccgggcca gaccggcaaa attgcggatt ataactataa actgccggat     300
gattttaccg gctgcgtgat tgcgtggaac agcaacaacc tggatagcaa agtgggcggc     360
aactataact atctgtatcg tctgtttcgt aaaagcaacc tgaaaccgtt tgaacgtgat     420
attagcaccg aaatttatca ggcgggcagc accccgtgca acggcgtgga aggctttaac     480
tgctattttc cgctgcagag ctatggcttt cagccgacca acggcgtggg ctatcagccg     540
tatcgtgtgg tggtgctgag ctttgaactg ctgcatgcgc cggcggtgg cggcggtgag     600
ctcatgccga ttaccattaa caactttcgt tatagcgatc cggtgaacaa cgataccatt     660
attatgatgg aaccgccggc gtgcaaaggc ctggatattt attataaagc gtttaaaatt     720
accgatcgta tttggattgt gccggaacgt atgaatttg caccaaaacc ggaagatttc     780
aacccgccga gcagcctgat tgaaggcgcg agcgaatatt atgatccgaa ctatctgcgt     840
accgatagcg ataaagatcg tttcctgcag accatggtga actgtttaa ccgtattaag     900
aacaacgtgg cgggcgaagc gctgctggat aaaattatta cgcgattcc gtatctgggc     960
aacagctata gcctgctgga taaatttgat accaacagca cagcgtgag ctttaacctg    1020
ctggaacaag atccgagcgg cgcgaccacc aaaagcgcga tgctgaccaa cctgattatt    1080
ttcggccggg gccggtgct gaacaaaaac gaagtgcgtg cattgtgct gcgtgtggat    1140
aacaagaact atttcccgtg ccgtgatggc tttggcagca ttatgcagat ggcgttttgc    1200
```

```
ccggaatatg tgccgacctt tgataacgtg attgaaaaca ttaccagcct gaccattggc   1260
aaaagcaaat atttccaaga tccggcgctg aaactgatgc atcaactgat tcatgtgctg   1320
catggcctgt atggcatgca ggtgagcagc catgaaatta ttccgagcaa acaggaaatt   1380
tatatgcagc ataccatcc gattagcgcg aagaactgt ttacctttgg cggccaggat    1440
gcgaacctga ttagcattga tattaagaac gatctgtatg aaaagaccct gaacgattat   1500
aaagcgattg cgaacaaact gagccaggtg accagctgca acgatccgaa cattgatatt   1560
gatagctata aacagattta tcagcagaaa tatcagtttg ataaagatag caacggccag   1620
tatattgtga acgaagataa atttcagatt ctgtataaca gcattatgta tggctttacc   1680
gaaattgaac tgggcaagaa atttaacatt aaaaccgctc tgagcttttt tagcatgaac   1740
catgatccgg tgaaaattcc gaacctgctg gatgatacca tttataacga taccgaaggc   1800
tttaacattg aaagcaaaga cctgaaaagc gaatataaag gccagaacat gcgtgtgaac   1860
accaacgcgt tcgtaacgt ggatggatcc ggcctggtga gcaaactgat tggcctgtgc    1920
aagaagatta ttccgccgac caacattcgt gagaacctgt ataccgtac cgcgagcctg    1980 accgatctgg gcggcgaact gtgcattaag attaagaacg aagatctgac ctttattgcg   2040
gagaagaaca gctttagcga agaaccgttt caggatgaaa ttgtgagcta aacaccaag    2100 aacaaaccgc tgaactttaa ctatagcctg ataaaatta ttgtggatta aacctgcag     2160 agcaagatta ccctgccgaa cgatcgtacc accccggtga ccaaaggcat tccgtatgcg   2220
ccggaatata gagcaacgc ggcgagcacc attgaaattc ataacattga tgataacacc    2280
atttatcagt atctgtatgc gcagaagagc ccgaccaccc tgcagcgtat taccatgacc   2340
aacagcgtgg atgatgcgct gattaacagc accaaaattt atagctattt tccgagcgtg   2400
attagcaaag tgaaccaggg cgcgcagggc attctgtttc tgcagtgggt gcgtgatatt   2460
attgatgatt ttaccaacga aagcagccag aaaaccacca ttgataaaat tagcgatgtg   2520
agcaccattg tgccgtatat tggcccggcg ctgaacattg tgaaacaggg ctatgaaggc   2580
aactttattg gcgcgctgga aaccaccggc gtggtgctgc tgctggaata tattccggaa   2640
attaccctgc cggtgattgc ggcgctgagc attgcgaaa gcagcaccca gaaagagaag    2700
attattaaaa ccattgataa ctttctggag aaacgttatg agaaatggat tgaagtgtat   2760
aaactggtga agcgaaatg ctgggcacc gtgaacaccc agtttcagaa acgtagctat     2820
cagatgtatc gtagcctgga atatcaggtg gatgcgatta agaaaattat tgattatgaa   2880
tataagattt atagcggccc ggatgccgaa cagattgcgg atgaaattaa caacctgaaa   2940
aacaaactgg aagagaaagc gaacaaagcg atgattaaca ttaacatctt tatgcgtgaa   3000
agcagccgta gctttctggt gaaccagatg attaacgaag cgaagaaaca gctgctggaa   3060 tttgatacccc agagcaagaa cattctgatg cagtatatta aagcgaacag caatttatt    3120 ggcattaccg aactgaagaa actggaaagc aaaattaaca aagtgtttag cacccccgatt  3180 ccgtttagct atagcaagaa cctggattgc tgggtggata cgaagaaga tattgatgtg    3240 attctgaaga gagcaccat tctgaacctg gatattaaca cgatattat tagcgatatt     3300 agcggcttca acagcagcgt gattacctat ccgatgcgc agctggtacc gggcattaac    3360
ggcaaagcga ttcatctggt gaacaacgaa agcagcgaag tgattgtgca taaagcgatg   3420
gatattgaat ataacgatat gttcaacaac tttaccgtga gctttggct gcgtgtgccg    3480 aaagtgagcg cgagccatct ggaacagtat ggcaccaacg aatatagcat tattagcagc   3540
```

```
atgaagaaac atagcctgag cattggcagc ggctggagcg tgagcctgaa aggcaacaac    3600
ctgatttgga ccctgaaaga tagcgcgggc gaagtgcgtc agattacctt cgtgatctg     3660
ccggataagt ttaacgcgta tctggcgaac aaatgggtgt tattaccat taccaacgat     3720
cgtctgagca gcgcgaacct gtatattaac ggcgtgctga tgggcagcgc ggaaattacc    3780
ggcctgggcg cgattcgtga agataacaac attaccctga actggatcg ttgcaacaat     3840
aacaaccagt atgtgagcat tgataaattt cgtattttt gcaaagcgct gaacccgaaa     3900
gaaattgaaa actgtatac cagctatctg agcattacct ttctgcgtga ttttggggc     3960
aacccgctgc gttatgatac cgaatattat ctgattccgg tggcgagcag tagcaaagat    4020
gtgcagctga agaacattac cgattatatg tatctgacca acgcgccgag ctataccaac    4080
ggcaaactga acatttacta tcgtcgtctg tataacggcc tgaaattcat tattaaacgt    4140
tatccccga ataacgaaat tgatagcttt gtgaaaagcg gcgatttat taaactgtat      4200
gtgagctata acaataacga acatattgtg gcctatccga agatggcaa cgcgtttaat    4260
aacctggatc gtattctgct ggtgggctat aacgcgccgg gcattccgct gtataagaag    4320
atggaagcgg tgaaactgcg tgatctgaaa acctatagcg tgcagctgaa actgtatgat    4380
gataagaacg cgagcctggg cctggttgga acccataacg gtcagattgg caacgatcca    4440
aaccgtgata ttctgattgc gagcaacgcg tattttaacc atctgaaaga caagatcctg    4500
ggctgtgatt ggtacttcgt tccgacagat gaaggctgga ccaacgatta agcggccgc    4559
```

```
<210> SEQ ID NO 10
<211> LENGTH: 1516
<212> TYPE: PRT
<213> ORGANISM: Artificial Sequence
<220> FEATURE:
<223> OTHER INFORMATION: Synthetic - SARS-COV-2(RBD)-8MTT protein

<400> SEQUENCE: 10

His Met Pro Asn Ile Thr Asn Leu Cys Pro Phe Gly Glu Val Phe Asn
1               5                   10                  15

Ala Thr Arg Phe Ala Ser Val Tyr Ala Trp Asn Arg Lys Arg Ile Ser
            20                  25                  30

Asn Cys Val Ala Asp Tyr Ser Val Leu Tyr Asn Ser Ala Ser Phe Ser
        35                  40                  45

Thr Phe Lys Cys Tyr Gly Val Ser Pro Thr Lys Leu Asn Asp Leu Cys
    50                  55                  60

Phe Thr Asn Val Tyr Ala Asp Ser Phe Val Ile Arg Gly Asp Glu Val
65                  70                  75                  80

Arg Gln Ile Ala Pro Gly Gln Thr Gly Lys Ile Ala Asp Tyr Asn Tyr
                85                  90                  95

Lys Leu Pro Asp Asp Phe Thr Gly Cys Val Ile Ala Trp Asn Ser Asn
            100                 105                 110

Asn Leu Asp Ser Lys Val Gly Gly Asn Tyr Asn Tyr Leu Tyr Arg Leu
        115                 120                 125

Phe Arg Lys Ser Asn Leu Lys Pro Phe Glu Arg Asp Ile Ser Thr Glu
    130                 135                 140

Ile Tyr Gln Ala Gly Ser Thr Pro Cys Asn Gly Val Glu Gly Phe Asn
145                 150                 155                 160

Cys Tyr Phe Pro Leu Gln Ser Tyr Gly Phe Gln Pro Thr Asn Gly Val
                165                 170                 175

Gly Tyr Gln Pro Tyr Arg Val Val Val Leu Ser Phe Glu Leu Leu His
            180                 185                 190
```

-continued

```
Ala Pro Gly Gly Gly Gly Glu Leu Met Pro Ile Thr Ile Asn Asn
        195                 200                 205

Phe Arg Tyr Ser Asp Pro Val Asn Asn Asp Thr Ile Ile Met Met Glu
210                 215                 220

Pro Pro Ala Cys Lys Gly Leu Asp Ile Tyr Tyr Lys Ala Phe Lys Ile
225                 230                 235                 240

Thr Asp Arg Ile Trp Ile Val Pro Glu Arg Tyr Glu Phe Gly Thr Lys
                245                 250                 255

Pro Glu Asp Phe Asn Pro Pro Ser Ser Leu Ile Glu Gly Ala Ser Glu
                260                 265                 270

Tyr Tyr Asp Pro Asn Tyr Leu Arg Thr Asp Ser Asp Lys Asp Arg Phe
                275                 280                 285

Leu Gln Thr Met Val Lys Leu Phe Asn Arg Ile Lys Asn Asn Val Ala
        290                 295                 300

Gly Glu Ala Leu Leu Asp Lys Ile Ile Asn Ala Ile Pro Tyr Leu Gly
305                 310                 315                 320

Asn Ser Tyr Ser Leu Leu Asp Lys Phe Asp Thr Asn Ser Asn Ser Val
                325                 330                 335

Ser Phe Asn Leu Leu Glu Gln Asp Pro Ser Gly Ala Thr Thr Lys Ser
        340                 345                 350

Ala Met Leu Thr Asn Leu Ile Ile Phe Gly Pro Gly Pro Val Leu Asn
        355                 360                 365

Lys Asn Glu Val Arg Gly Ile Val Leu Arg Val Asp Asn Lys Asn Tyr
370                 375                 380

Phe Pro Cys Arg Asp Gly Phe Gly Ser Ile Met Gln Met Ala Phe Cys
385                 390                 395                 400

Pro Glu Tyr Val Pro Thr Phe Asp Asn Val Ile Glu Asn Ile Thr Ser
                405                 410                 415

Leu Thr Ile Gly Lys Ser Lys Tyr Phe Gln Asp Pro Ala Leu Lys Leu
                420                 425                 430

Met His Gln Leu Ile His Val Leu His Gly Leu Tyr Gly Met Gln Val
        435                 440                 445

Ser Ser His Glu Ile Ile Pro Ser Lys Gln Glu Ile Tyr Met Gln His
        450                 455                 460

Thr Tyr Pro Ile Ser Ala Glu Glu Leu Phe Thr Phe Gly Gly Gln Asp
465                 470                 475                 480

Ala Asn Leu Ile Ser Ile Asp Ile Lys Asn Asp Leu Tyr Glu Lys Thr
                485                 490                 495

Leu Asn Asp Tyr Lys Ala Ile Ala Asn Lys Leu Ser Gln Val Thr Ser
                500                 505                 510

Cys Asn Asp Pro Asn Ile Asp Ile Asp Ser Tyr Lys Gln Ile Tyr Gln
        515                 520                 525

Gln Lys Tyr Gln Phe Asp Lys Asp Ser Asn Gly Gln Tyr Ile Val Asn
        530                 535                 540

Glu Asp Lys Phe Gln Ile Leu Tyr Asn Ser Ile Met Tyr Gly Phe Thr
545                 550                 555                 560

Glu Ile Glu Leu Gly Lys Lys Phe Asn Ile Lys Thr Ala Leu Ser Phe
                565                 570                 575

Phe Ser Met Asn His Asp Pro Val Lys Ile Pro Asn Leu Leu Asp Asp
                580                 585                 590

Thr Ile Tyr Asn Asp Thr Glu Gly Phe Asn Ile Glu Ser Lys Asp Leu
                595                 600                 605
```

-continued

```
Lys Ser Glu Tyr Lys Gly Gln Asn Met Arg Val Asn Thr Asn Ala Phe
610             615                 620
Arg Asn Val Asp Gly Ser Gly Leu Val Ser Lys Leu Ile Gly Leu Cys
625                 630                 635                 640
Lys Lys Ile Ile Pro Pro Thr Asn Ile Arg Glu Asn Leu Tyr Asn Arg
                645                 650                 655
Thr Ala Ser Leu Thr Asp Leu Gly Gly Glu Leu Cys Ile Lys Ile Lys
            660                 665                 670
Asn Glu Asp Leu Thr Phe Ile Ala Glu Lys Asn Ser Phe Ser Glu Glu
                675                 680                 685
Pro Phe Gln Asp Glu Ile Val Ser Tyr Asn Thr Lys Asn Lys Pro Leu
690                 695                 700
Asn Phe Asn Tyr Ser Leu Asp Lys Ile Ile Val Asp Tyr Asn Leu Gln
705                 710                 715                 720
Ser Lys Ile Thr Leu Pro Asn Asp Arg Thr Thr Pro Val Thr Lys Gly
            725                 730                 735
Ile Pro Tyr Ala Pro Glu Tyr Lys Ser Asn Ala Ala Ser Thr Ile Glu
            740                 745                 750
Ile His Asn Ile Asp Asp Asn Thr Ile Tyr Gln Tyr Leu Tyr Ala Gln
            755                 760                 765
Lys Ser Pro Thr Thr Leu Gln Arg Ile Thr Met Thr Asn Ser Val Asp
770                 775                 780
Asp Ala Leu Ile Asn Ser Thr Lys Ile Tyr Ser Tyr Phe Pro Ser Val
785                 790                 795                 800
Ile Ser Lys Val Asn Gln Gly Ala Gln Gly Ile Leu Phe Leu Gln Trp
                805                 810                 815
Val Arg Asp Ile Ile Asp Asp Phe Thr Asn Glu Ser Ser Gln Lys Thr
            820                 825                 830
Thr Ile Asp Lys Ile Ser Asp Val Ser Thr Ile Val Pro Tyr Ile Gly
            835                 840                 845
Pro Ala Leu Asn Ile Val Lys Gln Gly Tyr Glu Gly Asn Phe Ile Gly
850                 855                 860
Ala Leu Glu Thr Thr Gly Val Val Leu Leu Leu Glu Tyr Ile Pro Glu
865                 870                 875                 880
Ile Thr Leu Pro Val Ile Ala Ala Leu Ser Ile Ala Glu Ser Ser Thr
                885                 890                 895
Gln Lys Glu Lys Ile Ile Lys Thr Ile Asp Asn Phe Leu Glu Lys Arg
                900                 905                 910
Tyr Glu Lys Trp Ile Glu Val Tyr Lys Leu Val Lys Ala Lys Trp Leu
            915                 920                 925
Gly Thr Val Asn Thr Gln Phe Gln Lys Arg Ser Tyr Gln Met Tyr Arg
930                 935                 940
Ser Leu Glu Tyr Gln Val Asp Ala Ile Lys Lys Ile Ile Asp Tyr Glu
945                 950                 955                 960
Tyr Lys Ile Tyr Ser Gly Pro Asp Ala Glu Gln Ile Ala Asp Glu Ile
            965                 970                 975
Asn Asn Leu Lys Asn Lys Leu Glu Glu Lys Ala Asn Lys Ala Met Ile
                980                 985                 990
Asn Ile Asn Ile Phe Met Arg Glu  Ser Ser Arg Ser Phe  Leu Val Asn
            995                 1000                1005
Gln Met  Ile Asn Glu Ala Lys  Lys Gln Leu Leu Glu  Phe Asp Thr
        1010                1015                1020
Gln Ser  Lys Asn Ile Leu Met  Gln Tyr Ile Lys Ala  Asn Ser Lys
```

```
                    1025                1030                1035
Phe Ile Gly Ile Thr Glu Leu Lys Lys Leu Glu Ser Lys Ile Asn
        1040                1045                1050
Lys Val Phe Ser Thr Pro Ile Pro Phe Ser Tyr Ser Lys Asn Leu
        1055                1060                1065
Asp Cys Trp Val Asp Asn Glu Glu Asp Ile Asp Val Ile Leu Lys
        1070                1075                1080
Lys Ser Thr Ile Leu Asn Leu Asp Ile Asn Asn Asp Ile Ile Ser
        1085                1090                1095
Asp Ile Ser Gly Phe Asn Ser Ser Val Ile Thr Tyr Pro Asp Ala
        1100                1105                1110
Gln Leu Val Pro Gly Ile Asn Gly Lys Ala Ile His Leu Val Asn
        1115                1120                1125
Asn Glu Ser Ser Glu Val Ile Val His Lys Ala Met Asp Ile Glu
        1130                1135                1140
Tyr Asn Asp Met Phe Asn Asn Phe Thr Val Ser Phe Trp Leu Arg
        1145                1150                1155
Val Pro Lys Val Ser Ala Ser His Leu Glu Gln Tyr Gly Thr Asn
        1160                1165                1170
Glu Tyr Ser Ile Ile Ser Ser Met Lys Lys His Ser Leu Ser Ile
        1175                1180                1185
Gly Ser Gly Trp Ser Val Ser Leu Lys Gly Asn Asn Leu Ile Trp
        1190                1195                1200
Thr Leu Lys Asp Ser Ala Gly Glu Val Arg Gln Ile Thr Phe Arg
        1205                1210                1215
Asp Leu Pro Asp Lys Phe Asn Ala Tyr Leu Ala Asn Lys Trp Val
        1220                1225                1230
Phe Ile Thr Ile Thr Asn Asp Arg Leu Ser Ser Ala Asn Leu Tyr
        1235                1240                1245
Ile Asn Gly Val Leu Met Gly Ser Ala Glu Ile Thr Gly Leu Gly
        1250                1255                1260
Ala Ile Arg Glu Asp Asn Asn Ile Thr Leu Lys Leu Asp Arg Cys
        1265                1270                1275
Asn Asn Asn Asn Gln Tyr Val Ser Ile Asp Lys Phe Arg Ile Phe
        1280                1285                1290
Cys Lys Ala Leu Asn Pro Lys Glu Ile Glu Lys Leu Tyr Thr Ser
        1295                1300                1305
Tyr Leu Ser Ile Thr Phe Leu Arg Asp Phe Trp Gly Asn Pro Leu
        1310                1315                1320
Arg Tyr Asp Thr Glu Tyr Tyr Leu Ile Pro Val Ala Ser Ser Ser
        1325                1330                1335
Lys Asp Val Gln Leu Lys Asn Ile Thr Asp Tyr Met Tyr Leu Thr
        1340                1345                1350
Asn Ala Pro Ser Tyr Thr Asn Gly Lys Leu Asn Ile Tyr Tyr Arg
        1355                1360                1365
Arg Leu Tyr Asn Gly Leu Lys Phe Ile Ile Lys Arg Tyr Thr Pro
        1370                1375                1380
Asn Asn Glu Ile Asp Ser Phe Val Lys Ser Gly Asp Phe Ile Lys
        1385                1390                1395
Leu Tyr Val Ser Tyr Asn Asn Asn Glu His Ile Val Gly Tyr Pro
        1400                1405                1410
Lys Asp Gly Asn Ala Phe Asn Asn Leu Asp Arg Ile Leu Leu Val
        1415                1420                1425
```

```
Gly Tyr Asn Ala Pro Gly Ile Pro Leu Tyr Lys Lys Met Glu Ala
    1430            1435            1440

Val Lys Leu Arg Asp Leu Lys Thr Tyr Ser Val Gln Leu Lys Leu
    1445            1450            1455

Tyr Asp Asp Lys Asn Ala Ser Leu Gly Leu Val Gly Thr His Asn
    1460            1465            1470

Gly Gln Ile Gly Asn Asp Pro Asn Arg Asp Ile Leu Ile Ala Ser
    1475            1480            1485

Asn Ala Tyr Phe Asn His Leu Lys Asp Lys Ile Leu Gly Cys Asp
    1490            1495            1500

Trp Tyr Phe Val Pro Thr Asp Glu Gly Trp Thr Asn Asp
    1505            1510            1515
```